United States Patent [19]

Shannon, Sr.

[11] Patent Number: 5,966,673

[45] Date of Patent: *Oct. 12, 1999

[54] SYSTEM AND METHOD FOR COMPUTERIZED EVALUATION OF GEMSTONES

[75] Inventor: Paul T. Shannon, Sr., Macon, Ga.

[73] Assignee: Diamond Technologies, Inc., Macon, Ga.

[*] Notice: This patent issued on a continued prosecution application filed under 37 CFR 1.53(d), and is subject to the twenty year patent term provisions of 35 U.S.C. 154(a)(2).

[21] Appl. No.: 08/782,889

[22] Filed: Jan. 10, 1997

[51] Int. Cl.⁶ ....................................................... B44B 5/00
[52] U.S. Cl. ................................ 702/35; 364/507; 356/30
[58] Field of Search ................................... 364/525, 507; 356/30, 31, 303, 306, 317, 318, 128, 148, 237; 702/35

[56] References Cited

U.S. PATENT DOCUMENTS 3,947,120   3/1976   Bar-Issac et al. ........................... 356/30

OTHER PUBLICATIONS

"Code V®," Product Brochure, Optical Research Associates, Pasadena, California ©1993.
Lewotsky, K., "Three–Dimensional Modeling Program Simplifies Optomechanical Design," reprint from *Laser Focus World*, PennWell Publishing Company, Mar. 1995.
Hayford, M. et al., "A Building–Block Approach to Optical–Design Software," reprint from *Photonics Spectra®*, Laurin Publishing Co, Inc., May 1996.
Abernathy, M., "Non–Sequential Raytracing: Enlightened Software for Illumination Engineering," *Optics and Photonics News*, Nov. 1996, pp. 22–26.

"Illumination Design With LightTools," Product Brochure, Optical Research Associates, Pasadena, California, Dec. 1996.
Gilbertson, A. et al., "What Tolkowsky Really Said," *Rapaport Diamond Report*, Jan. 10, 1997, pp. 35 and 37.
"ASAP 5.0 for Windows," Promotional Circular, Breault Research Organization, Tucson, Arizona, ©1996.
"GLAD—General Laser Analysis and Design Software," Product Brochure, Focus Software, Inc., Tucson, Arizona.
"LensVIEW™," Promotional Circular, Focus Software, Inc., Tucson, Arizona.
"Light Tools," Product Brochure, Optical Research Associates, Pasadena, California.
"OPTICAD®," Product Brochure, Focus Software, Inc., Tucson, Arizona.
"OSLO Version 5," Promotional Circular, Sinclair Optics, Fairport, New York.
"ZEMAX Optical Design Program," Product Brochure, Focus Software, Inc., Tucson, Arizona.
"ZEMAX Optical Design Software," Promotional Circular, Focus Software, Inc., Tucson, Arizona.

*Primary Examiner*—Thomas Peeso
*Attorney, Agent, or Firm*—Sterne, Kessler, Goldstein & Fox P.L.L.C.

[57] ABSTRACT

A system and method for computerized grading of the cut of a gemstone. The system includes a gemstone model and an illumination model. The gemstone model defines the cut of the gemstone in three dimensions with reference to the facets of the gemstone. The illumination model defines light projected onto the gemstone. The method includes the steps of determining a beam of light refracted into the gemstone from the illumination model for at least one of the facets, tracing reflections of the beam of light within the gemstone, and measuring at least one light beam refracted out of the gemstone model. The measurements of the refracted light are used to evaluate the gemstone.

74 Claims, 56 Drawing Sheets

29(a)

29(b)

SYSTEM AND METHOD FOR COMPUTERIZED EVALUATION OF GEMSTONES

BACKGROUND OF THE INVENTION

1.0 Field of the Invention

This invention relates generally to gemstones, and more particularly to a computer-based system and method for evaluation of a gemstone by modeling light propagating through the gemstone.

2.0 Related Art

Very few subjects have plagued the diamond industry more than the subject of cut. The basis for conventional cut grading of gemstones was established in 1919 by Marcel Tolkowsky, an industrious Antwerp diamond cutter. In his mathematical dissertation entitled "Diamond Design, A Study of the Reflection and Refraction of Light in a Diamond," Tolkowsky established mathematically an optimal brilliant cut for a diamond that is still widely used today. The Tolkowsky cut defined certain dimensions (that is, table diameter, crown height and pavilion depth) of the diamond as percentages of its girdle diameter. Thus, the Tolkowsky cut is scalable, and so can be used for a different sizes of this style of cut.

Although Tolkowsky's cut represented a milestone in the industry, it is based upon a two-dimensional profile, and so does not account for three-dimensional reflective and refractive effects. Furthermore, the Tokowsky model doesn't account for differences or variations in facet types, sizes or positions, or assymetries present in some cuts.

Further, Tolkowsky apparently relied upon a single incident light ray to create the Tolkowski cut. This lighting model, therefore, has some shorfalls due to the fact that an actual gemstone is normally illuminated from a myriad of directions. Despite the shortcomings of the Tolkowsky cut, it is still in use today. Many gemstone cut grades continue to be based on deviations from the proportions of the Tolkowsky cut.

SUMMARY OF THE INVENTION

The present invention is directed toward a system and method for modeling and evaluating the propagation of light through an optical system. More specifically, in a preferred embodiment, the present invention provides a system and method for evaluating properties of a gemstone using a gemstone model. A key feature of the invention is that it provides a computer-based system and method for evaluating and grading the cut of a gemstone which can be used for determining an ideal or near-ideal cut. Thus, the invention can be used to grade the cut of an existing cut stone or to determine ideal dimensions for a stone to be cut.

Data describing the stone to be evaluated is collected into a data set. The data in the data set includes the material characteristics of the stone. This data also includes geometrical cut data, such as information regarding an existing cut or a proposed cut. The cut data can include, for example, without limitation, data regarding the number, type and placements of facets, and cut dimensions (e.g., pavillion, crown and table percentages). The data set represents a three-dimensional model of a gemstone with an existing or proposed cut.

According to the invention, an illumination model comprised of one or more light sources is used to "illuminate" the stone. Light beams from the light sources are traced or modeled as they enter the stone, are reflected among the various facets inside the stone, and exit the stone. One or more attributes of the light exiting the stone is measured to determine the quality of the cut. These attributes can include, for example, intensity, dispersion, scintillation, and other attributes.

Preferably, numerous measurements of the exiting light are taken at a plurality of points surrounding the crown of the stone. As a result, the light exiting the stone is evaluated at various viewing angles and from various locations on the model. Attributes of the light exiting the stone are measured and these measurements are used to evaluate the cut of the gemstone.

One advantage of the present invention is that the grade of a gemstone can be determined based on the propagation of light within the gemstone.

Another advantage of the present invention is that an accurate measure of composite brilliance for a gemstone is obtained.

Further features and advantages of the present invention, as well as the structure and operation of various embodiments of the present invention, are described in detail below with reference to the accompanying drawings.

BRIEF DESCRIPTION OF THE DRAWINGS

The present invention is described with reference to the accompanying drawings. In the drawings, the left-most digit(s) of a reference number identifies the drawing in which the reference number first appears.

Figure 1:
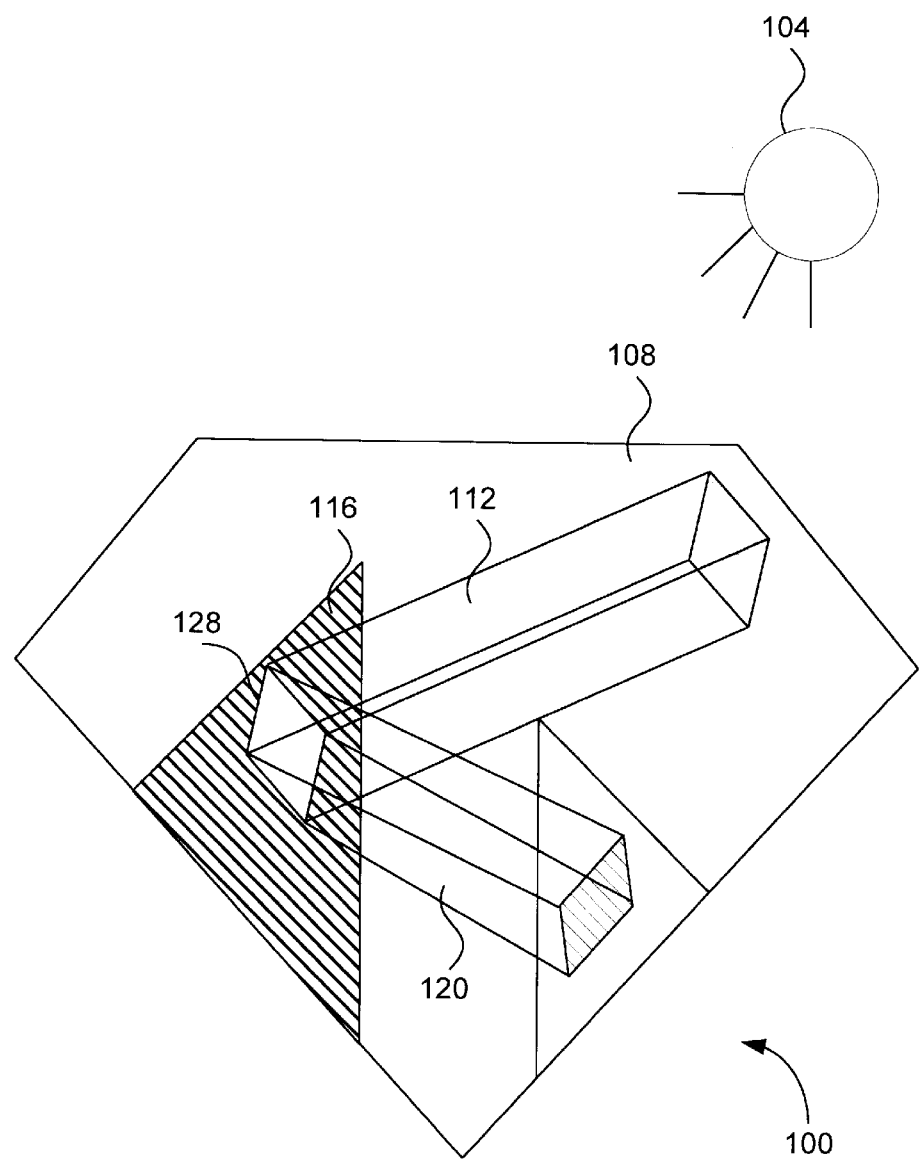
FIG. 1 is a diagram illustrating a scenario where a light beam is refracted into a gemstone and is reflected off of a facet within the gemstone.

DETAILED DESCRIPTION OF THE EMBODIMENTS 1.0 Overview and Discussion of the Invention The present invention is directed toward a system and method for modeling and evaluating the propagation of light through an optical system. More specifically, in a preferred embodiment, the present invention provides a system and method for evaluating properties of a gemstone using a gemstone model. A key feature of the invention is that it provides a computer-based system and method for evaluating and grading the cut of a gemstone which can be used for determining an ideal or near-ideal cut. Thus, the invention can be used to grade the cut of an existing cut stone or to determine ideal dimensions for a stone to be cut.

Generally speaking, in accordance with the invention, data on the stone to be evaluated is collected into a data set. The data in the data set includes the material characteristics of the stone. This data also includes cut data, such as information regarding an existing cut or a proposed cut. The cut data can include, for example, without limitation, data regarding the number, type and placements of facets, and cut dimensions (e.g., pavillion, crown and table percentages).

The data set represents a three-dimensional model of a gemstone with an existing or proposed cut. Any of several different data structures can be used for this data set. One such data structure, and variants thereof, are described in this document. After reading this document, it will become apparent to a person skilled in the relevant art how to implement the invention using alternative data structures.

According to the invention, an illumination model comprised of one or more light sources is used to "illuminate" the stone. Light beams from the light sources are traced or modeled as they enter the stone, are reflected among the various facets inside the stone, and exit the stone. One or more attributes of the light exiting the stone are measured to determine the quality of the cut. These attributes can include, for example, intensity, dispersion, scintillation, and other attributes.

Preferably, numerous measurements of the exiting light are taken at a plurality of points surrounding the crown of the stone. As a result, the light exiting the stone is evaluated at various viewing angles and from various locations on the model. Attributes of the light exiting the stone are measured and these measurements are used to evaluate the cut of the gemstone.

For ease of discussion, the operation of the present invention is described in evaluating a gemstone with a round cut. Of course, the invention can be used to evaluate gemstones with other types of cuts (such as brilliant, emerald, marquis, pear, etc.) without departing from the spirit and scope of the present invention.

2.0 Example Environment

Before describing the invention in great detail, it is useful to describe an example environment in which the invention can be implemented. In a broad sense, the invention can be implemented to model the propagation of light through any optical system, and to evaluate the performance of the optical system based on the modeled propagation. Such an optical system may have a plurality of lenses, mirrors, surfaces, or other devices which can interact with and potentially alter the properties of light in the optical system.

In an alternative environment, the propagation of light is modeled through a gemstone. One or more properties or attributes of the light exiting the gemstone are measured to evaluate the gemstone.

For ease of discussion, the present invention is described in terms of the example environment of the gemstone. Description in these terms is provided for convenience only. It is not intended that the invention be limited to application in this example environment. In fact, after reading the following description, it will become apparent to a person skilled in the relevant art how to implement the invention in alternative environments.

3.0 Light Propagation in Gemstones

As stated above, in a preferred implementation, the invention models the propagation of light in a gemstone to evaluate the characteristics of the stone. Before describing the invention in detail, it is useful to describe an example scenario of a light beam being refracted into, reflected within and refracted out of a simple gemstone.

FIG. 1 is a diagram illustrating a scenario where a light beam is refracted into a gemstone and is reflected off of a facet within the gemstone. Referring to FIG. 1, a stone 100 is illuminated by a light source 104. In FIG. 1 a facet 108 on the crown of stone 100 is illuminated by light source 104. A light beam 112 is refracted into stone 100 by facet 108.

In the example illustrated in FIG. 1, light beam 112 impinges upon a facet 116 on the pavilion of the stone. Depending on the angle of incidence, this creates a reflected beam 120, or a refracted beam 124 out of the stone, or both.

In this document, each beam, and its resultant reflected or refracted beam are referred to as a parent beam and a child beam for ease of description. For example, in the example illustrated in FIG. 1, beam 112 is referred to as the parent beam of child beam 120. For a subsequent reflection of child beam 120, child beam 120 is then referred to as the parent beam of the resultant reflected beam.

Also for ease of description, facets are referred to as either a sending facet or a receiving facet. In the example illustrated in FIG. 1, facet 108 is the sending facet for beam 112. Facet 116 is referred to as the receiving facet for beam 112. Similarly, facet 116 is the sending facet for beam 120.

The area of the beam which overlaps the area of the facet is referred to as the overlap area. For example, for beam 112 and facet 116, the overlap area is the cross hatched area illustrated. The overlap area can be described as a projection of beam 112 onto receiving facet 116.

Note that for simplicity, light beam 112 is only illustrated as impinging on a single facet in the pavilion. In reality, light beam 112 may actually impinge upon several facets, or portions thereof, within the stone resulting in a plurality of child beams. The shape of the resultant child beams is dictated by the shape of the overlap area of the parent beam with the receiving facet (which is the sending facet of the child beam).

In order to aid in the description of complex processes disclosed herein, many of these processes are described in terms of simple examples. These examples are valuable aids in allowing the reader to better grasp the techniques described. However, after reading this description it will become apparent to a person skilled in the relevant art that the invention is not limited to application to the described examples.

4.0 Evaluation of a Gemstone

Figure 2:
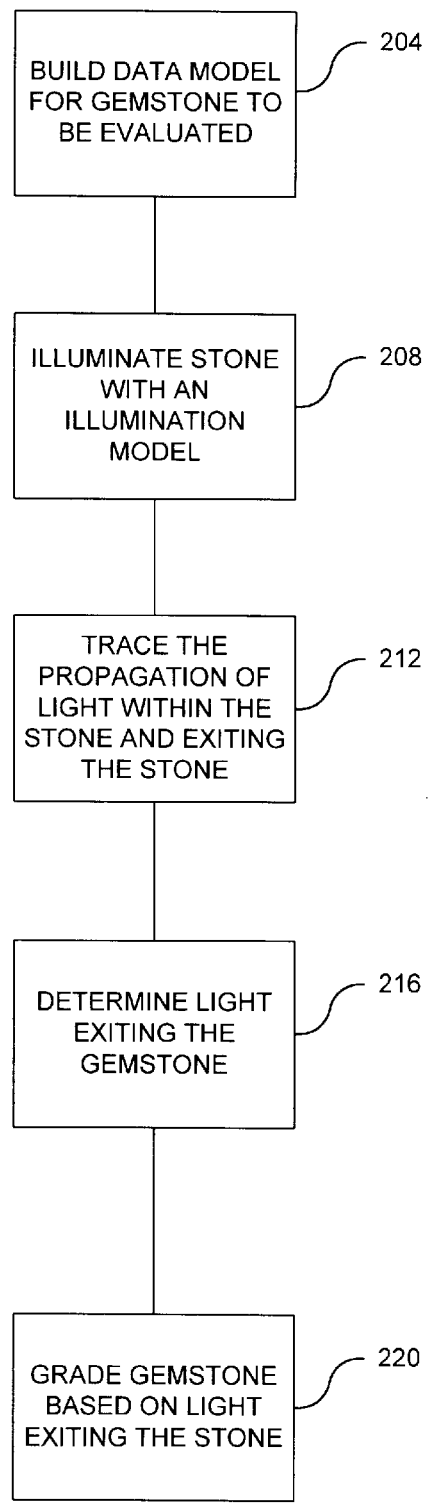
FIG. 2 is an operational flow diagram illustrating a process for evaluating a gemstone according to one embodiment of the invention.

FIG. 2 is a flow chart illustrating a process for evaluating a gemstone according to one embodiment of the invention.

In a step 204, a model of the gemstone to be evaluated is constructed. This model describes the characteristics of the gemstone which are useful in tracing light beam propagation within the stone. The model can include data which describes the cut of the gemstone, as well as other physical characteristics of the material, such as dispersion.

Cut data can include parameters such as the type of cut (round, emerald, princess, etc.), the facet types (break, main, star, etc.), the number and location of the various facet types, and the dimensions of the stone. Cut proportion can be used to determine the physical locations of the facets.

The cut data can include data on an existing cut of an already-cut stone, or data on a proposed cut for a stone to be cut. Cut data can be obtained using a variety of techniques. For example, cut data can be entered by a user, read from a file or other memory or storage, or downloaded from another machine. For existing cuts, there are numerous existing automated techniques and devices for measuring the characteristics of a cut stone. One such device, for example, is the Sarin Diamensia measuring machine. Using a simple interface, data from such devices can be directly downloaded to the invention. Such downloaded data can be supplemented with additional data entered by the user.

One example of a physical characteristic of the gemstone used to model the propagation of light in the gemstone is dispersion. Physical characteristics can be entered by the user or stored in a file, table or other data record. In a preferred embodiment, there are a plurality of stored records for various types of materials. The user selects the type of stone from a menu screen and the physical characteristics for the material of that stone (e.g., diamond) are retrieved from memory.

In a step 208 the gemstone model is illuminated using an illumination model. The illumination model represents a set of one or more light sources used to model an illumination of the gemstone. In a preferred embodiment, the illumination model is comprised of a plurality of light sources arranged in an array uniformly over the crown of the stone. For example, for a round-cut stone, the illumination model in the preferred embodiment is comprised of a plurality of evenly-spaced light sources arranged in a hemispherical array about the crown.

Other illumination models having one or more light sources arranged in other configurations can be used in accordance with the invention. For example, if a stone is to be modeled in a particular environment having known lighting conditions (e.g., a room having a known number of lights of a given color at known locations, or in a particular setting which does not allow light to enter from certain angels), the illumination model can be set up to model this environment. Note that in this scenario, the position and distance of the light sources relative to the stone can be adjusted to model the stone at a particular orientation and location in the environment.

In a step 212 the light propagating through the gemstone is modeled. In this step, light entering the gemstone from the light sources in the illumination model is traced as it is refracted into the stone, reflected within the stone and ultimately refracted back out of the stone. More specifically, in one embodiment, each light beam entering each facet from each light source is traced through the stone. The path of each light beam is traced from the initial refraction into the stone, through the one or more reflections off of the facets inside the stone, and to the refraction out of the stone. In a preferred embodiment, the light beam is traced through each of it's subsequent reflections and refractions until the light energy in the beam is exhausted or sufficiently diminished such that it adds nothing significant to the outcome of the modeling process.

Finally, in a step 220 the gemstone is graded based on the attributes of the light refracted out of the stone, as determined by evaluating the modeling performed in step 216. In one embodiment, this is accomplished by positioning a set of one or more viewing positions to view the light exiting the stone. These viewing positions are referred to as "cameras." The light refracted out of the gemstone model and received by each camera is evaluated. The characteristics of the light "seen" by each camera are evaluated to determine the grade of the stone.

In one embodiment, the cameras are arranged in an array surrounding the stone. Because the light emanating from the crown of the stone is most important in evaluating a stone, the cameras are preferably arranged to view the light output from the crown.

Figure 3A:
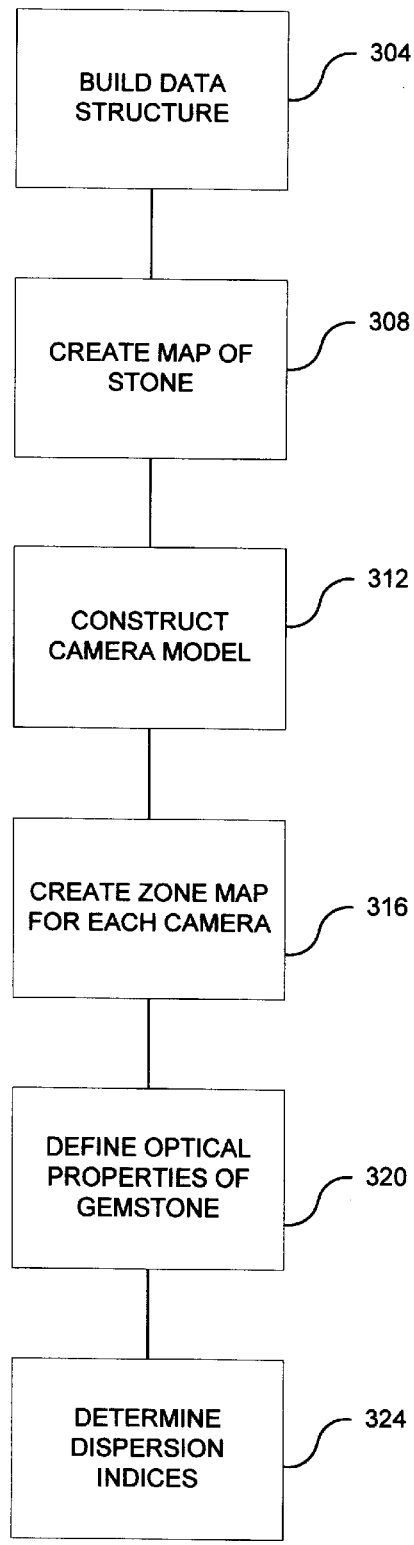
FIGS. 3(a) and 3(b) are an operational flow diagram illustrating an example process for evaluating and grading a gemstone according to one embodiment of the invention.
Figure 3B:
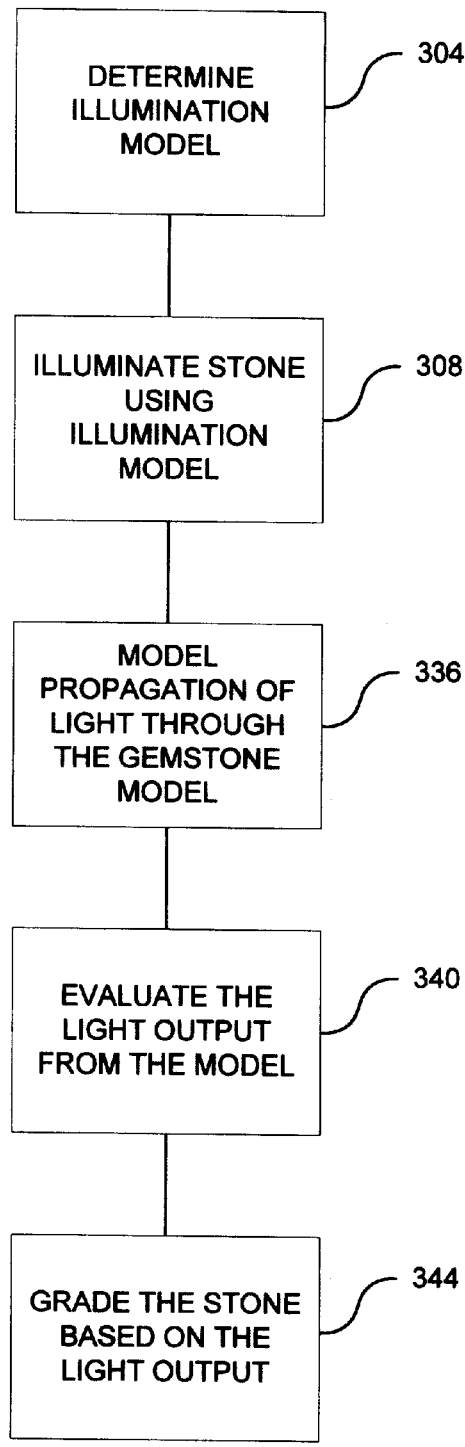

The general process of the invention as described above with reference to FIG. 2 is now described in more detail in accordance with a preferred embodiment of the invention. FIGS. 3(*a*) and 3(*b*) are operational flow diagram illustrating an example process for evaluating and grading a gemstone according to one embodiment of the invention. As with many of the operational flow diagrams in this document, the order in which the steps can be performed can be varied to a certain extent as would be apparent to one skilled in the art after reading this description.

In a step 304, a representation of the gemstone to be evaluated is built as a data structure. This data structure is an electronic representation of the stone to be evaluated. In a preferred embodiment, the data structure is a linked list of the facets of the gemstone. In one embodiment, each facet is described by the vertices of that facet in a global coordinate system.

Because the invention models light beams as they are reflected and refracted by the facets in the stone, the preferred data structure includes a definition for all facets in the stone, including the facets of both the crown and the pavilion. Note that in most instances, the girdle of the stone is unpolished, and therefore, energy striking the girdle is typically dissipated. Therefore, it is treated as a light sink by the model. Alternatively, for stones having a polished girdle, the girdle could be treated as a facet, and the girdle's contributions to reflection and refraction considered in the model.

In one implementation of the invention, the model of the gemstone is built using a CAD package, such as, for example, AutoCAD®. In this implementation, the CAD package provides a data structure which defines the facets in terms of their vertices. In this implementation, the model created and represented in the format of the CAD package is converted to a format which is usable by the evaluation software of the invention. In alternative embodiments, the original model is prepared using a custom modeling software such that this conversion is not necessary.

In a step 308 a map of the stone is created. The map created in this step is a map of the number and types of facets and their locations on the stone. Because the most important area of the stone from a grading perspective is typically the crown, in a preferred embodiment only the crown is mapped in step 308. Thus, in the preferred embodiment, the map created in step 308 is a map of the quantity and type of facets in various locations of the crown of the stone. This map is referred to as a master zone list.

In a step 312, a camera model of one or more cameras is constructed. In a preferred embodiment, an array of cameras is positioned about the crown of the stone to evaluate the light emitting from the crown in various directions. For example, for a round-cut stone, the preferred camera array is a hemispherical array of evenly spaced cameras positioned above the crown of the stone and "looking at" the stone. For other cuts, other camera configurations are implemented to provide a uniform view of the stone from various look angles.

Having a plurality of cameras in an array allows the stone to be "viewed" from several angles. As a result, the characteristics of the light emanating from the stone at various viewing angles can be evaluated. This is useful in determining the light output from the stone in each of these directions. For example, a round stone with too shallow a cut may produce a lot of light from the sides of the crown, and very little light from the table. For such a cut, a person looking at the stone from various viewing angles (i.e., from above the table, at an angle to the crown, etc.) would see varying degrees of light output at these different angles from different zones of the cut. Using numerous cameras looking at the stone from various different look angles allows such properties to be evaluated.

Thus, the camera model preferably includes the number of cameras and their positioning about the gemstone. In one embodiment, the camera locations are defined in terms of azimuth and elevation. For example, for a round gemstone, the camera locations can be described in terms of an azimuth angle around the gemstone and an elevation angle above the horizontal. These azimuth and elevation designations on the hemisphere of cameras can be thought of as latitude and longitude designations on a hemisphere of a globe.

Another way in which the camera locations are described is in terms of vertical arrays and resolution. For the hemispherical embodiment, each vertical array is analogous to a longitudinal line of the globe extending from a pole to the equator. The vertical resolution of cameras describes the number and spacing of cameras positioned along each longitudinal line. The horizontal resolution describes the number of vertical arrays around the hemisphere.

In a step 316, a copy of the map of the stone is created for each camera. Specifically, the map is recreated for each camera from the perspective of that camera. That is, the facet types are mapped to positions relative to the location of the camera. To help illustrate this point, consider a simple analogy to a map of the United States. The basic map of the United States shows each state and its position on the map. Now consider a viewpoint, or camera, positioned over the state of California. Depending on the height, or altitude of the camera, the states on the eastern seaboard may appear distant and their outlines may be skewed. This is especially true for a low camera height where the angle to the eastern to states is acute.

In a step 320, the optical properties of the material are defined. These can include properties such as the material's indices of refraction, dielectric constant, and other properties. These properties can be entered by the user. Alternatively, in one embodiment, these properties are stored in a file or data record and retrieved when needed. In one embodiment, the various materials are listed in a menu and the user simply selects the material to be evaluated and the properties for that material are retrieved.

In a step 324, the dispersion indices for the material are computed based on the optical properties of the material. The manner in which the dispersion indices are computed is described in detail below. In an alternative embodiment, the dispersion indices are precomputed for various materials and stored. In this embodiment, the dispersion indices are simply retrieved from storage.

In a step 328, the illumination model is determined. In the preferred embodiment, the illumination model is set up the same way the camera model is defined as described above. In other words, in this embodiment, the illumination model is comprised of a single light source, or a plurality of light sources arranged in an array around the gemstone. The lights can be arranged around and shining upon any selected portion of the stone. Thus, the stone can be evaluated in numerous simulated lighting conditions. For example, some settings do not allow light to enter the pavilion of the stone. To model the stone in this setting, no light sources are provided to illuminate the pavillion.

In a step 332, the model of the stone is illuminated using the illumination model determined in step 328. In a step 336, the light generated by the illumination model is modeled, or traced, as it is refracted into the stone, reflected within the stone, and refracted out of the stone. More specifically, according to a preferred embodiment, each beam of light refracted into the stone by a facet is traced as it is reflected within the stone and is refracted out of the stone by one or more facets.

In a step 340 the light refracted from the stone is evaluated. In a preferred embodiment, this step includes the step of measuring one or more attributes of the light exiting the various facets of the stone.

In a step 344, the results of the measurements made in step 340 are evaluated to determine a grade of the stone. For example, in one embodiment, several attributes are measured in step 340, including brilliance, scintillation and dispersion of the light exiting the stone. More particularly, in a preferred embodiment, these attributes are measured for light exiting each facet of the crown of the stone. In this embodiment, the values of these attributes for each facet are combined by some expression and the attributes are evaluated to determine a grade for the stone.

Figure 4:
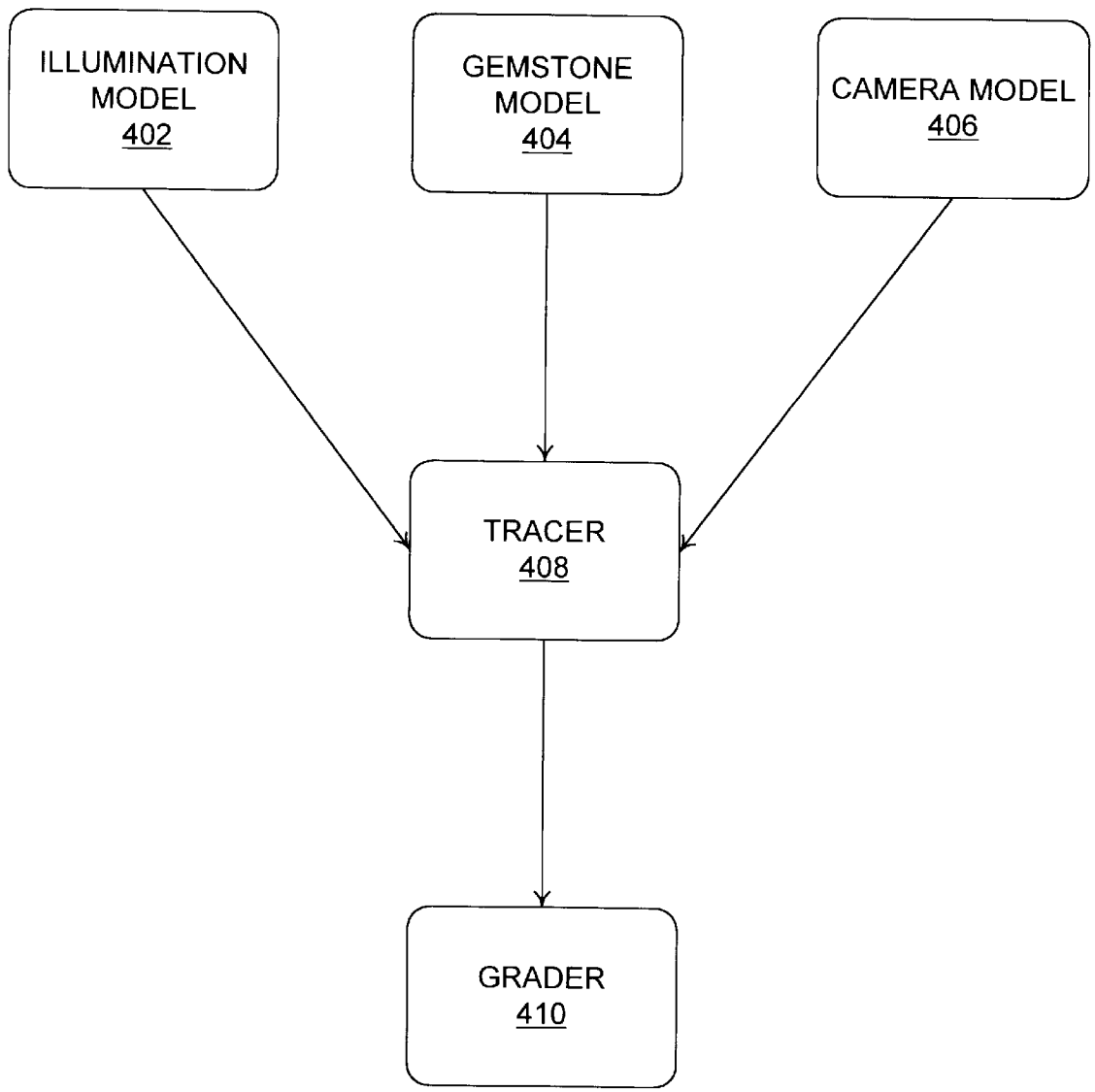
FIG. 4 is a block diagram illustrating an example architecture for the system according to one embodiment of the invention.

FIG. 4 is a functional block diagram of a gemstone evaluation system 400 according to a preferred embodiment of the present invention. System 400 includes an illumination model 402, a gemstone model 404, a camera model 406, a tracer 408, and a grader 410. Gemstone model 404 describes the physical characteristics of a gemstone to be evaluated. Illumination model 402 describes the light vectors to be used to stimulate gemstone model 404. Camera model 406 describes the data collection elements used to receive data describing light refracted by the gemstone model.

Tracer 408 is the simulation engine that receives incoming light vectors from illumination model 402, refracts the light described by these vectors into gemstone model 404, propagates that refracted light within the gemstone model 404 through reflections with the gemstone model facets, refracts light out of gemstone model 404, and captures that refracted light using the cameras defined by camera model 406.

The data collected by the cameras is evaluated by grader 410. This data contains one or more measurements of the light captured by the cameras. Grader 410 processes the camera data to determine one or more constituent grades and a composite grade for the gemstone.

5.0 Creating a Gemstone Model

According to a preferred embodiment, the invention utilizes a tracer to trace the propagation of one or more beams of light through a gemstone. In this embodiment, the tracer of the present invention can operate upon a computer model of the gemstone to trace the light through the model. In a preferred embodiment, the model is stored as a collection of facet descriptions. One example of such a facet data structure is described in detail below.

As described above, data describing the geometry of the gemstone may be generated by many sources in many different formats. In one embodiment, data describing the gemstone is developed within a computer-aided design (CAD) application, such as, for example, AutoCAD®. It is useful to convert this AutoCAD® data into a format suitable for modeling, or tracing, the propagation of light within the gemstone model. In a preferred embodiment, the geometry of the gemstone is defined such that it is described by a lined list of facet descriptors.

Figure 5:
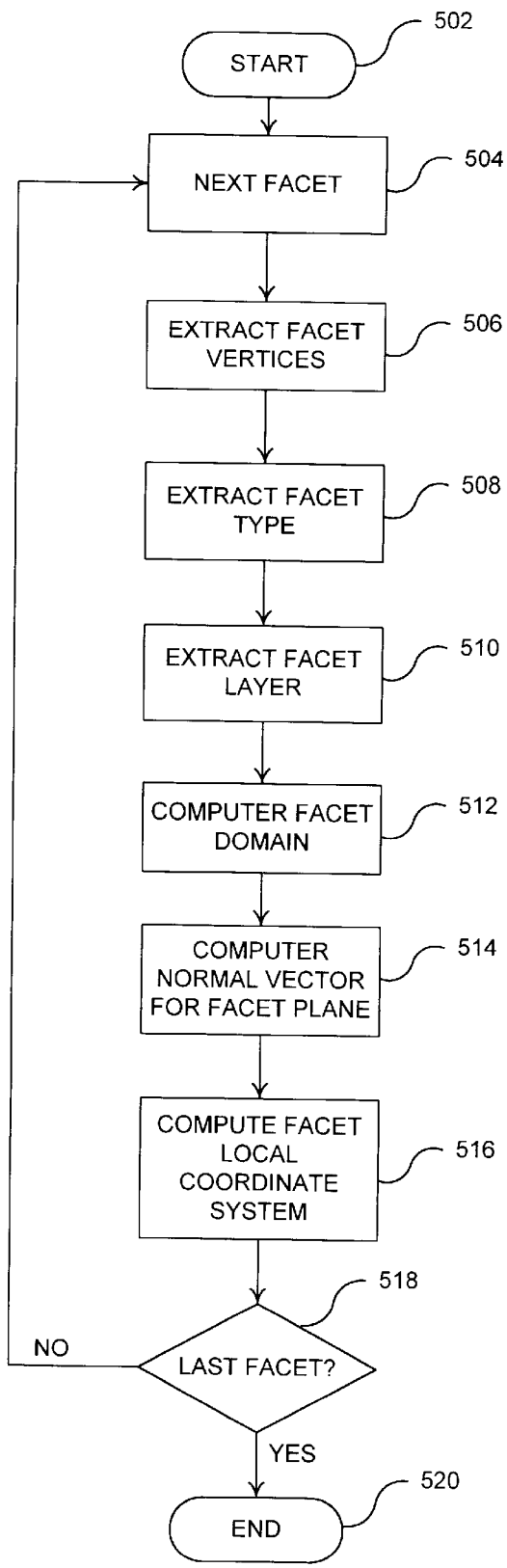
FIG. 5 is an operational flow diagram depicting one process for performing facet extraction according to a preferred embodiment of the present invention.

In a preferred embodiment, the conversion of gemstone geometry data to a set of facet descriptors occurs one facet at a time. This process is referred to as "facet extraction." FIG. 5 is a flowchart depicting one process for performing facet extraction according to a preferred embodiment of the present invention. This process is an example of one way in which step 304 of FIG. 3(a) can be carried out.

Referring to FIG. 5, according to this process, a facet is selected for extraction in a step 504. In a step 506, the vertices of the selected facet are extracted. For ease of data manipulation, it is preferable that each vertex is stored in Cartesian coordinates in a global coordinate system for the gemstone.

In a preferred embodiment, each facet is extracted from a data structure generated by AutoCAD®. AutoCAD® stores facets in two different ways, depending upon the number of vertices in the facet. If the number of vertices in a facet is less than five, AutoCAD® stores the facet as a single "3DFACE" data structure. If a facet has more than four vertices, it is stored as a linked list of "POLYLINE" data structures. The extraction methods for these two data structure types differ slightly, as would be apparent to one skilled in the relevant art. It is not necessary that the data structure be generated using AutoCAD®. In alternative embodiments, other software packages or custom software can be used to define the data structure. In such embodiments, the extraction step may be implemented differently, or may not be needed at all, depending on the data structure.

Also, in the preferred embodiment, the facet type is extracted, as shown in a step 508. The facet type is a gemmological classification of the type of facet (for example, break, main, star, table, etc.). In the preferred embodiment, the "facet layer" is extracted, as shown in a step 510. The facet layer is a gemmological classification of the gemstone layer in which the facet lies (for example, girdle, crown, pavilion).

In a step 512, the "facet domain" is calculated. The facet domain is a rectangle circumscribing the facet in the facet plane. The rectangle is formed by taking the minimum and maximum x, y and z global coordinates of the facet vertices and using these values to define the sides of the rectangle.

In a preferred embodiment, the gemstone model represents the geometry of each facet by its vertices and the coefficients of the equation describing the normal line for the plane of the facet. In a step 514, the normal line for the facet plane is computed using three of the facet vertices. In one embodiment, if less than 3 vertices are available for the facet, the facet is discarded as spurious.

In a preferred embodiment, the three facet vertices chosen are used to form two vectors in the global coordinate system. The normal vector for the plane is found by taking the cross-product of these two vectors. The equation for a line in 3D Cartesian coordinate space is $Ax+By+Cz+D=0$. Therefore, the coefficients stored are A, B, C, and D.

In order to speed and simplify reflection and refraction calculations, in a preferred embodiment, a local coordinate system is established for each facet, as shown in a step 516.

In a preferred embodiment, the z-axis of the facet local coordinate system is chosen as the normal line for the facet plane, with increasing values of z toward the center of the gemstone. Preferably, the origin of the local coordinate system is chosen to be a vertex of the facet, such as, for example, the first vertex in the linked list of vertices describing the facet. Additionally, in a preferred embodiment, the x-axis intersects the first and second vertices. The y-axis is defined with respect to the z- and x-axes.

Each facet is extracted in a similar manner, as shown in a step 518. When all of the facets for the gemstone have been extracted, the geometric gemstone model is complete.

6.0 Build Master Zone List

As briefly introduced above, in one embodiment, a plurality of virtual cameras are used to measure the attributes of the light exiting the stone. In one embodiment, the cameras measure the light exiting the stone from various areas of the stone. In a preferred embodiment of the present invention, each camera measures the light refracted by each facet of the stone separately. Therefore, in this embodiment, each camera contains a camera-unique data structure for each facet to be examined. These data structures are referred to as "zones." A particular zone for a particular camera can contain some data that is particular to that camera, and some data that is common to all cameras for that particular zone.

To enhance processing efficiency, in a preferred embodiment, a master zone list is built and populated with the common data, and then copied to each camera, for populating with zone data particular to each camera. An example "zone" data structure is described in detail below.

Figure 6:
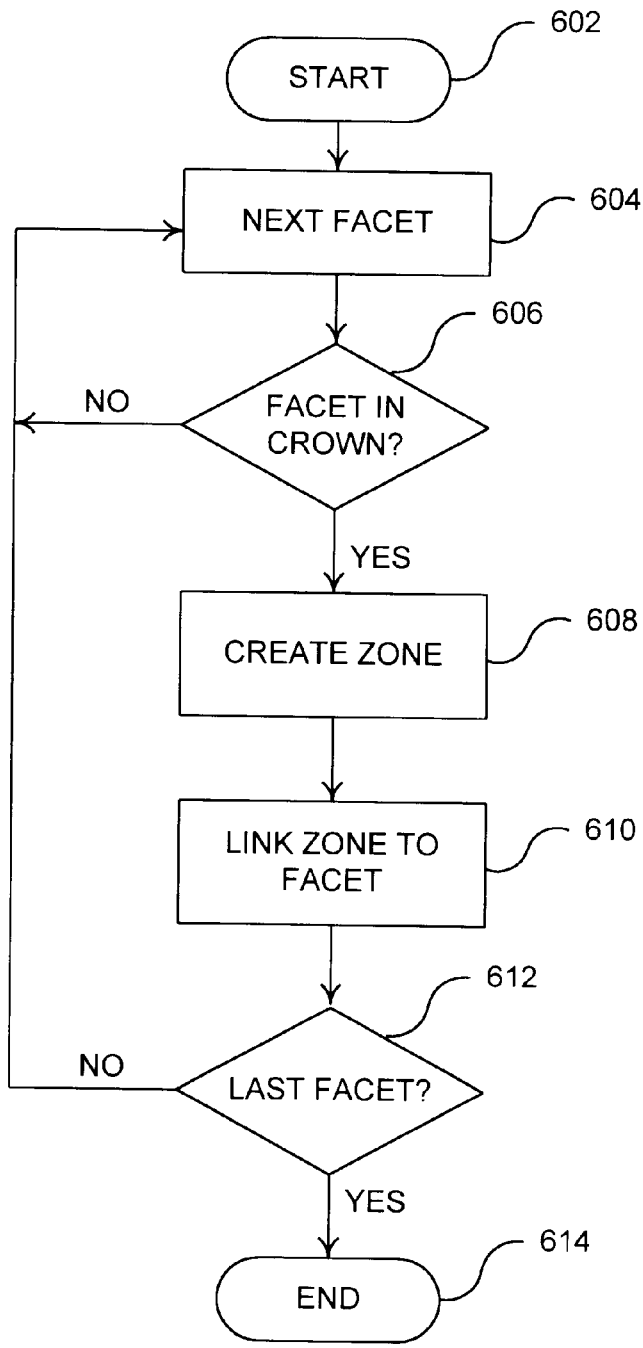
FIG. 6 is a flowchart illustrating one example process for building a master zone list according to a preferred embodiment of the invention.

FIG. 6 is a flowchart illustrating one example process for building a master zone list according to a preferred embodiment of the invention. This illustrates one process for implementing step 308 of FIG. 3(a). The master zone list contains one zone for each facet from which refracted light will be measured.

In a step 604, one gemstone facet is selected for the creation of one corresponding zone in the master zone list.

In a preferred embodiment of the present invention, only facets located in the crown layer of the gemstone are measured for refracted light. Therefore, if the selected facet is not in the crown layer, as indicated by the "no" branch from step 606, another facet is selected for processing. Processing of facets in different layers, different combinations of layers, or all layers, is within the spirit and scope of the present invention, as would be apparent to one skilled in the relevant art after reading this disclosure.

If the facet is in the crown layer, as indicated by the "yes" branch from step 606, then a zone is created for that facet, as shown in a step 608. Then, in a step 610, the newly-created zone is linked to its corresponding facet. This linking allows a zone to be processed using its corresponding facet's data, without replicating that data. This is one benefit of the linked list structure and pointing to the facet.

Each crown facet is processed in a similar manner, as shown in a step 612. When all of the crown facets have been processed, the master zone list is complete.

7.0 Construct Camera Model

When light exits the gemstone model through refraction, data describing the refracted light is captured for evaluation to produce a cut grade for the gemstone. In a preferred embodiment of the present invention, one or more data collection elements, called "cameras," are provided. The size, location and orientation of the cameras affect the measurement of the refracted light. In a preferred embodiment, these parameters are user-selectable.

Figure 7:
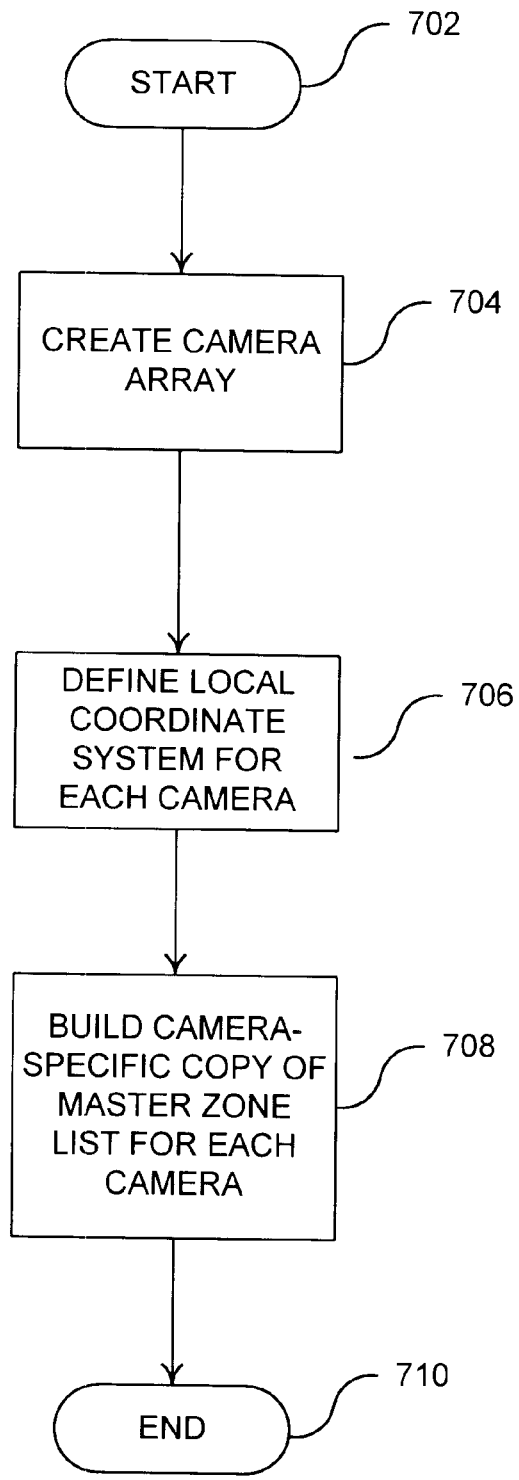
FIG. 7 is a flowchart illustrating an example process for creating a camera model according to one embodiment of the invention.

FIG. 7 is a flowchart illustrating an example process for creating a camera model. This example process can be used to implement step 312 of FIG. 3(a). In a step 704, user-selectable parameters are used to create an array of cameras. To simplify the capture of refracted light data, a local coordinate system is established for each camera, as shown in a step 706.

As described above, a master zone list is created to capture gemstone data common to all cameras. Once the camera array has been defined, a copy of the master zone list is allocated to each camera for capturing zone data specific to that camera, as shown in a step 708.

As described below, each camera collects data for each visible facet separately through the use of zones. Each measurement of facet flux accounts for the surface area of the facet by computing a flux density for the facet. Therefore, the use of camera zones permits an accurate measure of the composite flux density for the entire gemstone. Measurement techniques that do not account for the individual effect of each facet's surface area would be unduly influenced by the total flux for the gemstone, and thus produce an inconsistent grade.

For example, a shallow-cut stone may have a higher total flux than an ideal cut, but a lower composite flux density. The result is that a shallow-cut stone refracts little light out through its table facet, presenting a dark appearance referred to as "fish-eye." A technique that did not account for the effects of each facet's surface area would erroneously assign the shallow-cut stone a higher brilliance grade than the ideal stone. Because the present invention measures flux density for each facet, the ideal stone would correctly receive a higher brilliance grade.

7.1 Create Camera Array

In a preferred embodiment of the invention, each camera is represented by a bounded plane, and the cameras are arranged in a hemispherical array surrounding the crown of the gemstone. Other camera shapes, orientations and locations can be used without departing from the spirit and scope of the present invention, as would be apparent to one skilled in the relevant art.

Figure 8:
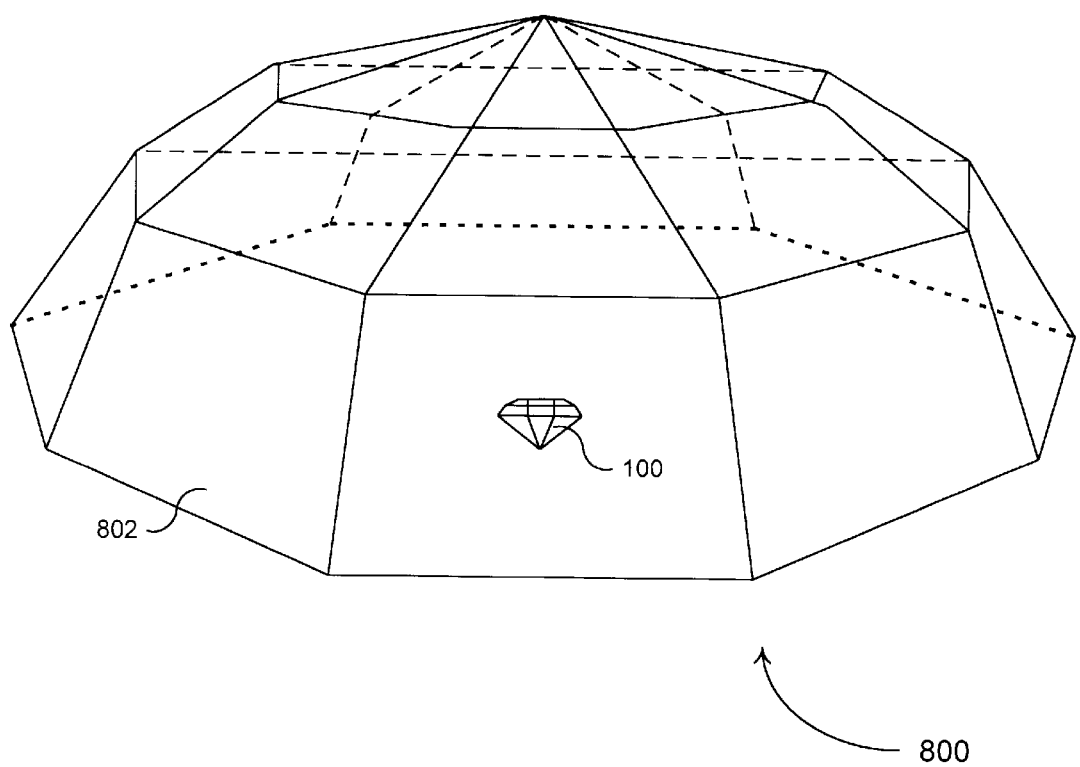
FIG. 8 depicts an example arrangement of cameras according to one embodiment of the present invention.

FIG. 8 depicts an arrangement of cameras according to one embodiment of the present invention. In the depicted embodiment, 24 cameras 802 are arranged in an array 800 surrounding gemstone 100. Hemispherical array 800 is defined by several user-selectable parameters. The "viewing distance" describes the distance from the "camera insertion point" to the center of each camera lens. In a preferred embodiment, the camera insertion point is selected as the origin of the global coordinate system.

The size of each camera lens is selected in terms of its angular size in azimuth and elevation, as seen from the camera insertion point. In a preferred embodiment, each camera has the same angular dimension. The angular size of each camera in azimuth is referred to as the "horizontal resolution." The angular size of each camera in elevation is referred to as the "vertical resolution." In the example camera array 800 depicted in FIG. 8, the horizontal resolution is 45° and the vertical resolution is 30°.

In a preferred embodiment, the maximum angular extent in elevation of the camera array can be selected. This quantity is referred to as the "maximum vertical angle." The maximum extent of the camera array in azimuth can also be specified. This quantity is referred to as the "maximum horizontal angle." In the example camera array 800 depicted in FIG. 8, the maximum horizontal angle is 360° and the maximum vertical angle is 90°.

In a preferred embodiment of the present invention, the cameras are is permitted to overlap. The effect of the overlap is to provide each camera with a second, larger "lens." The angular extent of this second lens in azimuth and elevation is referred to as its "horizontal overlap" and "vertical overlap." No vertical overlap is permitted beyond 90° elevation.

7.2 Define Camera Local Coordinate Systems

In a preferred embodiment, the local coordinate system of each camera is created by transforming the global coordinate system. The origin of the camera local coordinate system lies at the camera insertion point. The z-axis is normal to the plane of the camera, and the negative z-axis passes through the angular center point of the camera. The x- and y-axes lie in the plane of the camera.

7.3 Build Camera Zone Lists

As described above, a copy of the master zone list containing data common to all cameras is allocated to each camera. Each camera's copy is then populated with camera-specific data to prepare the camera to receive data describing refracted light.

Figure 9:
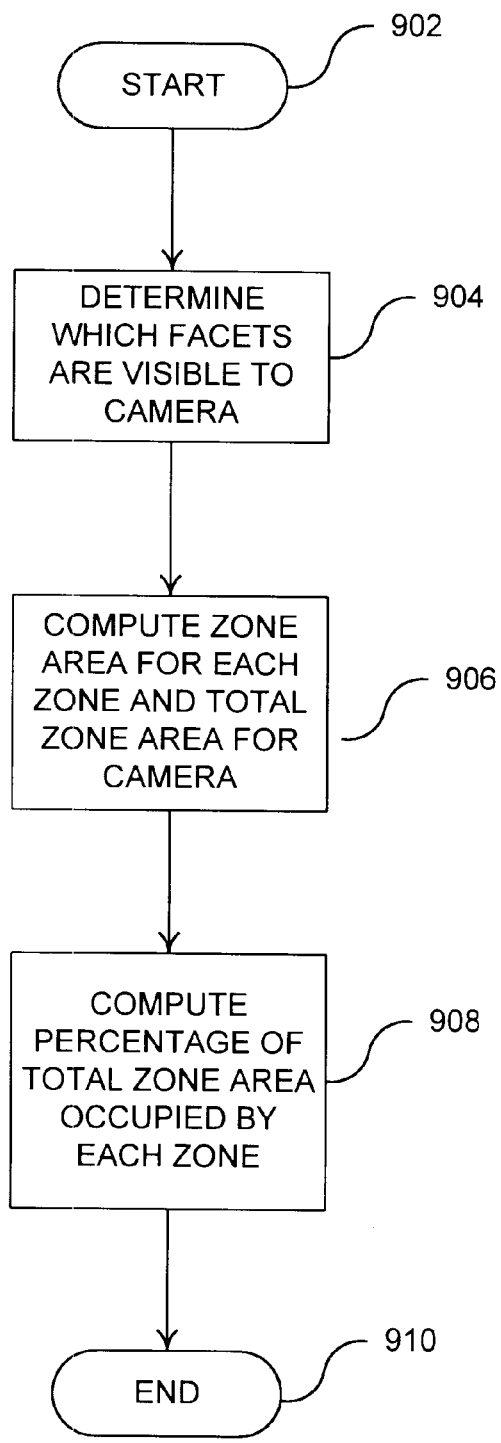
FIG. 9 is a flowchart depicting an example process for building a camera-specific copy of the master zone list for a camera according to one embodiment of the invention.

FIG. 9 is a flowchart depicting an example process for building a camera-specific copy of the master zone list for a camera. This process illustrates one manner in which step 708 of FIG. 7 can be performed.

In a step 904, each camera zone is examined to determine whether the corresponding facet is visible to the camera. In a preferred embodiment, this determination is made by comparing the z coordinates of the camera center point and the "pass-through point" of the facet plane. The pass-through point is computed by substituting the coordinates of the camera location into the equation for the plane of the facet and solving for the new z coordinate. As described above, the camera location is the point in the camera plane at the angular center of the camera.

The comparison of the pass-through point to the camera location differs, depending on whether the selected facet is above or below the girdle of the gemstone. If the selected facet is above the girdle, then a pass-through point having a greater z coordinate than that of the camera's center indicates that the selected facet is visible to the camera. If the selected facet is below the gemstone girdle, then the camera location having a z coordinate greater than that of the pass-through point indicates that the facet is visible. An indication of the zone's visibility to the camera is stored as part of the zone description.

In a step 906, the zone area for each zone is computed, and the zone areas for all of the camera zones are totaled to create a total zone area for the camera. The zone area for a zone is computed by projecting the corresponding facet onto the plane of the camera. The area of the projection is the zone area for the zone corresponding to the facet. In a step 908, the percentage of the total zone area occupied by each zone is computed. Once the camera-specific copies of the master zone list have been built for each camera, the camera array is ready to capture data describing light refracted from the gemstone.

8.0 Determine Illumination Model

To stimulate the gemstone model, an illumination model is constructed. An illumination model includes one or more illumination vectors (also referred to as "light vectors") of a predetermined intensity.

In a preferred embodiment of the present invention, the incident intensity of each illumination vector is selected as one Watt per square meter. Each illumination vector is used to project each facet into the gemstone, thereby creating beams of refracted light. Each beam propagated within the gemstone has an associated cross-sectional intensity. When a beam is refracted out of a gemstone facet, the cross-sectional intensity of the beam and the area of the portion of the refracting facet illuminated by the refracting beam (as perceived by the camera capturing the refracted light) are used to determine the extant flux of the refracting light.

Each time a parent beam strikes a facet, the cross-sectional intensity of the resulting reflected child beams (reflected and refracted, if any) is derived from the cross-sectional intensity of the parent beam. The flux of any refracted beam is determined by the camera capturing the refracting beam by multiplying the cross-sectional intensity of the refracted beam by the area of the facet illuminated by refraction perceived by that camera, based on the relative orientations of the camera and facet, as described below. Other methods of tracking beam energy through the gemstone can be employed without departing from the spirit and scope of the present invention, as would be apparent to one skilled in the relevant art.

In a preferred embodiment of the invention, one of two illumination models can be selected: spherical diffuse or conicular. Other illumination models can be employed without departing from the spirit and scope of the present invention, as would be apparent to one skilled in the relevant art.

Figure 10:
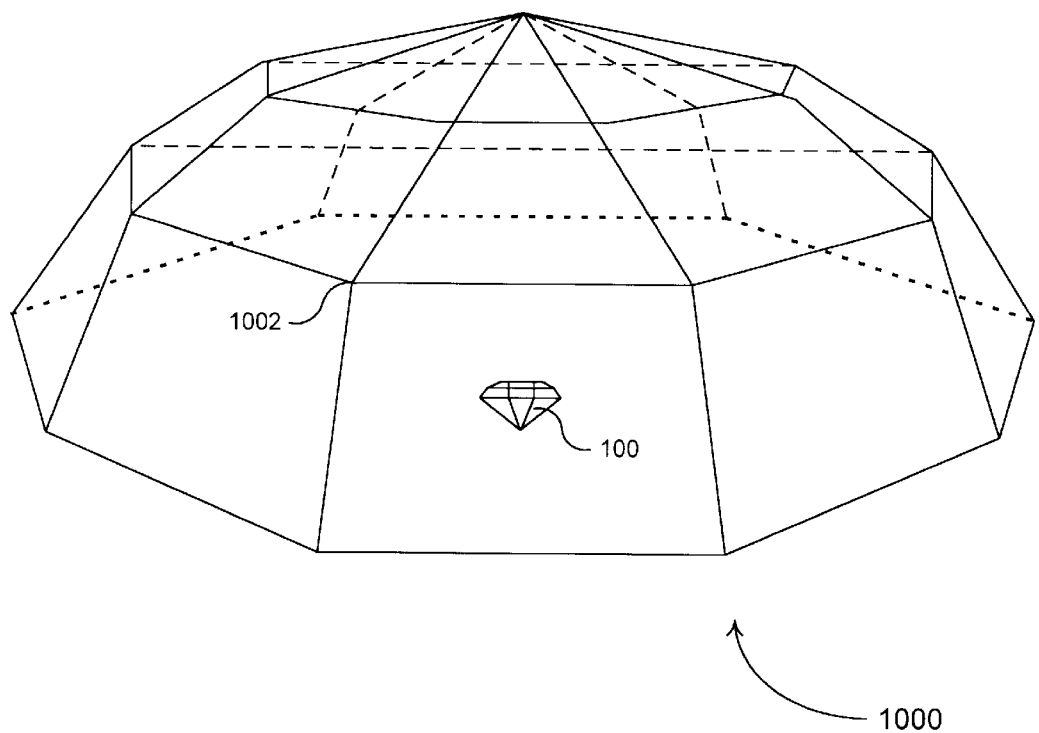
FIG. 10 depicts an example spherical diffuse illumination model.

The spherical diffuse model is an hemispherical array of point light sources arranged about the crown of the gemstone. The locations of these point sources are defined by user-specified parameters which are similar to those for the definition of the camera model. FIG. 10 depicts a typical spherical diffuse illumination model.

The location of each light source in the spherical diffuse illumination model is selected in terms of its angular location in azimuth and elevation, as seen from the global origin. In a preferred embodiment all adjacent light sources are separated by a selected elevation angle (termed the "vertical resolution" for the illumination model) and a selected azimuth angle (termed the "horizontal resolution" for the illumination model). In the example spherical diffuse lighting array 1000 depicted in FIG. 10, the horizontal resolution is 45° and the vertical resolution is 30°

In a preferred embodiment, the maximum angular extent in elevation of the lighting array can be selected. This quantity is referred to as the "maximum vertical angle" for the illumination model. The maximum extent of the lighting array in azimuth can also be specified. This quantity is referred to as the "maximum horizontal angle" for the illumination model. In the example spherical diffuse lighting array 1000 depicted in FIG. 10, the maximum horizontal angle is 360° and the maximum vertical angle is 90°. Once the lighting array is constructed, an illumination vector is created for each light source in the array. Each light vector originates at the light source and terminates at the global origin.

While the spherical diffuse illumination model is independent of the arrangements of the facets, the conicular model is defined in terms relative to each individual facet. The conicular illumination model defines a number of light rays evenly spaced about the surfaces of a number of cones of varying cone angles centered on the normal line of the facet plane.

Figure 11:
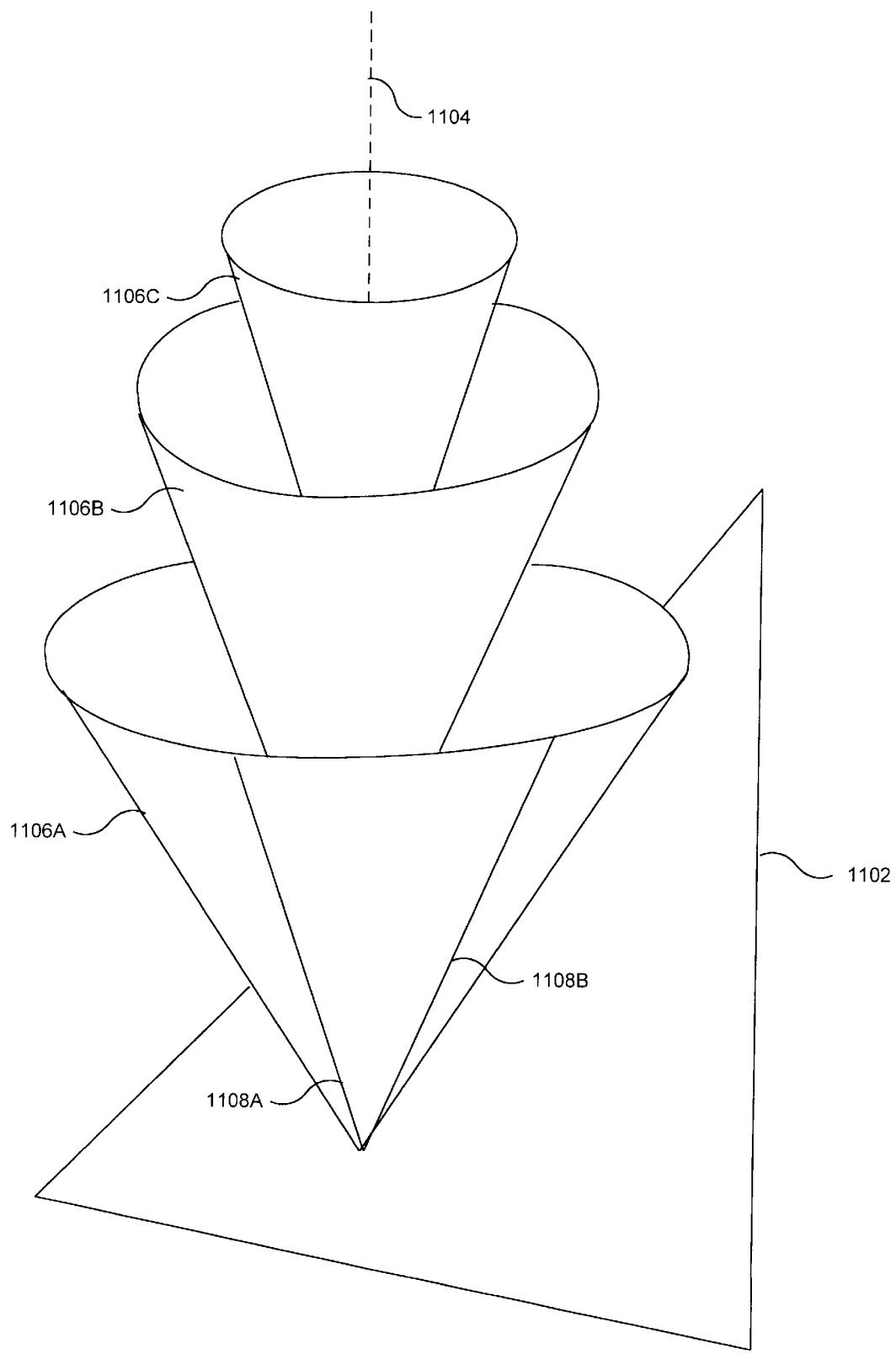
FIG. 11 depicts an example conicular illumination model.

FIG. 11 depicts a typical conicular illumination model. The conicular illumination model is defined with respect to normal line 1104 of facet 1102. A number of cones 1106 are defined at regular cone angles from normal line 1104. A number of illumination vectors are disposed upon the surface of each cone at regular intervals, pointing toward the center of the gemstone and meeting at the facet plane 1108. Because the conicular illumination model is oriented with respect to the orientation of a facet, new conicular illumination model is generated each time a new facet is selected for illumination.

9.0 Compute Dispersion Indices for Gemstone Material

In one embodiment of the present invention, not only is "white" light propagated through the gemstone along the light beam's Pointing vector, but also dispersion components are propagated as well. In the preferred embodiment, each of seven dispersion components is propagated through the gemstone. These dispersion components are of different wavelengths from the "white" light, and therefore will propagate in slightly different angular directions with respect to the "white" beam component, based on their respective indices of refraction. These indices are dependent upon the gemstone material.

Figure 12:
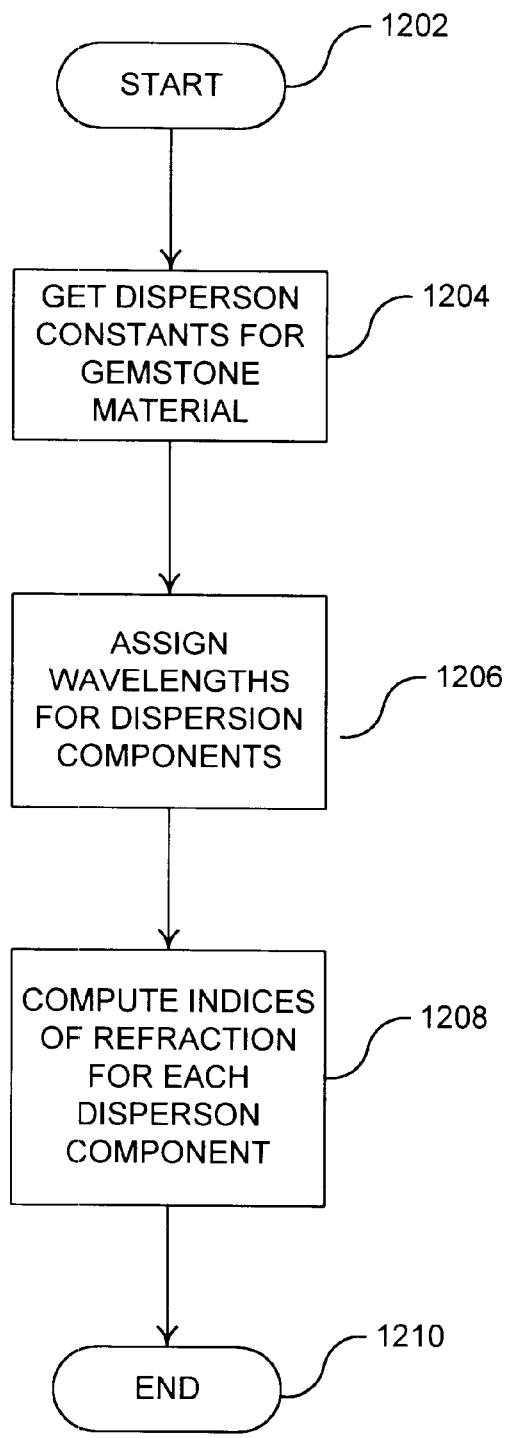
FIG. 12 is a flowchart depicting one process for computing the indices of refraction for various dispersion components according to a preferred embodiment of the invention.

FIG. 12 is a flowchart depicting one process for computing the indices of refraction for various dispersion components according to a preferred embodiment of the invention. This process described with reference to FIG. 12 is one process by which step 324 of FIG. 3(*a*) can be implemented.

The optical properties of any gemstone material can be characterized by its dispersion constants. Therefore, in a step 1204, the dispersion constants for the gemstone material in question are obtained. These data may be obtained from a computer file or table, or directly from the user through interface prompts. In a preferred embodiment, these constants include two wavelength constants ($\lambda_1$ and $\lambda_2$) and two dielectric constants corresponding respectively to the wavelength constants. ($C_1$ and $C_2$). Exemplary constants for diamond gemstone material are given by A. Manewood in "PROPERTIES AND GROWTH OF DIAMOND," edited by Gordon Davies, King's College, London, UK, 1994. These constants are given below.

$C_1$=0.3306
$C_2$=4.3356
$\lambda_1$=175
$\lambda_2$=106

Next, the dispersion components are defined by assigning minimum, maximum, and average wavelengths to each, as shown in a step 1206. Finally, the indices of refraction for each dispersion component are computed using equation 12.F1, given below.

$$n(\lambda) = \sqrt{\frac{c_1 \lambda^2}{\lambda^2 - \lambda_1^2} + \frac{C_2 \lambda^2}{\lambda^2 - \lambda_2^2} + 1}$$

For each dispersion component, the maximum wavelength is used to calculate the maximum index of refraction, the minimum wavelength is used to calculate the minimum index of refraction, and the average wavelength is used to calculate the average index of refraction. In a preferred embodiment, the data describing each dispersion component is stored in a data structure in a linked list. An exemplary data structure, entitled, "dispbuf," is outlined and described below.

10.0 Illuminate the Gemstone Model

FIGS. 13(*a*) and 13(*b*) are a flowchart describing an example process for illuminating a gemstone model according to one embodiment of the invention. This example process is one way in which step 332 of FIG. 13(*b*) can be implemented.

In a preferred embodiment, the present invention allows the user to specify one of two modes of operation: "single" and "automatic." In the "automatic" mode, the grade of the gemstone is based on illumination of every facet in the gemstone. In the "single" mode, the gemstone grade is based on the illumination of only one user-specified facet. In alternative embodiments, other modes are contemplated. For example, in an alternative embodiment, the evaluation of the stone can be based on a defined set of a plurality of facets.

Figure 13A:
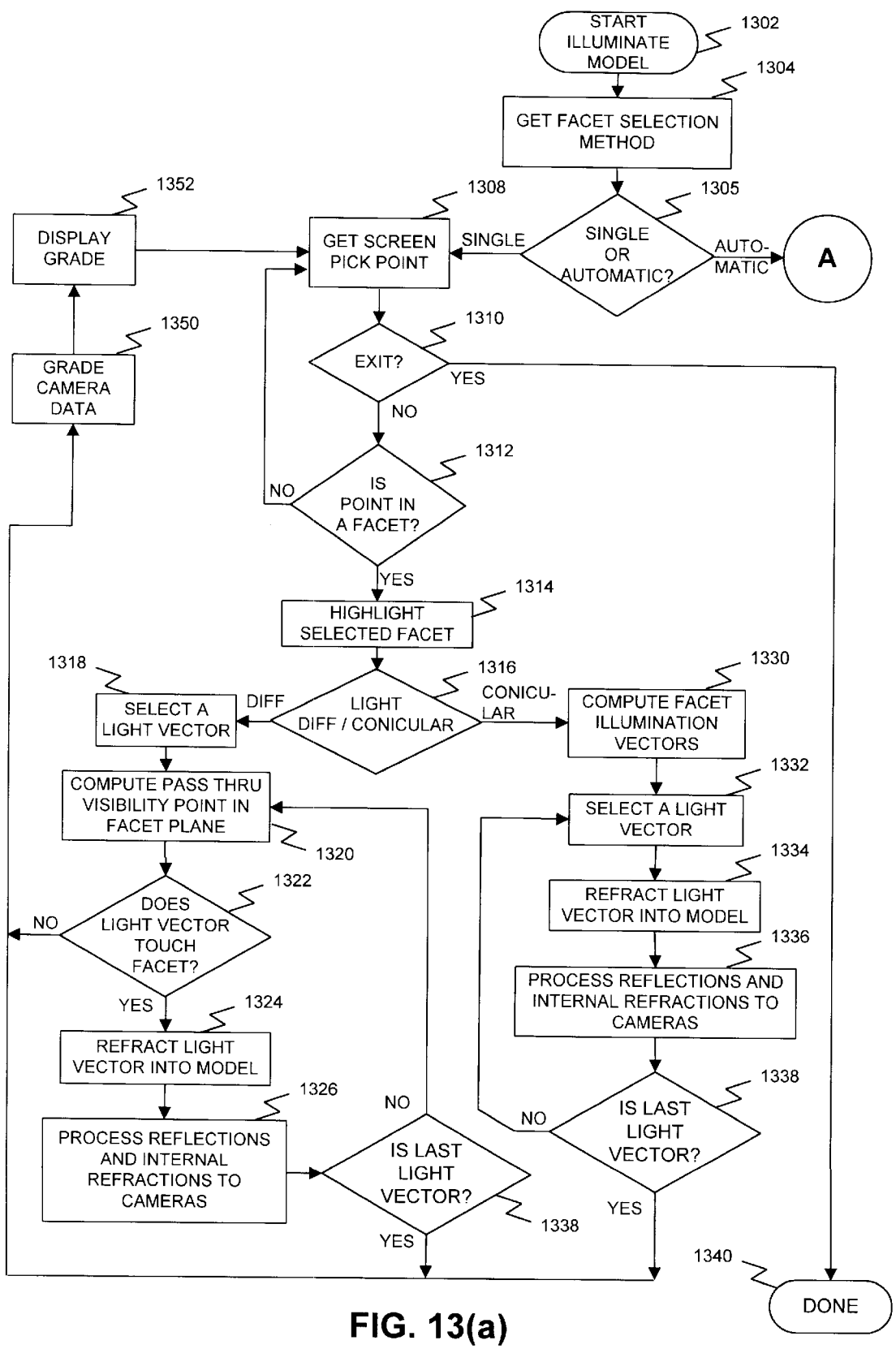
FIGS. 13(a) and 13(b) are a flowchart describing an example process for illuminating a gemstone model according to one embodiment of the invention.

Referring to FIG. 13(a), the user specifies one of the two facet selection methods, as shown in a step 1304. If the user selects the single mode of facet selection, as shown by the "single" arrow from step 1306, then the user is prompted to select a facet, as shown in a step 1308. If the user wishes to quit the routine, the user can respond by either exiting the routine or by selecting a point on the screen. If the user decides to exit the routine, as shown by the "yes" arrow from step 1310, then processing exits the illumination loop, as shown in a step 1340.

Alternatively, if the user has selected a point on the screen, then that point must be examined to determine whether it lies in a facet of the gemstone. If not, as shown by the "no" arrow from step 1312, then the user is again prompted to pick a screen point, as shown in a step 1308. Alternatively, if the user has selected a facet in the gemstone, as shown by the "yes" arrow from step 1312, then the selected facet is highlighted on the display to inform the user that he has made a valid selection, as shown in a step 1314.

Processing then diverges based on the illumination model selected by the user, as shown in a step 1316. As described above, in the preferred embodiment, the light vectors in the circular illumination model are calculated based on the normal vector of the facet illuminated. Therefore, in this embodiment, the illumination vectors are computed after the facet is selected. Thus, the facet illumination vectors for the circular illumination model are calculated in a step 1330.

The selected facet is then sequentially illuminated by each illumination vector. For each illumination vector, a light beam is created into the gemstone as a result of a refraction of the original light beam by the illuminated facet. This light beam is then propagated through various reflections within the gemstone until light eventually exits the gemstone through a refraction. Data describing the light exiting the gemstone is then collected for processing by the cameras. In one embodiment, where process limits are employed, data is only collected until the energy in the beam is exhausted, or sufficiently close to zero. Then, another illumination vector is selected for processing. This process continues until all illumination vectors have been processed for the selected facet.

First, one of the illumination vectors generated is selected, as shown in a step 1332. Next, the selected illumination vector is refracted into the gemstone model, thereby creating a light beam within the gemstone model, as shown in a step 1334. This light beam is then propagated through reflections within the gemstone. If the light beam strikes a facet of the gemstone at less than the critical angle of the gemstone material, then some of the light will exit the gemstone through refraction. Data describing this refracted light beam is captured for processing by the cameras to obtain a gemstone grade. See step 1336.

Each light vector is sequentially processed in this manner. When the last light vector has been processed for the selected facet, as shown by the "yes" arrow from step 1338, the data collected by the cameras is used to grade the gemstone, as shown in a step 1350, and the grade is displayed to the user, as shown in a step 1352. The user is then prompted to select another facet, as shown in a step 1308.

If the diffuse illumination model has been selected, the orientation of the illumination vectors is independent of the orientation of the facets selected for processing. Illumination vectors for the diffuse illumination model can be generated when that model is selected, as described above, and need not be regenerated once a facet is selected for processing. For the same reason, however, each illumination vector should be checked to determine whether it strikes the facet selected for processing. If it does strike the facet, then the light vector is propagated within the gemstone, and data regarding the light exiting the gemstone is captured for processing by the cameras, as described above.

For the diffuse illumination model, an illumination vector is selected, as shown in a step 1318. To determine whether the selected illumination vector strikes the selected facet, the pass-through visibility point in the plane of the selected facet is computed, as shown in a step 1320. The pass-through visibility point is completed as described above with respect to the camera zone list.

If the selected illumination vector does not strike the selected facet, as shown by the "no" arrow from step 1322, then the user is prompted to select another facet, as shown in a step 1308. Alternatively, if the selected illumination vector strikes the selected facet, as shown by the "yes" arrow from 1322, then the illumination vector is propagated through the gemstone, as described with respect to steps 1334 and 1336, as shown in steps 1324 and 1326. When the last light vector has been processed, the data collected by the cameras is used to grade the gemstone, as shown in a step 1350, and the grade is displayed to the user, as shown in a step 1352. The user is then prompted to select another facet, as shown instep 1308.

Alternatively, the user may select the "automatic" facet selection mode, as shown by the "automatic" arrow from step 1305. If so, then each facet in the gemstone is processed as described above for a single facet in the "single" facet selection mode, and the gemstone grade is based on data generated by all of the gemstone facets. In one embodiment of the present invention, every facet in the gemstone is illuminated, and data is collected for light exiting every facet in the gemstone. In another embodiment, only facets in the crown are illuminated, and only light exiting crown facets is considered in determining the grade. In another embodiment, every facet in the gem is illuminated, and only light exiting crown facets is considered for the grade. In yet another embodiment, only crown facets are illuminated, and light exiting all facets of the gemstone are considered in determining the grade. Other such permutations and combinations are within the spirit and scope of the present invention, as would be apparent to one skilled in the relevant art after reading this description.

Figure 13B:
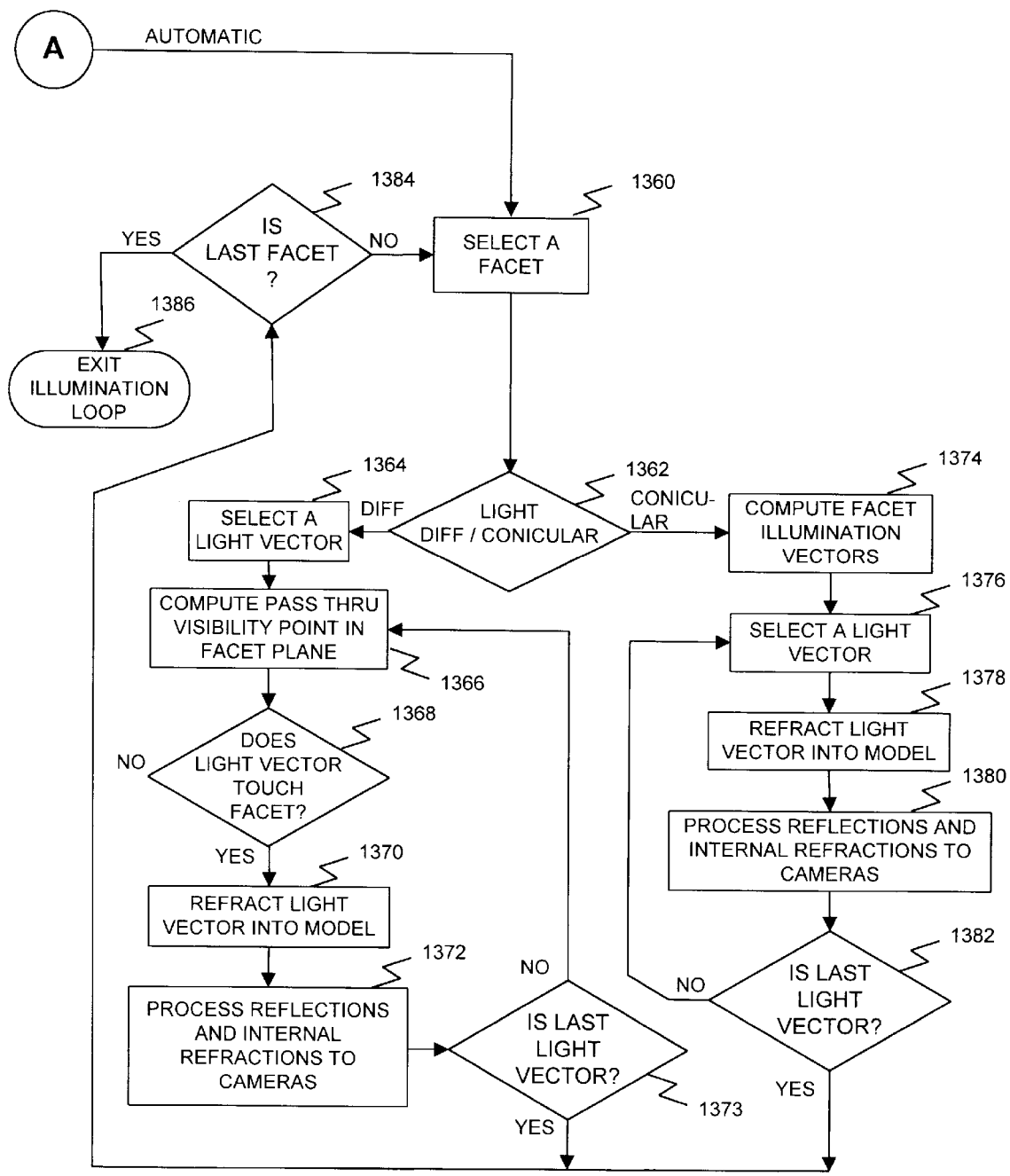

Referring to FIG. 13(b), if the "automatic" facet selection method is selected, then the first step is to select one of the gemstone facets for processing, as shown in a step 1360. The facet is then processed as described above in the "single" mode with respect to steps 1316 through 1338, as shown in corresponding steps 1362 through 1382.

If facets remain to be processed, as indicated by the "no" branch from step 1384, then a new facet is selected for processing, as shown in 1360. Alternatively, if no facets remain to be processed, as shown by the "yes" branch from step 1384, then processing exits the illumination loop, as shown in step 1386. Processing then resumes at step 220 in FIG. 2, where the data collected by the cameras is graded.

11.0 Example Data Structure for a Gemstone Model

Once a light vector and facet have been selected for processing, the light vector is "refracted" into the model to create a light beam. The data relating to the beam of light is tracked with that beam and updated as the beam is reflected in the stone. That is, as the properties of the beam of light change as the beam is reflected (e.g., resulting energy remaining in a reflected beam), this updated data is maintained for the beam. This section of the document describes an example data structure for storing data relating to the light beams propagated through the gemstone model.

In a preferred embodiment, the resulting data is stored in a data structure called "ltbeam" although other data structures can be implemented. This data structure implemented in the preferred embodiment describes the characteristics of the light beam at the surface of the refracting facet. This operation corresponds to steps 1324 and 1334 in FIG. 13(a), and to steps 1370 and 1380 in FIG. 13(b).

As light beams are propagated and reflected within the gemstone, a data structure is used to capture the data describing these light beams. This preferred data structure is now described. As described above, the light beam calculation proceeds bounce by bounce. Each light beam is described by a "ltbeam" data structure. When a parent light beam is reflected to create one or more child light beams, the data elements of the child light beam data structures are derived from the data elements of the parent light beam data structure. Once the child light beams are calculated, the parent light beam data structure can be released. Using this technique, light beam data structures are required simultaneously in a maximum of two generations of a beam. Previous light beam data structures can be released, resulting in a highly efficient memory resource allocation technique.

The preferred light beam data structure is presented below.

```
typedef struct ltbeam {
    struct ltbeam *next;
    struct facet *inface;
    struct facet *outface;
    struct facet *parent;
    struct resbuf *verts;
    struct resbuf *path;
    ads_real domain[3][2];
    ads_real dircos[8][3];
    ads_real index;
    ads_real area_r;
    ads_real area_x;
    ads_real xsec_intp;
    ads_real xsec_ints;
    ads_real ampls[2];
    ads_real disp_int[7];
    ads_real deg_pol;
    ads_real volum;
}
```

The preferred light beam data structure is a linked list. The "ltbeam *next" element is a pointer to the next light beam data structure in the linked list. Beams in different bounces (i.e., beams of different generations) are not linked to each other, but beams in the same bounce are linked together.

The "facet_*inface" element is a pointer to the data structure for the facet through which the light in the beam originally entered the gemstone. The "facet *outface" element is a pointer to the data structure for the facet through which the previous refraction of the beam occurred.

The "facet *parent" element contains a pointer to the data structure for the facet from which the light beam was just reflected (termed the "parent" facet for the beam). The "resbuf *verts" data structure is a pointer to a linked list of vertices of a polygon describing the portion of the parent facet illuminated by the reflected light beam.

The "resbuf *path" element is a pointer to a linked list of vertices for a polygon describing the projection of the reflection of the light beam back onto the parent facet. The "domain" element is a 3×2 array describing the coordinates of the bounding box for the reflection of the light beam. The "dircos" element is an 8×3 array containing the direction cosines (with respect to the axes of the global coordinate system) for the dispersion components of the light beam.

The "index" element is the index of refraction for the gemstone material in which the reflecting facet of the light beam lies.

The "area_r" element contains the area of the reflection of the light beam in the plane of the reflecting facet. The "area_x" element contains the cross sectional area of the light beam. This quantity is calculated by multiplying the cosine of the angle of incidence of the light beam upon the plane of the reflecting facet by the quantity area_r. The intensities of the magnetic and electric components of the white monochrome components of the light beam are stored in the "xsec_intp" and "xsec_ints" elements, respectively. When a light beam is refracted, these two values are averaged to create the values stored in the "xsec_int" element of the "refract" data structure.

The "ampls" element is a 2-element array that stores the amplitudes of the electric and magnetic components of the white monochromatic component of the light beam, as described above with respect to the "refract" data structure. The "ampls" element is used to limit the "lifetime" of a beam within the gemstone. In one embodiment, when the "ampls" value for a particular light beam falls below a predetermined threshold value, that lightbeam is discarded because further processing of the light beam would not significantly affect the grade.

The "disp_int" element is a 7-element array that contains the intensities for all of the dispersion components except the white monochromatic components. The "deg_pol" element contains the degree of polarization of the white monochromatic component of the light beam, calculated as described above with respect to the "refract" data structure. The "volume" element contains a running total of the volume of gemstone material traversed by the light beam, and the corresponding portions of its parent light beams since entering the gemstone.

12.0 Refraction of Light into the Stone

Once the model has been constructed and is illuminated, the process of modeling or tracing the light through the stone can begin. The first part of this tracing is to model or trace the refraction of the light from the light sources of the illumination model into the stone. An example process for accomplishing such refraction is now described.

Figure 14:
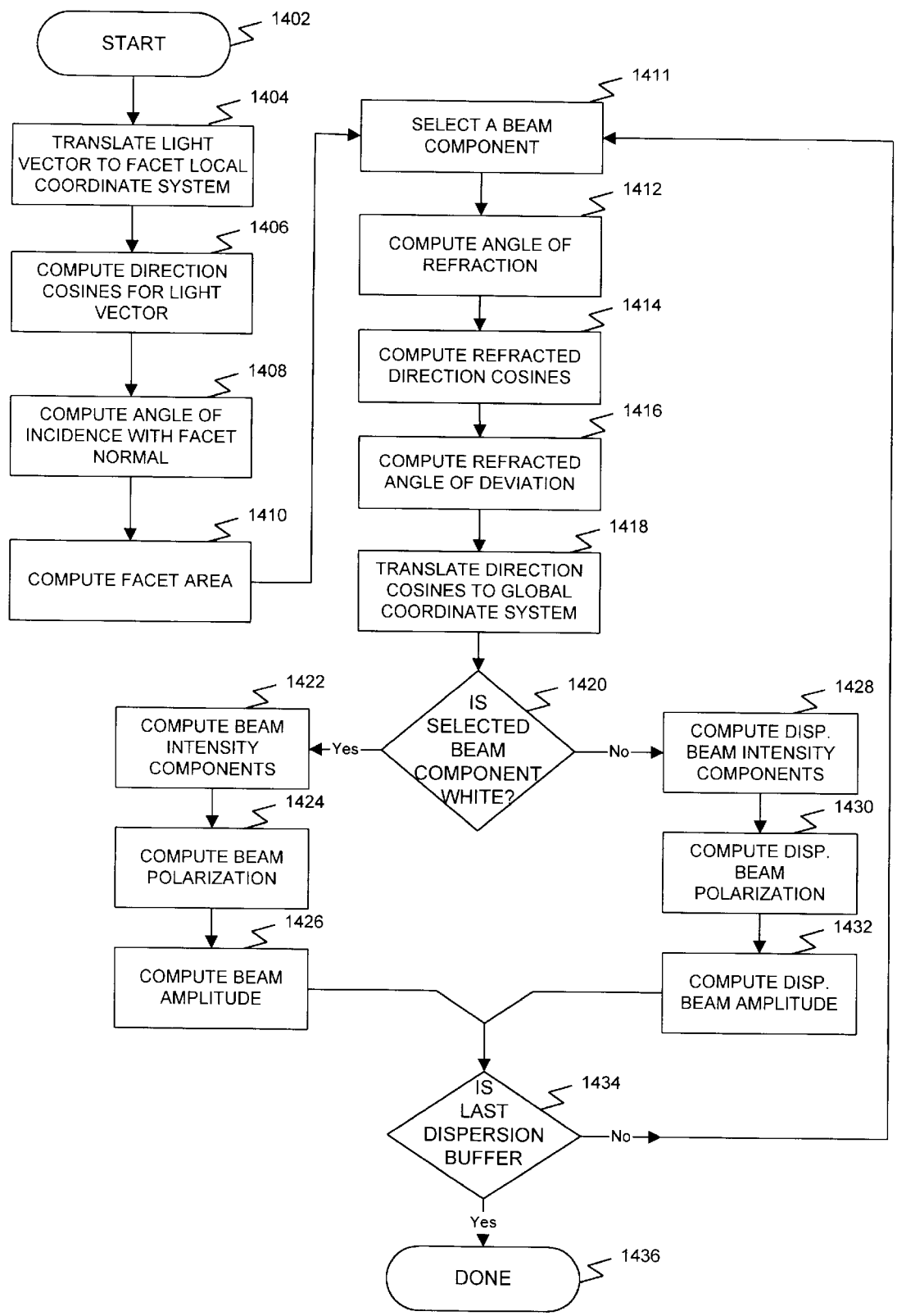
FIG. 14 is a flowchart describing a global coordinate system representation of the light vector according to one embodiment of the invention.

The incident light vector is represented as two points in the global coordinate system. Referring to FIG. 14, this global coordinate system representation of the light vector is converted to a representation in the local coordinate system of the refracting facet, as shown in a step 1404. This local coordinate system representation of the incident light vector is then converted into direction cosines with respect to the axes of the local coordinate system, as shown in a step 1406. Next, the angle of incidence of the light vector is computed with respect to the facet's normal line, as shown in a step 1408. The angle of incidence is the same as the direction cosine angle for the z axis. Next, the actual area of the facet is computed by methods that would be apparent to one skilled in the relevant art. This value is stored, as shown in a step 1410.

Next, the refracted directions and intensity polarization and amplitudes are computed for each dispersion component, and for the Pointing vector. First a beam component is selected for processing, as shown in a step 1411. The beam component can be the "white" beam component, or one of the "dispersion" components. In a preferred embodiment of the present invention, there are seven dispersion components: red, orange, yellow, green, blue, violet and ultraviolet.

Next, the angle of refraction for the selected beam component is computed based on the index of refraction for that component, as shown in a step 1412. Then, the direction cosines for the refracted beam component vector are computed, as shown in a step 1414. These direction cosines are computed with respect to the axes of the local coordinate system.

If the selected beam component is one of the "dispersion" components, then its refracted direction vector will deviate from that of the previous dispersion component by a certain angle of deviation. The angle of deviation is computed in a step 1416. Finally, the direction cosines of the refracted beam component vector are translated to the global coordinate system, as shown in a step 1418.

Processing then diverges based on whether the selected beam component is the "white" component or a "dispersion" component, as shown in a step 1420. First, the intensity of the electric and magnetic components of the selected beam component are computed. If the selected beam component is the "white" component, then electric and magnetic intensity components are stored separately as xsec_ints and xsec_intp, respectively, as shown in a step 1422. However, if the selected beam component is not the "white" component, then the computation of the intensity components is effected by the refracted angle of deviation calculated in a step 1416. The electric and magnetic intensity components calculated are averaged and stored as "disp_int", as shown in a step 1428.

Next, the degree of polarization of the selected beam component is calculated, as shown in steps 1424 and 1430. The degree of polarization is a measure of the relative amplitudes of the electric and magnetic components of the light beam. The resulting value is stored in the "deg_pol" field.

Finally, the amplitude of the selected beam component is computed, as shown in steps 1426 and 1432; the resulting values are stored in the "ampls" array. The direction cosines of the refracted beam component are stored in the "dircos" array. Steps 1411–1432 are repeated for each beam component, as shown in a step 1434.

13.0 Reflect Light Within Gemstone Model

The process described above with reference to FIG. 14 is an example process for determining the light refracted into the gemstone by a facet. In order to continue the modeling process, this light refracted into the stone is modeled as it strikes one or more facets in the stone, resulting in a set of one or more reflections. Subsequent reflections from each of the first set of reflections are modeled. This process is continued for each subsequent reflection.

In a preferred embodiment, the light beam refracted into the stone, its subsequent reflections, and any refractions out of the stone are modeled as three dimensional light beams. That is, each light beam has a cross sectional area, and a direction of propagation. The interaction of this three-dimensional beam with each facet (also defined in three dimensions) is modeled. This three-dimensional approach results in an evaluation of the stone which is far superior to that obtainable from two-dimensional models.

Note that computer simulation techniques are available that could be applied to evaluate the propagation of light within a gemstone. One such technique is known as "ray tracing." Ray tracing could be used to extend the Tolkowsky technique from two dimensions to three dimensions. However, a very large number of ray traces would be required to evaluate a single gemstone model. The computational resources required to implement this technique would impose an overly burdensome cost upon the evaluation of gemstones, and so is not practicable. Further, computer ray tracing does not consider cross-sectional geometry, and so cannot consider light beam characteristics such as beam volume.

One process for modeling the propagation of light within the gemstone is now described. In a preferred embodiment of the present invention, the modeling of the propagation of light within the gemstone model is structured as three nested loops: bounce, beam, and facet loops. A "bounce" describes a set of simultaneous reflections. In the first bounce, a light beam is created by propagating the light reflected from or refracted by a facet within the gemstone until it strikes one or more other facets. The facet from which a light beam originates is termed the "sending" facet for that light beam. The facet(s) that the light beam eventually strikes are termed the "receiving" facet(s) for that light beam. When the light beam reflects internally from a gemstone facet, the resulting reflected light beam(s) are termed "child" light beams. The light beam which struck a facet resulting in the child beam is termed the "parent" light beam.

For example, if the parent light beam in the first bounce strikes three receiving facets, then three child light beams are created. These three light beams make up the second bounce. If these three light beams in the second bounce strike a combined total of ten facets, for example, the third bounce will be comprised of ten new light beams. The three child light beams of the second bounce become parents to the ten child light beams in the third bounce, and so on.

In one embodiment, the beams within each bounce are processed sequentially. In an alternative embodiment, beams within each bounce are processed in parallel using multi-threading or parallel processing techniques.

For each beam being processed, every facet in the gem is searched to determine whether that beam strikes that facet. When a light beam is found to strike a facet, that facet is processed to determine the resulting reflections and refractions, if any. If a facet is not struck by the light beam, such processing need not be performed.

In the sequential embodiment, when all of the facets for a particular beam have been processed, the next beam is processed. When all of the beams for a particular bounce have been processed, the next bounce is processed. Alternative embodiments can be implemented for processing beams in an alternative order, as opposed to this bounce-by-bounce approach.

In a preferred embodiment, a predetermined bounce threshold is set to limit the number of bounces processed. If a predetermined bounce threshold has been set, the processing terminates when the number of bounces exceeds that threshold. Additionally a processing limit can be set such that processing terminates when the light remaining in the beam is deemed too insignificant to merit further processing. This limit can be used instead of or in addition to the bounce threshold.

Figure 15:
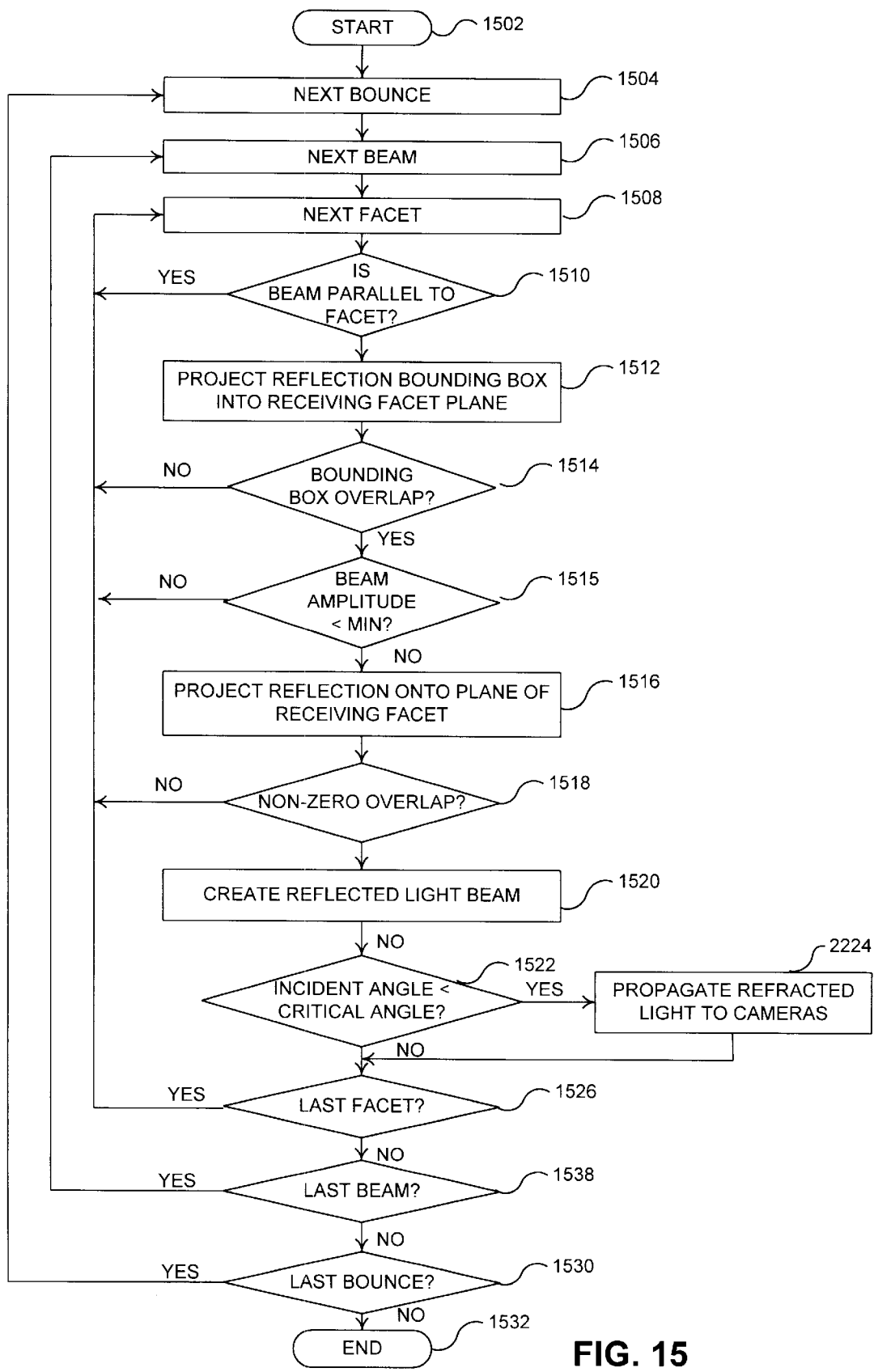
FIG. 15 is a flowchart illustrating one process for reflecting light within the gemstone model according to a preferred embodiment of the invention.

FIG. 15 is a flowchart illustrating one process for reflecting light within the gemstone model according to a preferred embodiment of the invention. As stated above, the preferred process follows a bounce-by-bounce technique, wherein each beam of each bounce is processed sequentially. After reading this description it will become apparent to a person skilled in the art how to process reflections in the gemstone using other processing methodologies.

In a step 1504, the first bounce is selected for processing. In a step 1506, the first beam within the bounce is selected for processing. In a step 1508, the first facet in the gemstone is selected for processing with the selected beam.

If the beam is parallel to the facet, then it will not strike the facet, and thus should not be processed. Thus, in a step 1510 it is determined whether the beam is parallel to the selected facet. If so, as indicated by the "yes" branch, the next facet is retrieved.

If the beam is not parallel to the facet, as indicated by the "no" branch from step 1510, then a screening test is performed to determine whether it is possible for that beam to strike that facet, as shown in a step 1512. In a preferred embodiment, the test proceeds by comparing a "bounding box" of the polygon described by the light beam's reflection in the sending facet to the "bounding box" of the facet in question. If the bounding boxes do not intersect, as indicated by the "no" branch from step 1514, then there will be no reflection of the chosen beam from the chosen facet. Therefore, no further processing needs to be performed for the beam/facet pair. Consequently, another facet is selected for processing, as shown in step 1508.

In one embodiment, the "bounding box" is a parallelogram circumscribing the polygon, as described below. Because the bounding box comparison is far less time-consuming than the reflection-facet comparison (described below), this screening test conserves a significant degree of processing resources.

The bounding boxes are compared by projecting the bounding box of the reflection along the Pointing vector of the light beam. A simple test determines whether the two bounding boxes intersect, as described below.

If the bounding boxes intersect, as indicated by the "yes" branch from step 1514, then the beam/facet pair may result in a subsequent reflection.

In the embodiment illustrated in FIG. 15, before further processing is continued, the amplitude of the beam is checked to determine whether further processing of this beam would significantly affect the outcome of the evaluation of the gemstone, as shown in a step 1515. In one embodiment, this is done by comparing the beam amplitude to a defined minimum amplitude. If the beam amplitude is less than a predetermined minimum, then processing for this beam/facet pair does not need to be continued and another facet is selected for processing.

If the beam amplitude is above the minimum, then the reflection is compared to the receiving facet directly, as shown in steps 1516 and 1518. Specifically, in the illustrated embodiment, the boundary of the beam is projected onto the plane of the facet to determine whether the boundary of the projection overlaps the boundary of the facet. In other words, these steps determine whether part or all of the beam as projected by the sending facet actually strikes the chosen facet in question.

If the projection of the reflection onto the plane of the receiving facet does not overlap the receiving facet, then further processing of the beam/facet pair is not required and a new facet is selected for processing, as shown in a step 1508. However, if there is an overlap, light will be reflected from the chosen facet. Therefore, a new light beam is created as a result of this reflection, as shown in astep 1520.

In one embodiment, the user can limit processing by specifying a minimum area of overlap. If the area of a facet illuminated by a light beam is less than the specified overlap area threshold, the beam/facet pair does not need to be processed, and so no reflections or refractions will be generated for that light beam/facet pair.

If the incident angle of the light beam on the receiving facet is less than the critical angle of the gemstone material, as shown by the "yes" branch from step 1522, then light will exit the gemstone through the facet. Therefore, a refracted light beam is created, as shown in a step 1524.

In the described embodiment, processing of the light beam continues until all of the facets in the gemstone have been processed for that beam, as shown in a step 1526. When the last facet has been processed for the light beam, as shown by the "no" branch 1526, then the next beam is processed, until all of the light beams in the bounce have been processed, as shown in a step 1528. When the last bounce has been processed, as shown by the "no" branch from step 1530, then reflection processing terminates.

14.0 Project Reflection Bounding Box onto Receiving Facet Plane

As described above, the direct comparison of a projected light beam to a selected facet to determine whether the facet is illuminated is a time-consuming process. Therefore, In a preferred embodiment of the present invention, this process can be avoided in many cases through a simple screening test. The step of performing this screening test was described above as steps 1512 and 1514.

One embodiment for performing this test is now described. In this test, two quadrilaterals are then defined. One quadrilateral circumscribes the projection of the beam in the sending facet plane, and the other circumscribes the selected facet. These two quadrilaterals are referred to as the "beam bounding box" and the "facet bounding box," respectively.

The beam bounding box is projected along the Pointing vector of the reflected light beam onto the plane of the selected facet. This projection is referred to as the projection of the beam. This projection of the beam has a bounding box referred to as the "projection bounding box." The projection bounding box can be computed from the projection of the beam bounding box on to the plane of the facet. The projection bounding box is compared to the facet bounding box. If no overlap is found for these two bounding boxes, then the reflected light beam cannot possibly illuminate the selected facet. Therefore, the time-consuming direct comparison of the projected beam's geometry to the selected facet's geometry is rendered unnecessary.

Figure 16:
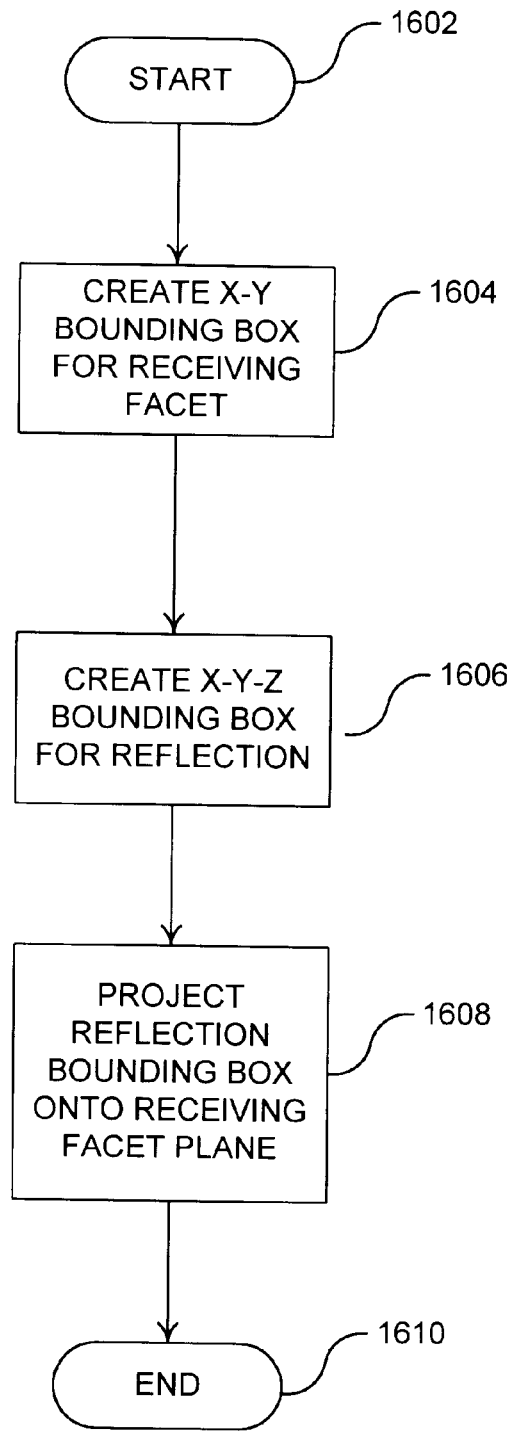
FIG. 16 is a flowchart depicting an example process for creating the bounding boxes according to a preferred embodiment of the invention.

FIG. 16 is a flowchart depicting an example process for creating the above-described bounding boxes according to a preferred embodiment of the invention. The process described with reference to FIG. 16 is one process for implementing step 1512 in FIG. 15.

In a step 1604, the bounding box for the selected facet is created. In a preferred embodiment, the bounding box for the selected facet is created by taking the x and y values of the facet domain computed during facet extraction. In an alternative embodiment, the bounding box for the selected facet is created by examining each vertex of the selected facet in turn to determine the minimum and maximum x and y values for the vertices of the selected facet.

These four values are then used to define the vertices of a parallelogram circumscribing the selected facet. This parallelogram is the bounding box for the selected facet. Because the comparison of the facet bounding box of the selected facet to the projection bounding box is accomplished in two-dimensional space, rather than three-dimensional space, only the x and y coordinates of this bounding box are required. As would be apparent to one skilled in the relevant art, any two Cartesian coordinates could be used for this process.

In a step 1606, the bounding box for the beam is created. This bounding box is created by examining each of the vertices of the beam to determine the minimum and maximum x, y and z values for the vertices of the reflection. These six values are then used to define the vertices of a parallelogram circumscribing the polygon describing the beam in the plane of the sending facet. This parallelogram is the beam bounding box.

Next, the bounding box of the beam is projected along the Pointing vector of the reflected light beam onto the plane of the selected facet to create the projection bounding box. The projection operation necessitates the use of a z coordinate in defining the reflection bounding box, as described above. In a preferred embodiment, the projection bounding box is created by projecting each vertex of the reflection bounding box along the Pointing vector of the reflected light beam onto the plane of the selected facet, and then using the projected vertices to define a quadrilateral on the plane of the selected facet. This quadrilateral is the projection bounding box.

15.0 Compare Projected Bounding Box to Facet Bounding Box

Figure 17:
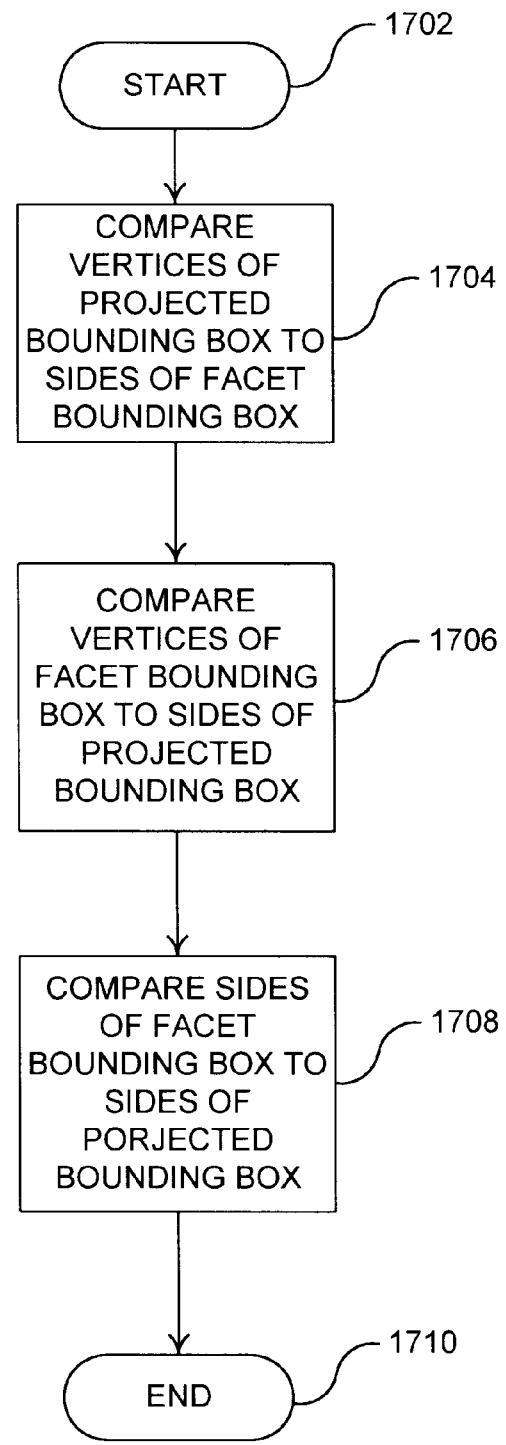
FIG. 17 is a flowchart illustrating an example process for comparing the projected bounding box to the facet bounding box according to a preferred embodiment of the invention.

FIG. 17 is a flowchart illustrating an example process for comparing the projected bounding box to the facet bounding box according to a preferred embodiment of the invention. This FIG. 17 illustrates one example process for implementing step 1514 of FIG. 15. In the preferred embodiment, the comparison between the two bounding boxes is effected through the use of x and y coordinates only. As described above, any two of the three Cartesian coordinates could be used without departing from the spirit and scope of the present invention. The projection of each bounding box onto the x-y plane describes a parallelogram, which in one embodiment is a rectangle. Therefore, the comparison can be reduced to determining whether two parallelograms (termed the "projection rectangle" and the "facet rectangle") in a plane overlap.

In a preferred embodiment, two scenarios are examined to determine whether the rectangles overlap. In the first scenario, one or more vertices of one rectangle falls within the boundary of the other rectangle. In a step 1704, the vertices of the projection rectangle are compared to the boundaries of the facet rectangle. In a step 1706, the vertices of the facet rectangle are compared to the boundaries of the projection rectangle.

In the second scenario, none of the vertices of either rectangle fall within the boundary of the other, yet they still overlap. In a step 1708, the sides of the two rectangles are compared to determine whether this is the case.

Figure 18:
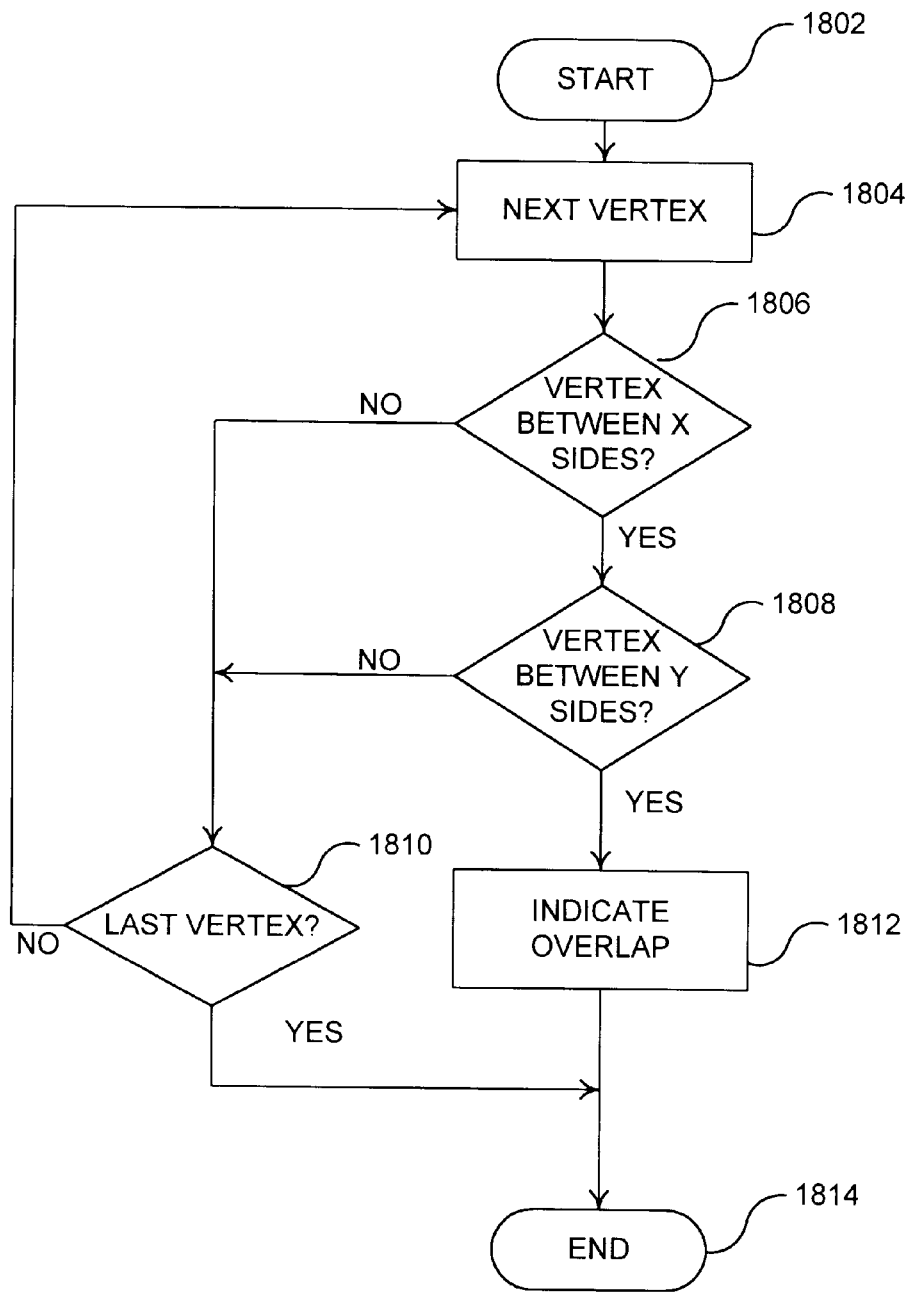
FIG. 18 is a flowchart illustrating an example process for comparing a vertex of one rectangle to the sides of a second rectangle according to a preferred embodiment of the invention.

FIG. 18 is a flowchart depicting a process for comparing the vertices of one rectangle to the boundaries of another according to a preferred embodiment of the invention. This operation corresponds to each of steps 1704 and 1706 in FIG. 17.

Referring to FIG. 18, a vertex of one rectangle is selected for comparison to the sides of the second rectangle, as shown in a step 1804. The vertex is first compared to the minimum and maximum x values describing the sides of the second rectangle, as shown in a step 1806. If the vertex is not between the two sides, then another vertex of the first rectangle is selected for processing, unless the last vertex of the rectangle has been processed, as shown in a step 1810.

However, if the selected vertex falls between the "x sides" of the second rectangle, then the vertex is examined to determine whether it falls between the minimum and maximum y extents of the second rectangle, as shown in a step 1808. If the vertex does not fall between these "y sides," then another vertex is selected for processing, until all vertices of the first rectangle have been processed, as shown in a step 1810. However, if the selected vertex falls between the "y sides" of the second rectangle, then the vertex falls within the boundary of the second rectangle and overlap is indicated, as shown in a step 1812.

Figure 19:
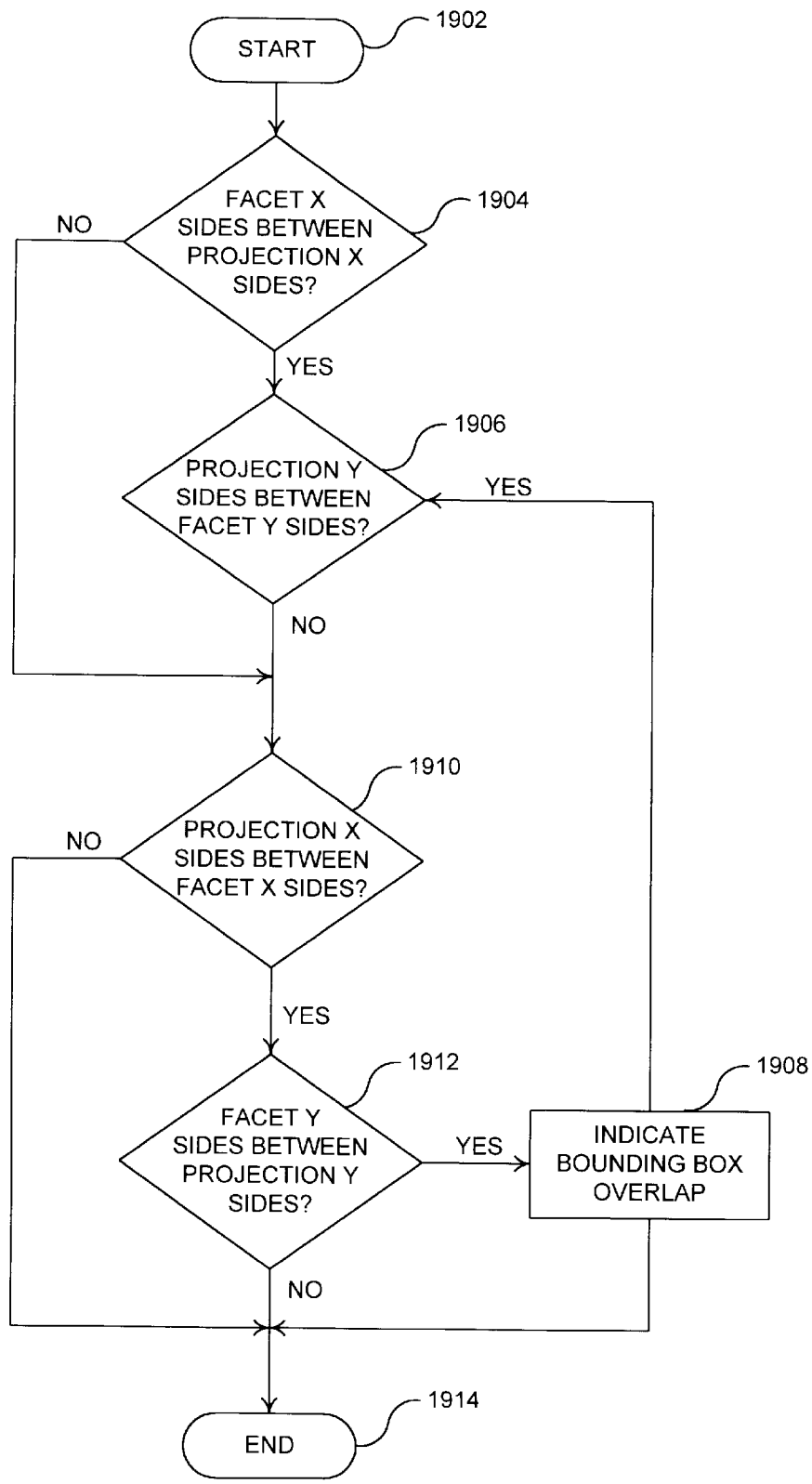
FIG. 19 is a flowchart depicting an example process for comparing sides of a facet rectangle to sides of a projected rectangle according to a preferred embodiment of the invention.

FIG. 19 is a flowchart depicting a process for comparing the sides of the facet rectangle to the sides of the projected rectangle according to a preferred embodiment. This operation corresponds to step 1708 in FIG. 17. The two rectangles will overlap in one of two scenarios, which are depicted in FIGS. 20 and 21.

Figure 20:
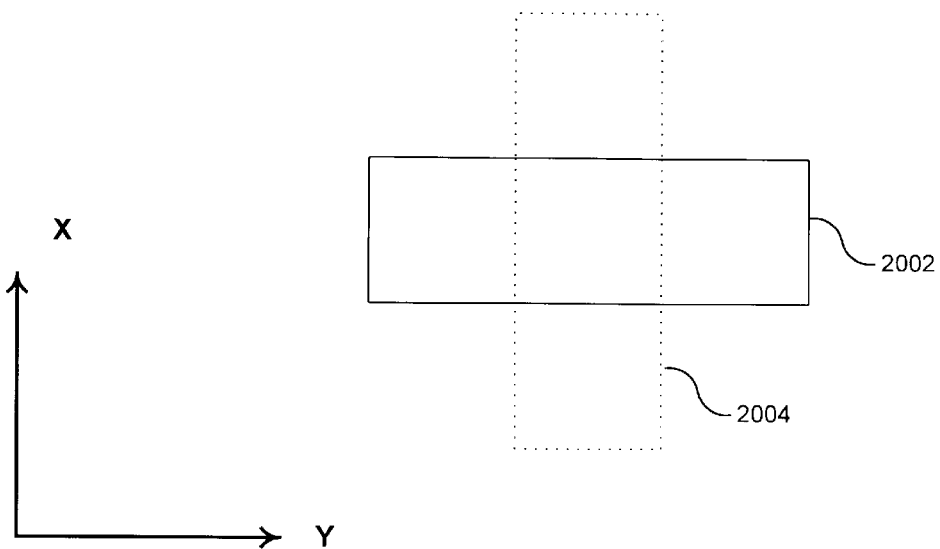
FIG. 20 depicts a scenario where the facet rectangle and the projection rectangle overlap.

In FIG. 20, the projection rectangle 2004, indicated by dashed lines, is of greater x extent and lesser y extent than facet rectangle 2002, represented by the dotted lines. FIG. 21 depicts the complementary scenario, where the facet rectangle is of greater x extent and lesser y extent than the projection rectangle.

FIG. 19 is a flowchart depicting an example process for comparing the sides of the facet rectangle to the sides of the projected rectangle according to a preferred embodiment. This operation corresponds to step 1708 in FIG. 17. The scenario depicted in FIG. 20 is tested in steps 1904 and 1906 of FIG. 19. In step 1904, the x sides of the facet rectangle are compared to the x sides of the projection rectangle. If the facet x sides are not between the projection x sides, then the scenario of FIG. 20 is incorrect. However, if the facet x sides lie between the projection x sides, then the projection sides are tested to determine whether they lie between the facet y sides, as shown in step 1906. If not, then the scenario of FIG. 20 is incorrect. However, if the projection sides do lie between the facet y sides, then the scenario of FIG. 20 is correct, and rectangle overlap is indicated, as shown in a step 1908.

Figure 21:
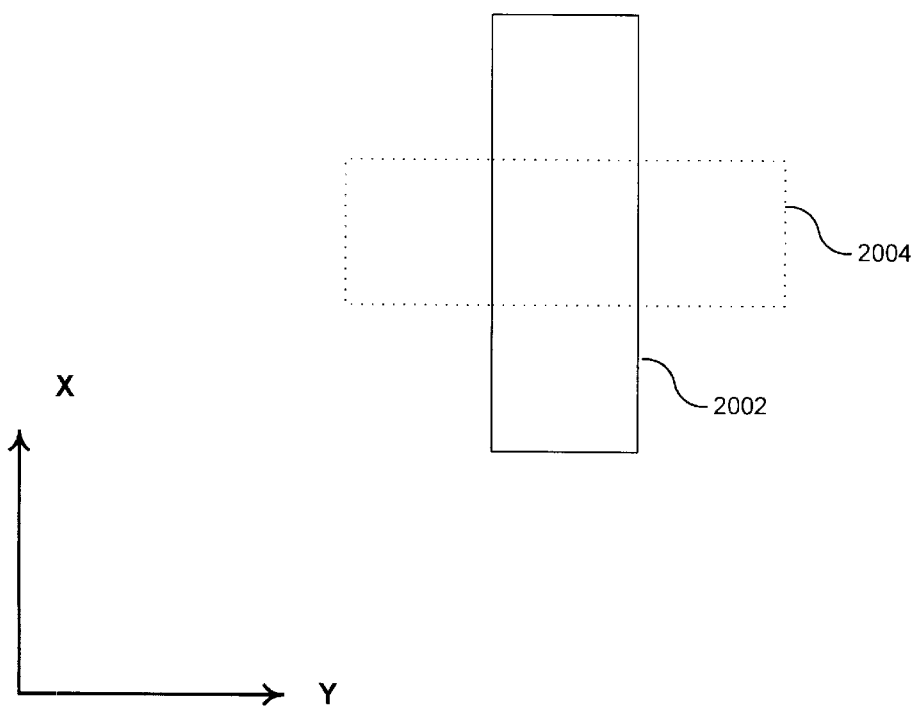
FIG. 21 depicts a complementary scenario to that shown in FIG. 20, where the facet rectangle is of greater x extent and lesser y extent than the projection rectangle.

If the scenario of FIG. 20 is found to be incorrect, then the scenario of FIG. 21 is tested, as shown in steps 1910 and 1912. In step 1910, the projection x sides are compared to the facet x sides. If the projection x sides lie between the facet x sides, then the facet y sides are compared to the projection y sides, as shown in a step 1912. If the facet y sides lie between the projection y sides, then the scenario of FIG. 21 is correct, and bounding box overlap is indicated, as shown in a step 1908. Otherwise, both scenarios of FIG. 20 are incorrect, and no overlap is indicated.

16.0 Create Reflected Light Beam

Figure 22:
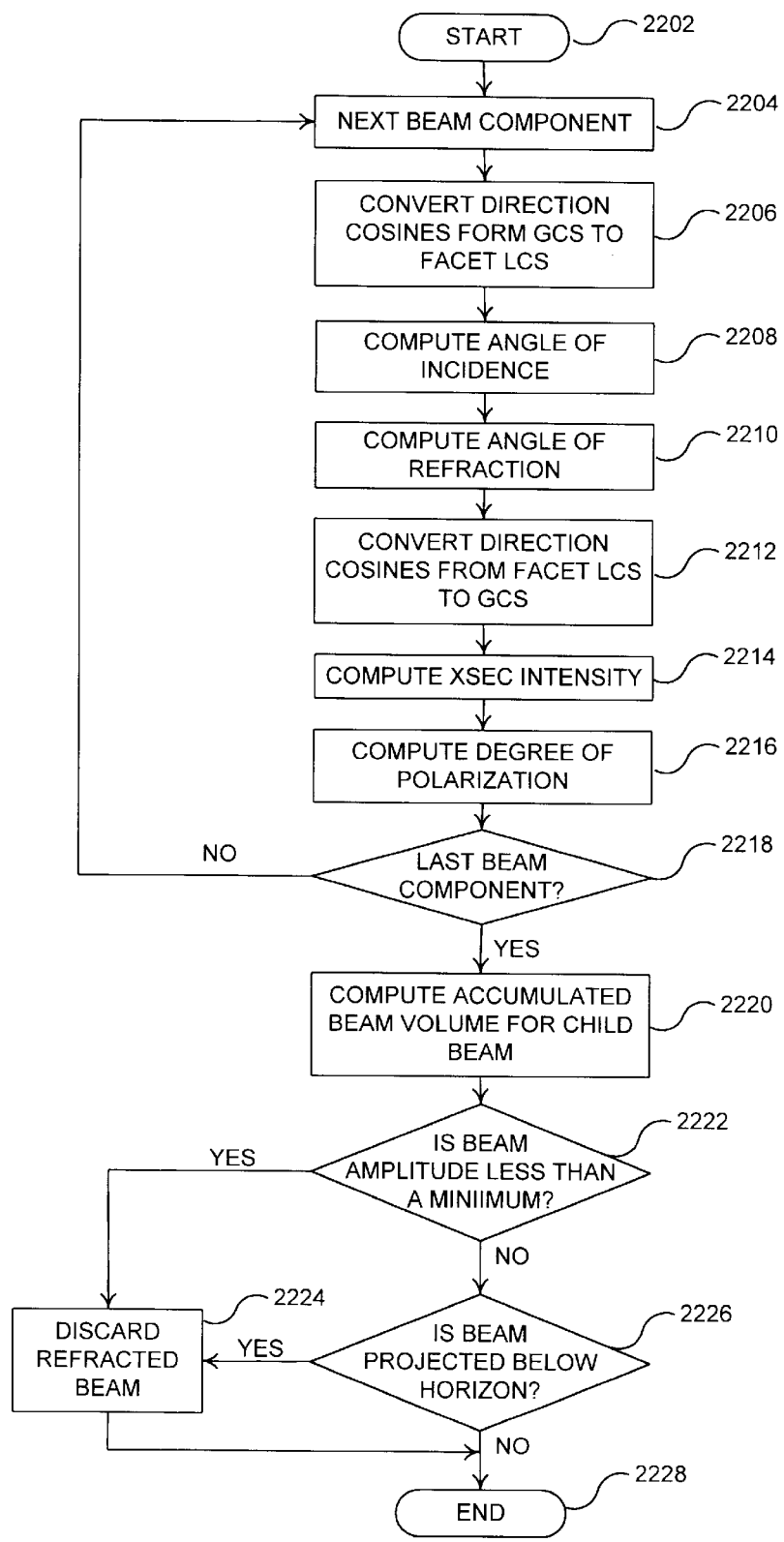
FIG. 22 is a flowchart depicting an example process for creating a reflected light beam, according to a preferred embodiment of the invention.

When a virtual light beam within the gemstone model strikes a facet, a new beam is created by the reflection, as described with respect to step 1520 in FIG. 15. FIG. 22 is a flowchart depicting an example process for creating a reflected light beam, according to a preferred embodiment of the invention. The beam striking the reflecting facet is termed the "parent" beam, and the resultant reflected beam is termed the "child" beam. Data describing the child beam is derived from the data describing the parent beam, the position and geometry of the reflecting facet, and the refractive index of the gemstone material.

For each beam component, the reflected direction, energy loss through refraction, intensity, and degree of polarization are calculated. Finally, the accumulated beam volume for the child beam is calculated. Referring to FIG. 22, a beam component is selected, as shown in a step 2204.

In a preferred embodiment, the calculations of angles of incidence and refraction are performed in the local coordinate system of the reflecting facet. Therefore, the direction vector of the beam component is converted from the global coordinate system to the facet local coordinate system, as shown in a step 2206. In a preferred embodiment of the present invention, the direction vector of the beam component is described by direction cosines with respect to the axis of the relevant coordinate system.

Next, the direction vector for the reflected beam component is computed, as shown in a step 2208. Because, in the preferred embodiment, the incident direction vector is represented in the facet local coordinate system, in this embodiment, the reflected direction vector can be calculated by operating only on the direction cosine for the local z axis, which is the normal line for the facet plane.

Some beam energy may be lost through refraction. The portion of energy lost through refraction is based on the angle of refraction. Therefore, the angle of refraction is calculated in a step 2210.

Next, the reflected direction vector for the beam component is converted from the facet local coordinate system to the global coordinate system, as shown in a step 2212. Then the cross-sectional intensity of the reflected beam component is calculated, as shown in a step 2214. This calculation is based on the amount of energy remaining in the reflected beam, which is based on the portion of energy lost through refraction calculated in step 2210. In one embodiment, this calculation is similar to that described for reflecting light into the gemstone, as shown in a step 1422.

Next, the degree of polarization for the beam component is calculated, as shown in a step 2216. In one embodiment, this calculation is similar to that described for refracting light into the gemstone, as shown in a step 1424.

Where the beam is comprised of several components, steps 2206 through 2216 are performed for each beam component, as shown in steps 2218 and 2204. When all of the beam components have been processed, the accumulated beam volume for the child beam is calculated, as shown in a step 2220. This is accomplished by apportioning the accumulated volume of the parent beam to each child beam based on percentage of cross-section of the parent beam, and adding to that the portion of the volume of the parent beam that is reflected by the reflecting facet to create the child beam.

In a preferred embodiment of the present invention, only the beam volume that is related to the Pointing vector of the live beam is tracked. In an alternate embodiment, the beam volumes for each dispersion component are also tracked.

17.0 Propagate Refracted Light to Cameras

When light is refracted from the gemstone, as discussed above, depending on the direction of that propagated light, that light is propagated to one or more cameras for capture and measurement. In a preferred embodiment, each refraction is processed by one camera only, unless camera overlap is specified. In an alternative embodiment, each refraction can be processed by more than one camera, even if no overlap is specified. As discussed above, the cameras collect light refracted from the gemstone model, for processing to determine the gemstone grade.

Figure 23:
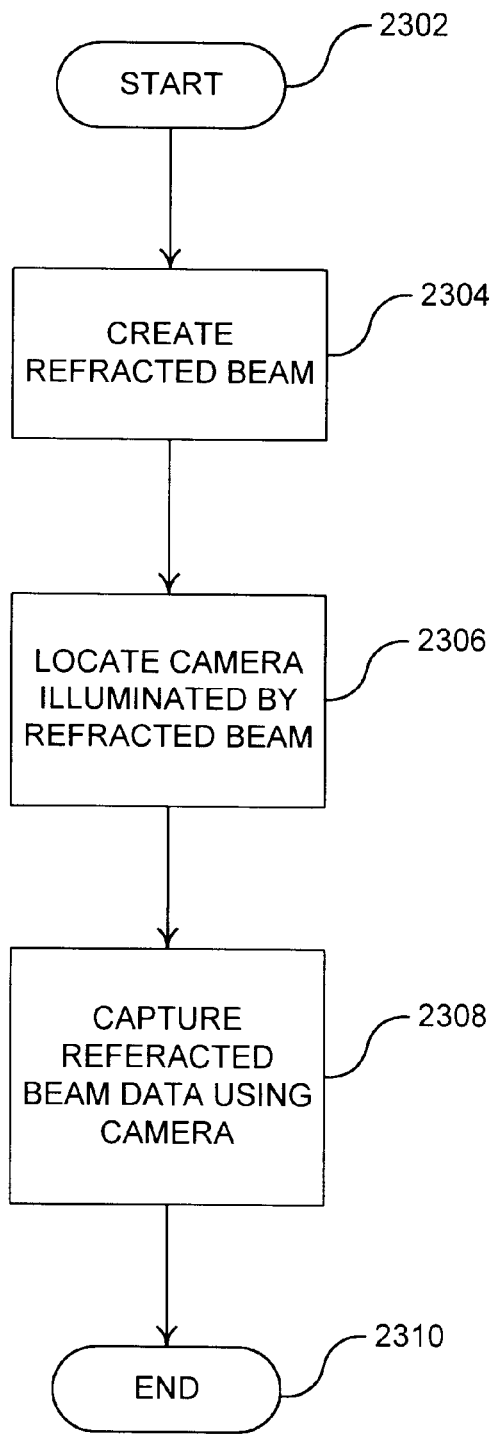
FIG. 23 is a flowchart depicting an example process for propagating refracted light to one or more cameras, according to a preferred embodiment of the invention.

FIG. 23 is a flowchart depicting an example process for propagating refracted light to the cameras, according to a preferred embodiment of the invention. This process illustrates one manner in which step 1524 of FIG. 15 can be performed.

When light exits the gemstone model through refraction, a new beam is created to describe the characteristics of the refracting light, as shown in a step 2304. In a preferred embodiment, this data is stored in the "refract" data structure, as described in detail below. In alternative embodiments, other data structures are used.

Next, one or more cameras are selected to process the refracted light. The camera(s) are selected by determining which of the cameras in the camera array are illuminated by the refracted beam, as shown in a step 2306. Once a camera has been selected, that camera is used to capture the data describing the refracted light beam, as shown in a step 2308. When reflection and refraction for the light in the gemstone is complete, and the cameras have collected the resulting data, that data is processed to generate a gemstone grade.

18.0 Locate Cameras Illuminated by Refracted Beam

Figure 24:
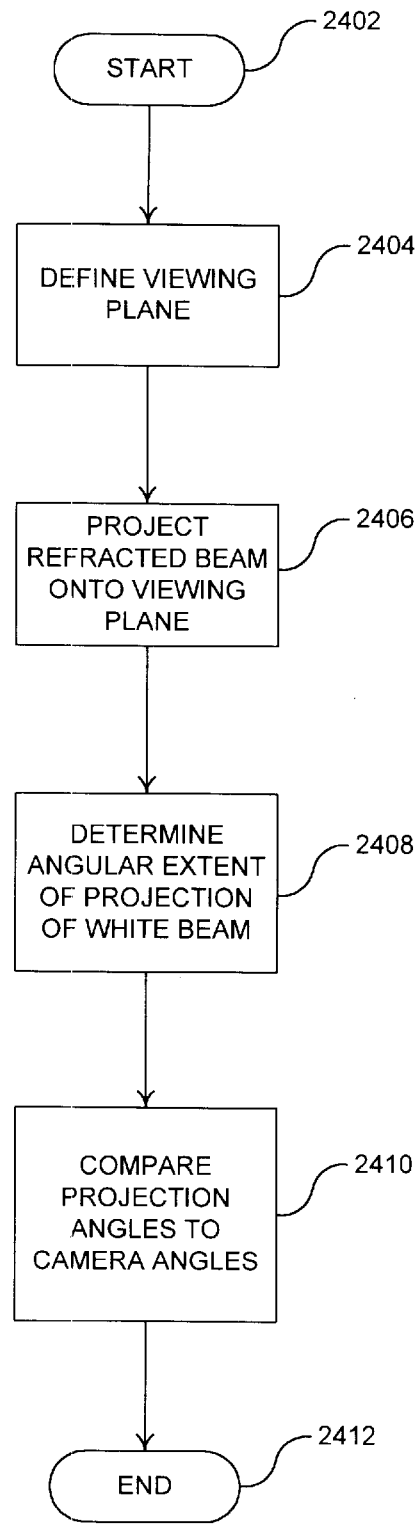
FIG. 24 is a flowchart illustrating an example process for locating the cameras illuminated by a refracted beam according to a preferred embodiment of the invention.

Once a refracted beam has been generated to represent the light exiting the gemstone model through refraction, the camera illuminated by the refracted beam is selected for processing. FIG. 24 is a flowchart an example process for locating the cameras illuminated by a refracted beam according to a preferred embodiment of the invention. This operation is an example implementation of step 2306 in FIG. 23.

First, a "viewing plane" is defined with respect to the refracted beam, as shown in a step 2404. In a preferred embodiment, the viewing plane is defined as normal to the Pointing vector of the light beam at the viewing distance selected by the user. As discussed above, the pointing vector is also referred to as the direction vector for the white beam component.

Figure 25:
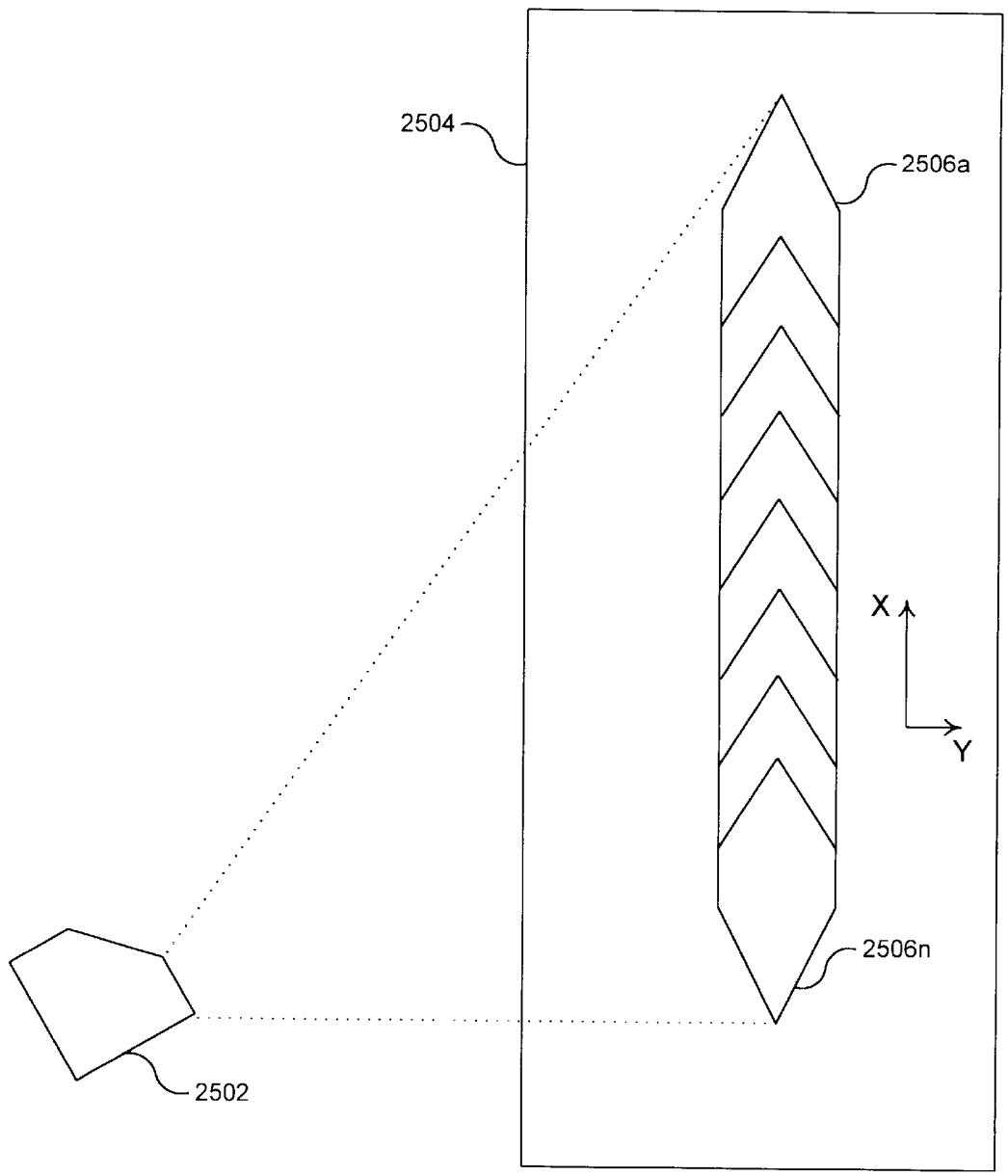
FIG. 25 depicts the projection of the light beam onto a viewing plane according to a preferred embodiment of the invention.

Once a viewing plane has been defined, the refracted light beam is projected onto that plane, as shown in a step 2406, for defining the direction of the beam with respect to the cameras, and for measuring certain characteristics of the beam. The projection of the light beam onto the viewing plane results in a repetitive pattern, as shown in FIG. 25.

The angular extent of the projection of the refracted beam onto the viewing plane is then measured as seen from the global origin, as shown in a step 2408. In a preferred embodiment, the projection measured is that for the white beam component only. Other embodiments contemplate a measurement using dispersion components. In the preferred embodiment, the angular measurements are the minimum and maximum angles of azimuth and elevation.

In a step 2410, the angular extent of the projection of the white beam component onto the viewing plane is compared to the angular extents of the cameras in the camera array, to determine which camera is illuminated by the refracted beam. Because, in the preferred embodiment, both the projection and the camera lenses are described in the same manner (that is, in terms of elevation and azimuth angles), in this embodiment, the comparison is a simple calculation, as would be apparent to one skilled in the relevant art.

19.0 Capture Refracted Beam Data Using Camera

Figure 26:
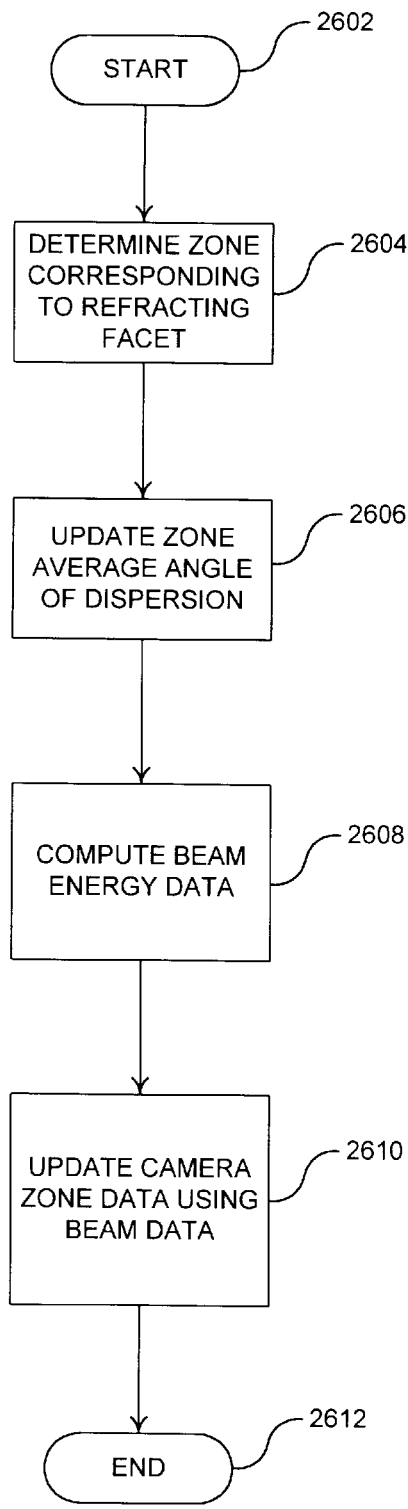
FIG. 26 is a flowchart illustrating an example process for capturing refracted beam data using an illuminated camera according to a preferred embodiment of the invention.

In the preferred embodiment, once the camera illuminated by the refracted beam is found, that camera's data is updated using data from the refracted beam. FIG. 26 is a flowchart illustrating an example process for capturing refracted beam data using the illuminated camera according to a preferred embodiment of the invention. This illustrates an example process for performing step 2308 of FIG. 23.

As described above, each camera measures data for each gemstone facet selected for measurement. In one embodiment, for each camera, the data collected from each facet of the gemstone is stored separately. Therefore, the data describing a refracted light beam illuminating a camera can be used to selectively update only the camera zone that corresponds to the refracting facet. Therefore, in this embodiment, the first step is to determine the camera zone that corresponds to the refracting facet, as shown in a step 2604. In a preferred embodiment, the data describing the refracted light beam includes a pointer to the refracting facet, and each camera zone includes a pointer to its corresponding facet. Therefore, the zone corresponding to the refracting facet can be found through a simple comparison.

Each camera zone measures an average angle of dispersion for the refractions it has captured. When a camera captures a new refraction, the average angle of dispersion for the corresponding camera zone is updated, as shown in a step 2606.

Next, various parameters describing the incident energy of the refracted beam upon the viewing plane are calculated and used to update the camera zone corresponding to the refracting facet, as shown in a step 2608.

Finally, the computed energy data and data from the refracted light beam are used to update the camera zone corresponding to the refracting facet, as shown in a step 2610. This data includes, but is not limited to, refraction intensity, area, optical power, disperse power, dispersed intensity x path length, total beam volume, volumetric density and absorption. Each camera and each camera zone include a counter to count the number of refracted beams captured. These counters are updated to reflect the capture of the newly refracted beam.

20.0 Project Refracted Beam onto Viewing Plane

Figure 27:
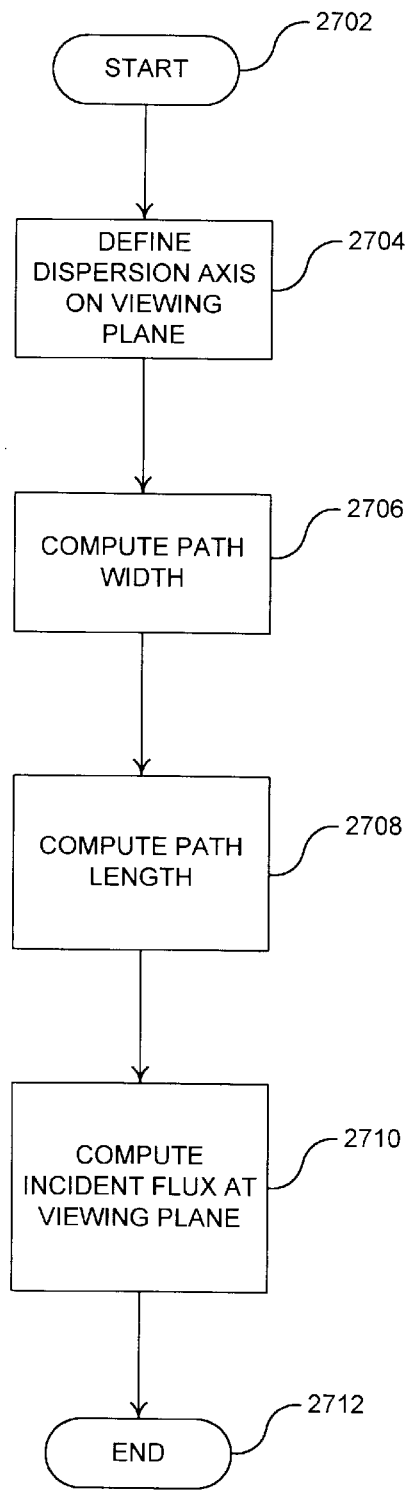
FIG. 27 is a flowchart depicting an example process for projecting a refracted beam onto its viewing plane according to a preferred embodiment of the invention.

FIG. 27 is a flowchart depicting an example process for projecting a refracted beam onto its viewing plane according to a preferred embodiment. This illustrates an example process for implementing step 2406 of FIG. 24.

When light is refracted from a gemstone onto a planar surface, it creates a rainbow pattern of similar overlapping shapes arranged in a certain direction. This direction is called the "dispersion axis." In a step 2704, this axis is defined. The dispersion axis becomes the x axis of the viewing plane local coordinate system with the x axis oriented so that increasing volumes of x correspond to dispersion components of increasing wavelengths. The z axis is a vector normal to the viewing plane oriented toward the origin of the global coordinate system. They axis is a vector in the viewing plane oriented by the x and z axis according to the right-hand rule.

Next, the "path width" of the dispersion projection on the viewing plane is measured, as shown in a step 2706. In a preferred embodiment, this measurement is the difference between the minimum and maximum y values of the dispersion projection. The dispersion axis is defined by connecting the two points on the viewing plane defined by the intersection of the viewing plane and the direction vectors of two dispersion components. The "path length" is then computed, as shown in a step 2708. In a preferred embodiment, the path length measurement is based on the angles of deviations of the direction vectors of the refracted dispersion components. The "path area" is then calculated based on the path width and path length. The "path area" is used to compute the spectral power.

Finally, the incident flux at the viewing plane is determined by multiplying the intensity, the cosine of the angle of deviation, the path length, and the path width.

21.0 Spatial Domain Processing

As described above, when processing reflections in the stone, if a reflected or refracted beam does not overlap a facet, there is no need to determine the projection of that beam on that facet and its subsequent reflection or refraction therefrom. However, if the area of a beam does overlap a facet, then the invention determines the actual area of the facet illuminated by that beam. This area is referred to as the overlap area between the light beam and the illuminated facet. More specifically, in a preferred embodiment as described above, if a bounding box defined by the projection of the beam area onto the plane of the receiving facet overlaps a bounding box defined by the receiving facet, then the invention determines the actual area of the facet illuminated by that beam.

Generally speaking, the boundaries of the light beam projected from the sending facet are projected onto the receiving facet in the direction of the light beam. If there is a spatial overlap of the projection of the light beam and the facet, the boundaries of this overlap are determined. This "overlap boundary" defines the boundary of the light which is subsequently reflected off of or refracted by the receiving facet.

When light impinges upon a facet of the stone, that facet may refract a portion of that light into the stone depending on the angle of incidence of the light. The refracted beam has a particular shape, or cross-sectional area defined by the shape of the facet that refracted the light into the stone. The shape of the refracted beam can be described by an n-sided polygon.

Once refracted into the stone, the refracted beam impinges upon one or more facets, resulting in one or more reflections of that beam in the stone. Likewise, each of these reflections subsequently impinges upon one or more facets of the stone, resulting in yet another reflection in the stone. Depending on the angle of incidence of the beam with respect to a facet, all or part of a beam may be refracted out of the stone.

In order to accurately determine the energy in the reflection or refraction from the receiving facet, and to accurately determine the shape of the resultant beam, it is necessary to determine the shape of the intersection between the original beam and the receiving facet. This shape determines the shape of the resultant beam reflected from or refracted by the receiving facet.

For example, in FIG. 1 the shape of the reflected beam 120 is a function of the intersection of beam 112 with facet 116. This portion of the document describes the manner in which this shape is determined.

When a light beam, either reflected from or refracted by a sending a facet interacts with a receiving facet, there are three scenarios which can result. These three scenarios are a partial overlap of the beam with the receiving facet, a total overlap of the facet by the beam, or a total overlap of the beam by the receiving facet. A fourth scenario occurs where the light beam does not project upon a receiving facet. This fourth scenario, then is defined by no overlap between the beam and the receiving facet.

Figure 28:
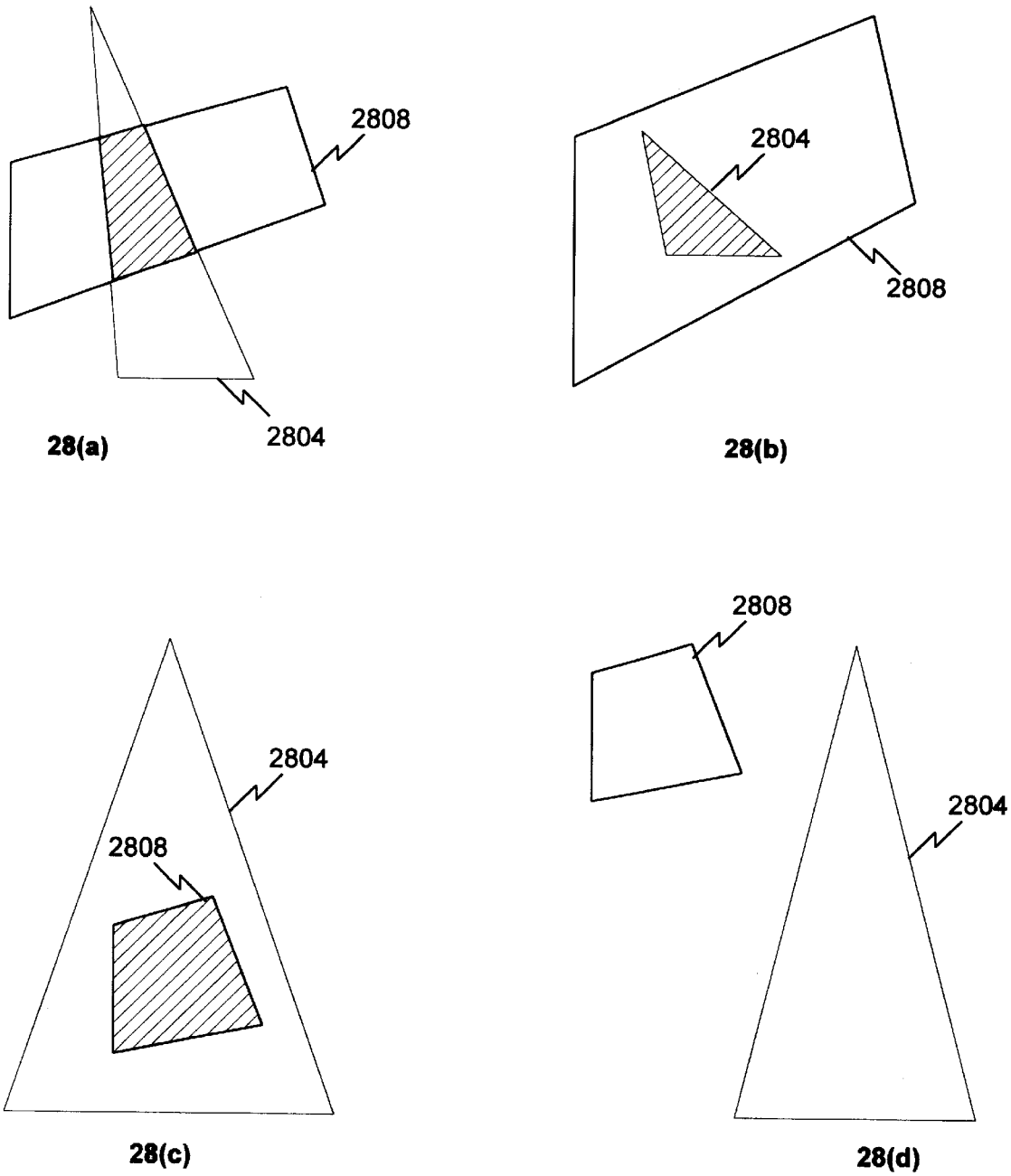
FIGS. 28(a) through 28(d) illustrate four scenarios for interaction of a beam projection with a facet boundary.

These four scenarios are illustrated in FIG. 28, which comprises FIGS. 28(*a*) through 28(*d*). Referring now to FIG. 28, a receiving facet 2804 and a beam of light 2808 are illustrated for each of the four scenarios. In FIG. 28(*a*) beam of light 2808 is shown as being projected upon facet 2804. The area of overlap between the facet 2804 and the beam 2808 is illustrated by the shaded region.

FIG. 28(*b*) illustrates the scenario in which beam of light 2808 totally overlaps receiving facet 2804. In this scenario, the area of overlap is comprised of the entire area of facet 2804. To represent this, facet 2804 is illustrated as being entirely shaded.

FIG. 28(*c*) illustrates the scenario where the beam 2808 illuminates only a portion of receiving facet 2804. In this scenario the area of overlap consists entirely of the area of the beam projected on the facet and thus, this area is illustrated as being shaded in FIG. 28(*c*).

FIG. 28(*d*) illustrates the scenario where beam 2808 and facet 2804 do not overlap one another. In this scenario there is no light from beam 2808 reflected from or refracted by facet 2804.

These four scenarios illustrate the interaction that a beam of light may have with a facet. Because the invention traces a beam of light through its various reflections and refractions in a stone, it is important to know the shape and area of each reflected or refracted beam, and, of course, the direction in which it travels. Spatial domain processing is directed toward determining the common area, or the area of overlap between the beam and the receiving facet (i.e. the shaded area illustrated in FIG. 28). This common area indicates the size and shape of the reflected or refracted beam (the child beam) as it leaves the facet in question.

Figure 29:
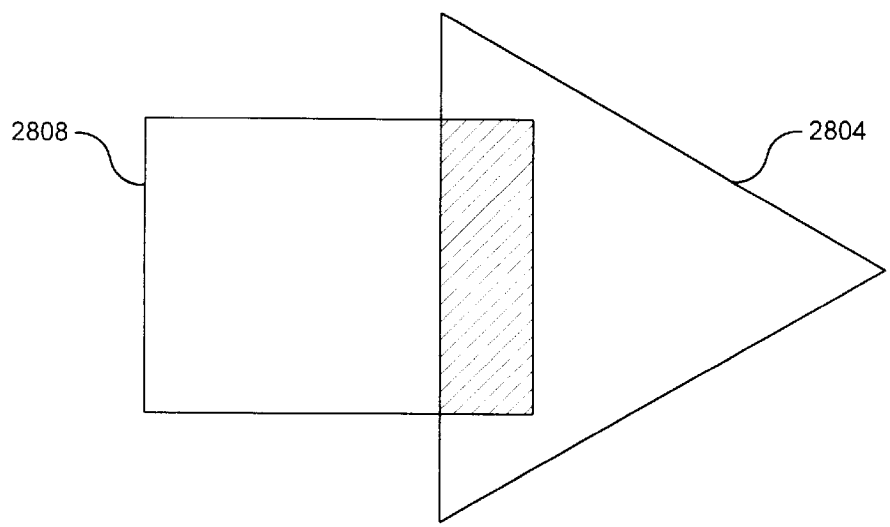
FIGS. 29(a) and 29(b) illustrate scenarios where one or more (but not all) vertices of one boundary lie within the opposite boundary.
Figure 29:
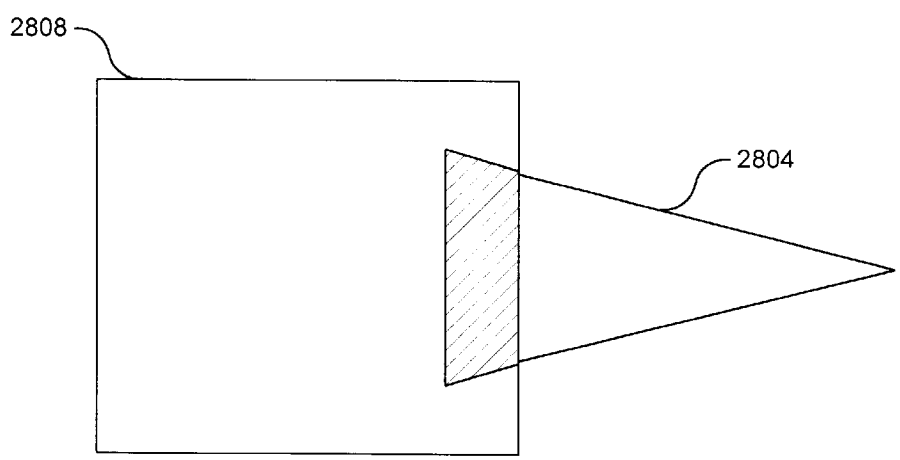

The scenario illustrated in 28(*a*) where the projection of the beam 2808 overlaps the facet 2804 has other variations as illustrated in FIG. 29. FIG. 29 is comprised of FIGS. 29(a) and 29(b). FIG. 29(a) illustrates a scenario where one or more (but not all) vertices of the projection of the beam 2808 lie within the boundaries of the facet 2804. The scenario illustrated in the 29(b) illustrates a scenario where one or more (but not all) of the vertices of facet 2804 are enclosed by the boundaries of the projection of the beam 2808.

Note that while the facet 2804 is illustrated as a triangle, and the projection of the beam 2808 is illustrated as a four sided polygon, it will become apparent to a person skilled in the relevant art after reading this discussion that the principles of the invention can be applied to facets and beams shaped as other n-sided polygons.

Also note that for many gemstones, one side of one or more facets may actually be rounded. An example of when this situation arises is where a facet of a stone has a boundary on the girdle of the stone, and the girdle of the stone is rounded. In this instance, the preferred embodiment of the invention models that boundary of the facet as a single segment or as a plurality of segments to effectively trace the arc. The decision as to how many segments are required to accurately trace the arc can be based upon a tradeoff between the amount of light "lost" by the modeling software, and the increased complexity of using additional segments to define a facet boundary. In this embodiment, light is "lost" in the area of the facet between the plurality of segments which make up the defined boundary and the actual boundary arc. This light is considered lost, because light which impinges on this area it is not considered in computing the energy in a reflection or refraction from that facet.

Figure 30:
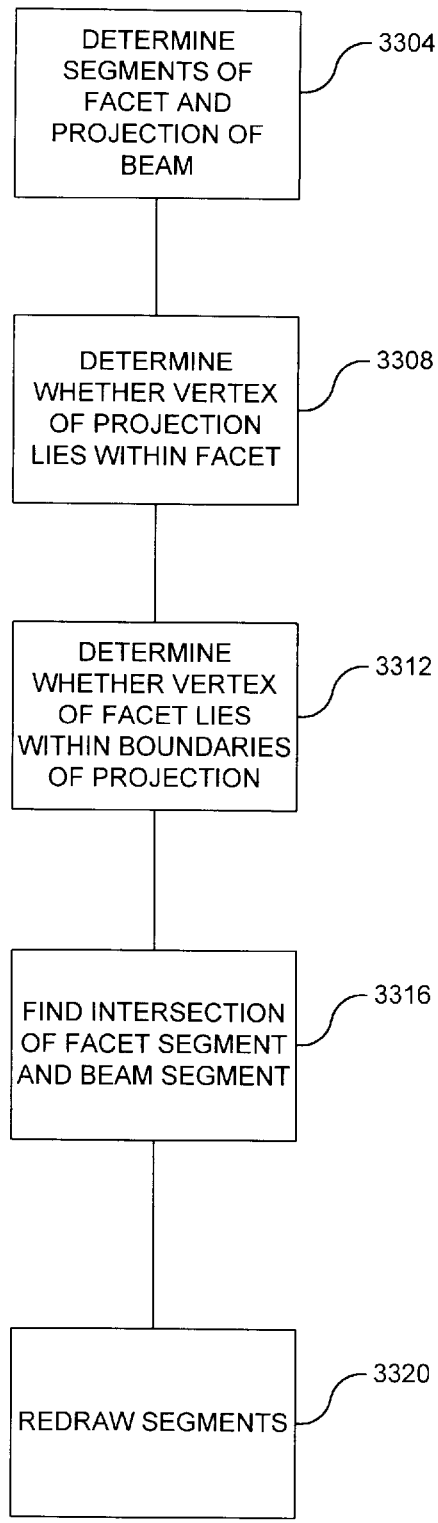
FIG. 30 is an operational flow diagram illustrating an example process for determining boundaries of a child beam as a result of a reflection or refraction of its parent beam from a facet according to one embodiment of the invention.

FIG. 30 is an operational flow diagram illustrating a process for determining boundaries of a child beam as a result of a reflection or refraction of its parent beam from a facet according to one embodiment of the invention. The manner in which this is accomplished is by determining the spatial overlap, or the common area, of the light beam and the receiving facet.

Referring now to FIG. 30 in a step 3004, the segments which define the boundaries of the facet and the projection of the beam onto that facet are determined. In one embodiment the data structure is established such that the beams and facets are defined in terms of their vertices. In this embodiment, step 3004 utilizes a computation to determine the segments from the vertices. In one embodiment, the segments of the both the facet and the projection of the beam onto the facet as determined in step 3004 are stored in a linked list of segments.

Note that in a preferred embodiment as described above, the facets of the stone are defined in terms of their vertices in a global coordinate system. Similarly, the vertices of the beam and the propagation direction of the beam are also stored in terms of this global coordinate system. For ease of processing, in a preferred embodiment, the segments of both the facet and the projection of the beam onto the facet are determined in an arbitrary coordinate system of the facet.

In a step 3008 it is determined whether each vertex of each segment of the projection of the beam lies inside or outside of the facet. This is accomplished by booling each vertex of a segment with the facet boundaries. In one embodiment, this is performed for each segment of the boundary of the projection of the beam to determine whether one, both, or neither end points of that segment lie within the boundary of the facet.

In one embodiment, this is accomplished by taking each value of the coordinate of the vertex in question and substituting these values into the equation of each segment in the boundary of the facet to determine whether there is a intersection between that segment and the value of the coordinate of the vertices.

In a step 3012, it is determined whether each vertex of a facet lies within the boundary of the projection of the beam on that facet. This process is performed for each vertex of each segment of the facet in a manner which is analogous to the manner in which it was determined in step 3008 whether the vertices of the projection of the beam were within the boundary of the facet. Although a number of techniques can be used to determine whether a vertex of a segment is inside or outside a boundary, one example process for performing steps 3008 and 3012 is described in detail below with reference to FIG. 34.

Figure 31:
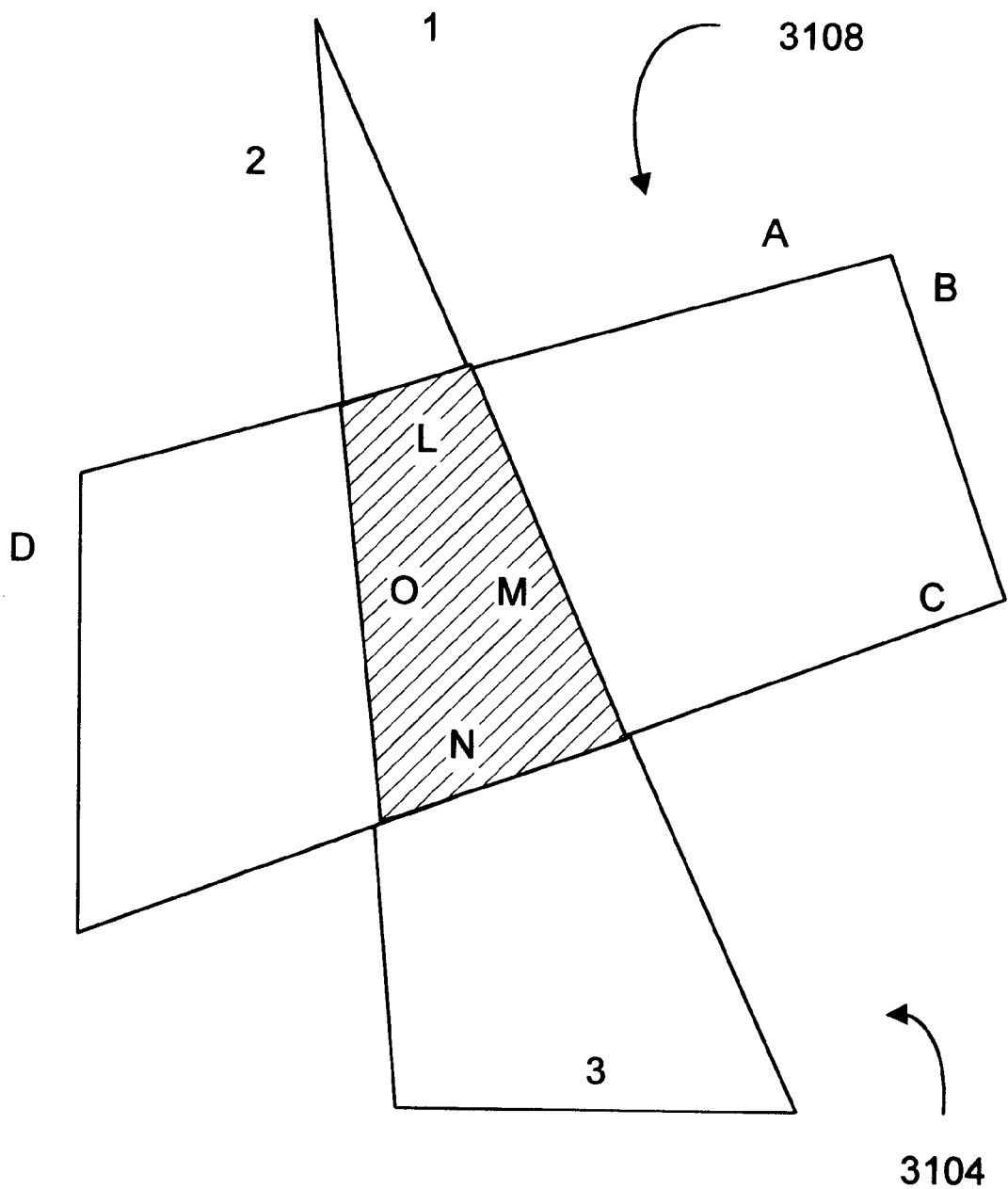
FIG. 31 depicts the intersection of segments of a facet with segments of a beam projection.

In a step 3016, intersections of the segments of the projection of the beam with the segments of the facet are found. If there is a intersection, in a step 3020, this intersection is used to determine the segments that make up the area of overlap. For example, consider the scenario illustrated in FIG. 31. In this scenario, segments 1 and 2 of facet 3104 intersect segments A and C of beam projection 3108.

Thus, in step 3020 the segments are redefined as bolded segments L, M, N, and O. These segments are used to define the overlap area of the projection of the beam onto the receiving facet. In the example illustrated in FIG. 30, segments L, M, N, and O are the segments which define the boundaries of the areas of overlap between the facet 3104 and the projection of the beam 3108 onto facet 3104.

In a step 3024, these segments are processed to determine which segments are adjacent to each other segment. Depending on the data structure used, these segments can be converted to a new linked list of vertices which defines the overlap boundaries.

21.1 Determination of Segments for Facet and Beam Projection Boundaries

Figure 32:
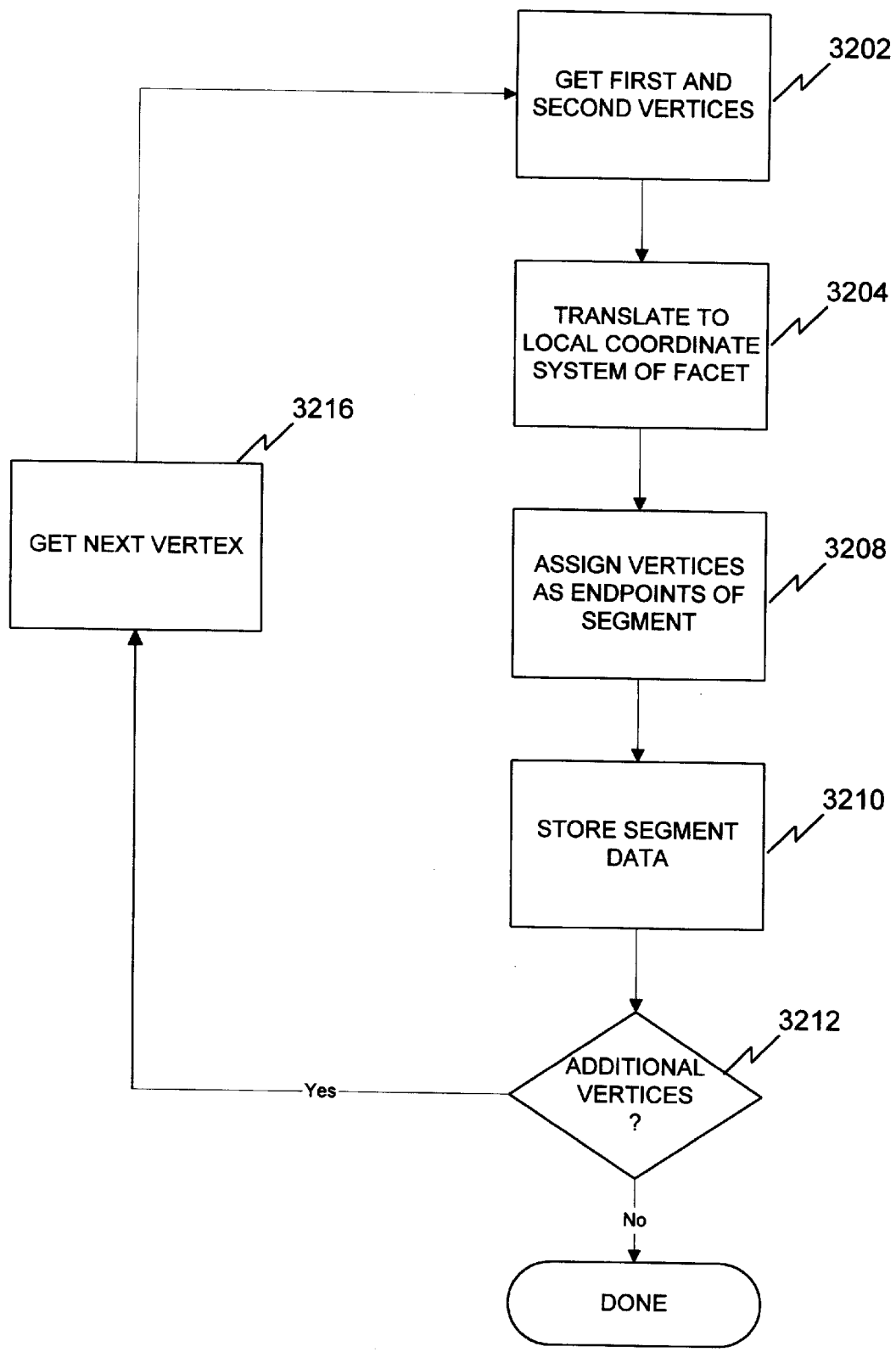
FIG. 32 is an operational flow diagram illustrating an example process for determining the segments of a projection of a beam onto a facet according to one embodiment of the invention.

As stated above, in one embodiment of the invention, the data structure is established such that the facets and the beam projections are defined and stored in terms of their vertices. FIG. 32 is an operational flow diagram illustrating a process for determining the segments of a projection of a beam onto a facet from such vertices. In one embodiment, as described above, the vertices are stored in a linked list.

In a step 3202, the first and second vertices in the linked list are retrieved. These vertices define the first segment of the projection of the beam. In a step 3204, these vertices are translated to the coordinate system of the facet. This is done so that the segments of both the facet and the projection of the beam can be expressed and manipulated in the same coordinate system.

In a step 3208, the translated vertices are assigned as the end points of the first segment of the projection of the beam. In a step 3210, the segment data defined by the two end points is stored in memory.

If there are additional vertices that define the projection of the beam, these vertices are retrieved and the operation repeats at step 3204. This is illustrated by decision block 3212 and step 3216. This process is repeated for each adjacent pair of vertices of the beam projection being evaluated. In the embodiment where the vertices are stored in a linked list, only one new vertex needs to be retrieved in step 3216. This is because, in this embodiment, the second vertex of the previous segment is actually the first vertex of the next segment.

Note that in one embodiment, the vertices of the facets and of the beam boundaries are described in terms of a world or global coordinate system. In this embodiment, these vertices are translated into a local coordinate system of the facet as described with reference to step 3204. In the preferred embodiment, the local coordinate system of the facet is defined such that such that two axes of the local coordinate system lie in the plane of the facet and the third axis of the local coordinate system is perpendicular to this plane. For ease of description, the axes of the arbitrary coordinate system of the facet which lie in the plane of the facet are described in this document as being the x and y axes. Following this convention, the z axis in this arbitrary coordinate system is perpendicular to the plane of the facet.

Figure 33:
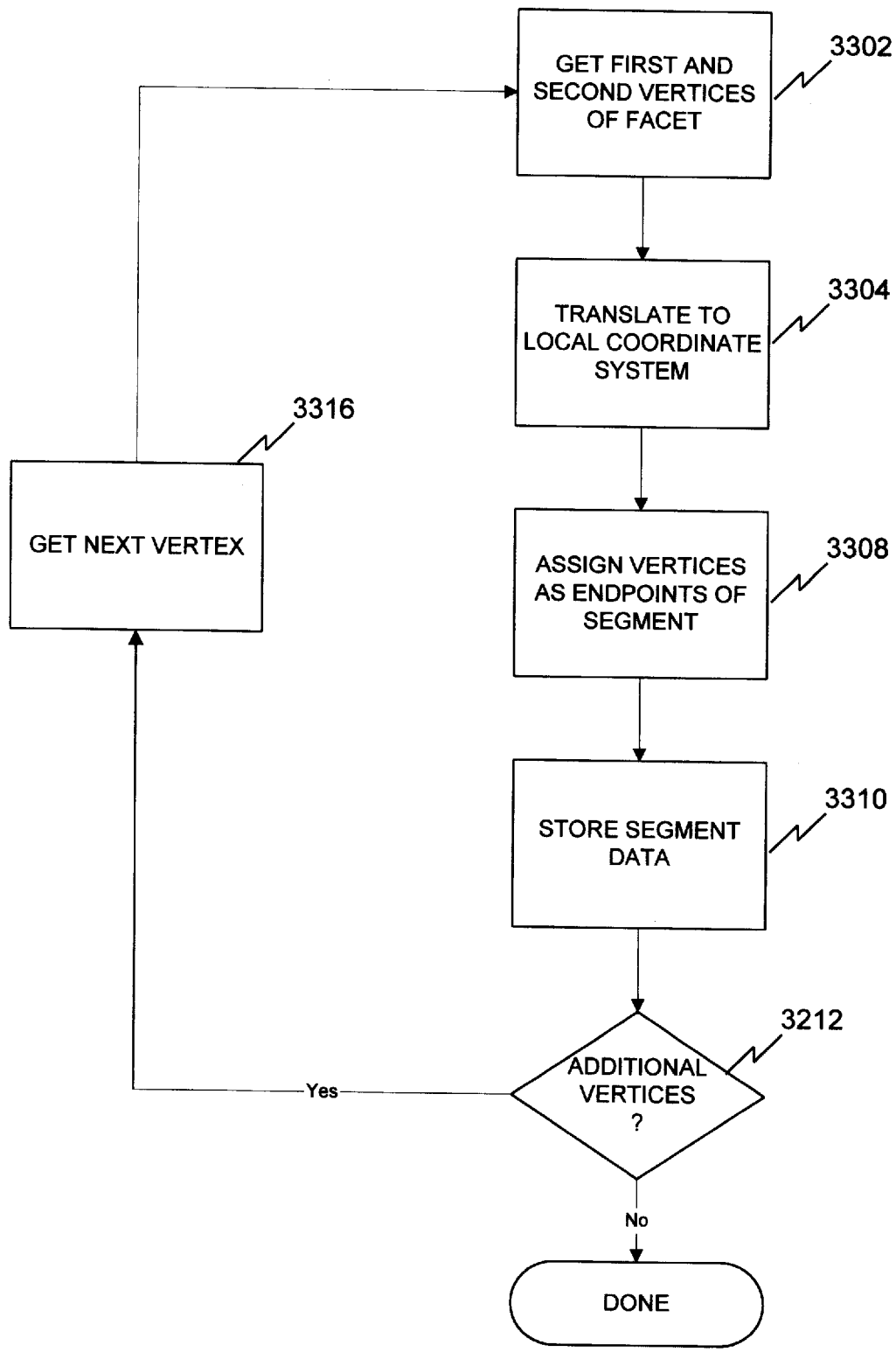
FIG. 33 is an operational flow diagram illustrating repetition of a process for vertices of a facet to determine facet segments according to one embodiment of the invention.

The repetition of this process for the vertices of the facet to determine the facet segments is illustrated in FIG. 33. In a step 3302, the first and second vertices in the linked list of vertices of the facet are retrieved. In a step 3304, these vertices are translated to the coordinate system of the facet.

In a step 3308, the translated vertices are assigned as the end points of the first segment of the facet. In a step 3310, the segment data defined by the two end points is stored in memory.

If there are additional vertices that define the facet, these vertices are retrieved and the operation repeats at step 3204. This is illustrated by decision block 3212 and step 3216. This process is repeated for each adjacent pair of vertices of the facet being evaluated.

As a result of this process, the receiving facet and the projection of the beam onto that facet are each described in terms of the segments which make up their boundaries.

One advantage of translating the facet vertices into the local coordinate system of the facet (step 3304) and the vertices of the beam projection into the same coordinate system (step 3304) is that the z component of each of these vertices is 0. As such, the boolean and algebraic computations that are performed in determining the spatial overlap of the projection of the beam with the boundaries of the facet are greatly simplified.

21.2 Determine Whether Vertices are Inside or Outside of Opposite Boundary

As described above with reference to FIG. 30, in a step 3008 the invention determines whether each of the vertices of a segment defining the boundary of the projection of the beam is within the boundaries of the receiving facet. Similarly, step 3012 determines whether each vertex of a segment defining the facet boundary lies within the boundary of the beam projected on that facet. The manner in which such a determination can be made according to one embodiment of the invention is now described in greater detail. After reading this description, it will become apparent to one skilled in the relevant art after reading this description, how this can be accomplished using alternative processes.

Figure 34:
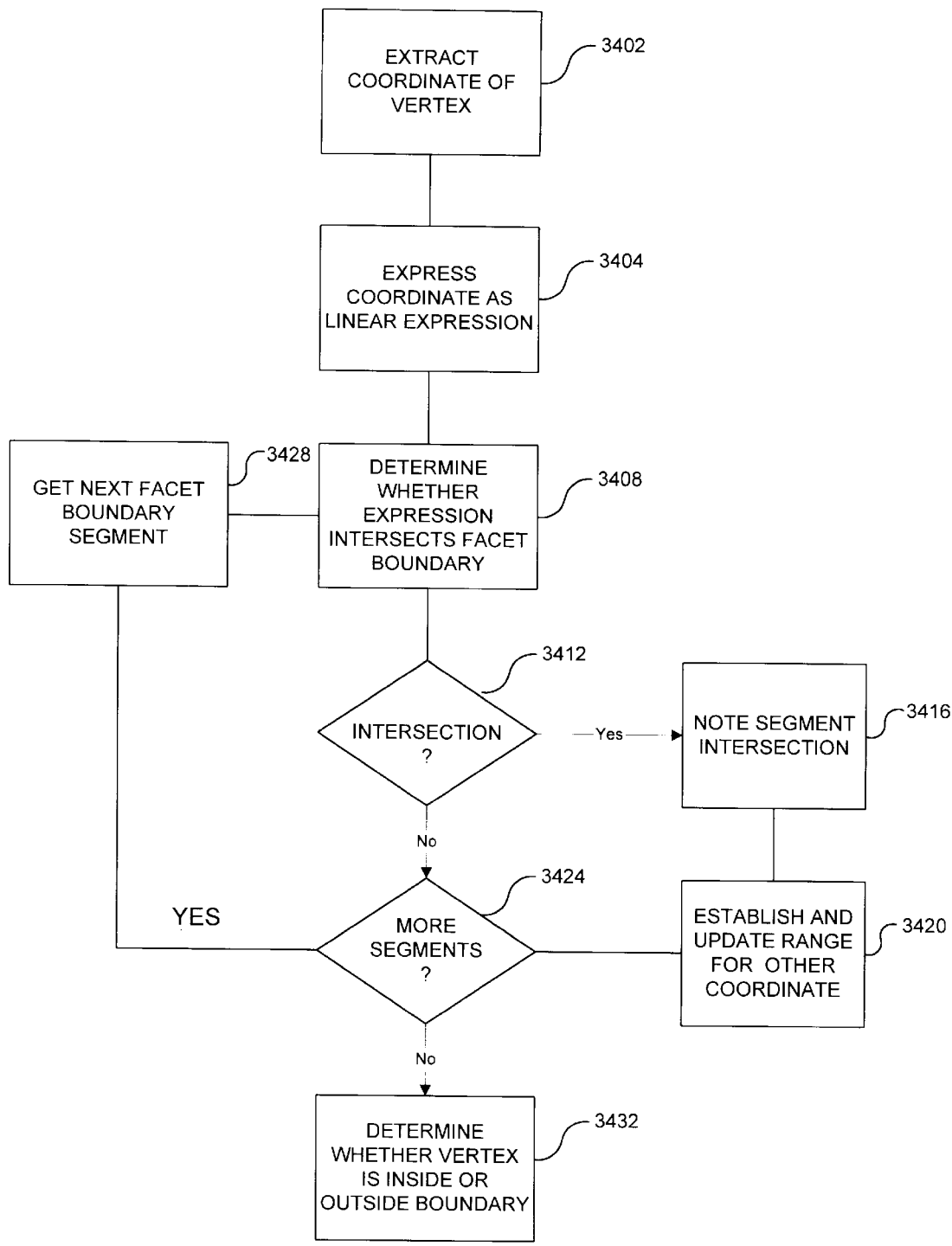
FIG. 34 is an operational flow diagram illustrating an example process for determining whether a vertex of the boundary of the projection of the beam lies within the boundaries of the receiving facet according to one embodiment of the invention.

FIG. 34 is an operational flow diagram illustrating a process for determining whether a vertex of the boundary of the projection of the beam lies within the boundaries of the receiving facet according to one embodiment of the invention. Because the vertices of the projection of the beam and the vertices of the receiving facet are all described in the coordinate system of the facet, only two coordinates of the vertices (namely, the x and y coordinates) need to be considered in the preferred embodiment.

In a step 3402, one of the coordinates of a first vertex of the projection of the beam is chosen. For example, according to one convention, the x coordinate of the vertex is chosen. In step 3404, this x coordinate of the first vertex is expressed as a linear expression. In other words, if the (x,y) coordinates of the first vertex are (3,2), then the linear expression for the chosen x coordinate is x=3. Thus, this represents a line in the x,y plane which is parallel to they axis, and intersects the x axis at x=3.

In a step 3408, this linear expression is examined to determine whether it intersects a segment which makes up the boundary of the receiving facet. In one embodiment, this is accomplished by determining maximum and minimum x values of the facet boundary segment from the x coordinates of that segment's vertices. And comparing that with the x value of the vertex's coordinate. If the value of x is within the bounds defined by the maximum and minimum values, the expression intersects the facet boundary segment in question. If the linear expression intersects the facet boundary segment in question, this result is stored. This is illustrated by steps 3412 and 3416.

In a step 3420, if there is an intersection between the linear expression and the facet boundary segment in question, the other coordinate is checked to determine whether it is within maximum and minimum bounds for that coordinate determined by the intersecting facet boundary segment. Note that in the illustrated embodiment, if there is no intersection of the x coordinate with the segment in question, the other coordinate (i.e., they coordinate) does not need to be checked.

Steps 3408 and 3412, and possibly 3416 and 3420 (depending on the results of the test in 3412), are repeated for each segment of the facet boundary to determine whether the linear expression determined in step 3404 intersects each of those facet boundary segments and whether the other coordinate of the vertex lies within minimum and maximum bounds established by the intersected segments. This is illustrated by decision step 3424, which determines whether there are any untested segments of the facet boundary, and step 3428, which retrieves the next untested segment of the facet boundary.

Once all the segments of the facet boundary have been tested, the vertex is evaluated to determine whether it is inside or outside the facet boundary. This is illustrated by a step 3432.

Note that in some applications (such as the gemstone application described herein), the polygons which describe the projection of the beam and the facet boundaries will not have any obtuse angles. That is, the perimeters of the facets are all convex shapes. Also, each of these boundaries will be closed boundaries such that the sum of their angles equals 360°. Therefore, if the linear expression for a vertex intersects one segment boundary of the receiving facet, it will necessarily intersect a second segment of the facet boundary.

Figure 35:
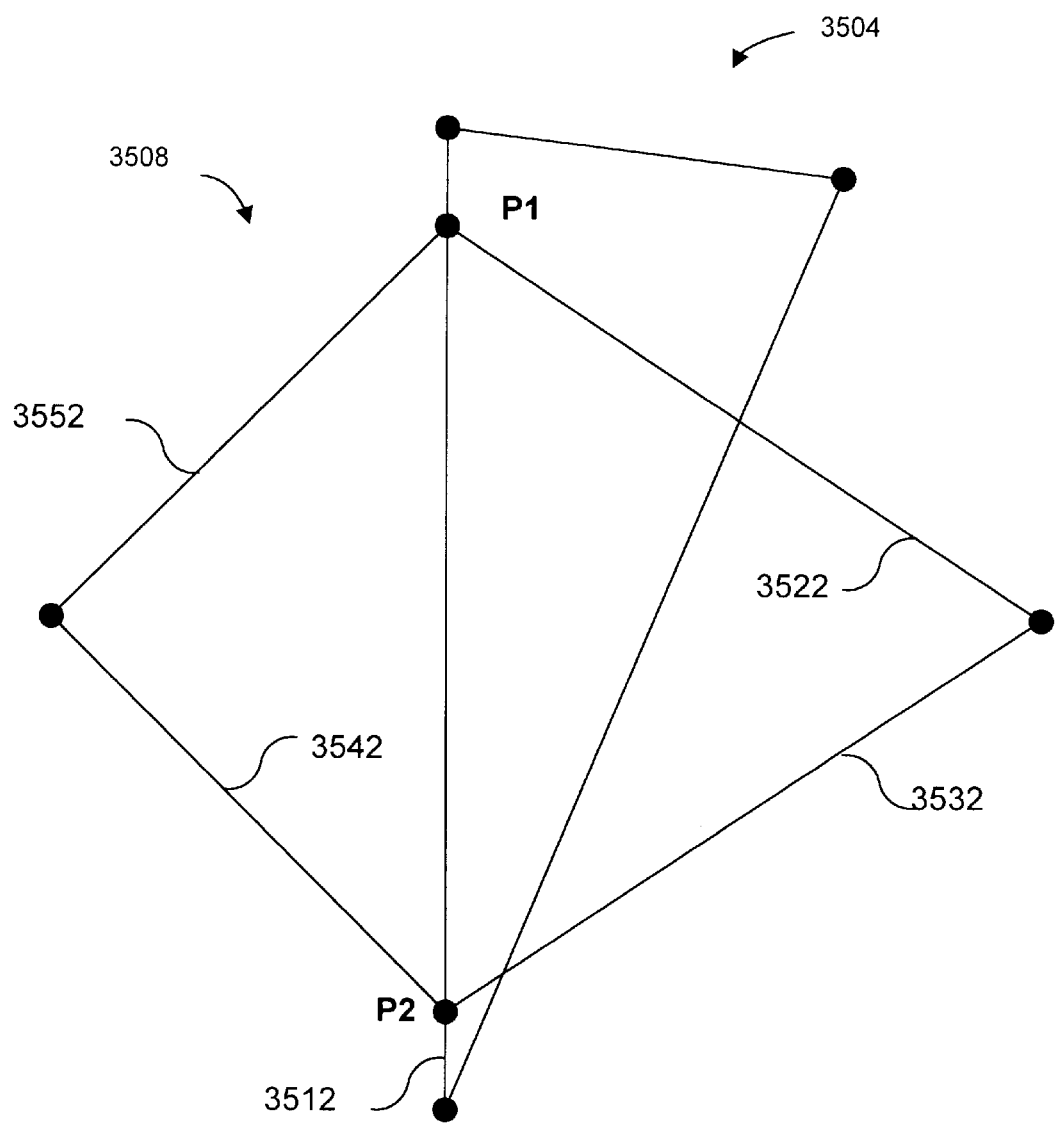
FIG. 35 illustrates a beam projection boundary overlapping a facet boundary.

Additionally, because the linear expression will intersect the boundary at two points, and because these two points can be coincident with two vertices of the boundary, the maximum number of segments intersected by the linear expression is 4. This is best illustrated by a simple example. FIG. 35 is a diagram illustrating such an example. FIG. 35 illustrates a beam projection boundary 3508 overlapping a facet boundary 3504. Segment Y.9.12 of facet boundary 3504 intersects four segments of beam projection boundary 3508 by intersecting vertices P1 and P2. This is because vertex P1 is a part of segments 3552 and 3542, and vertex P2 is a part of segments 3522 and 3532.

Figure 36:
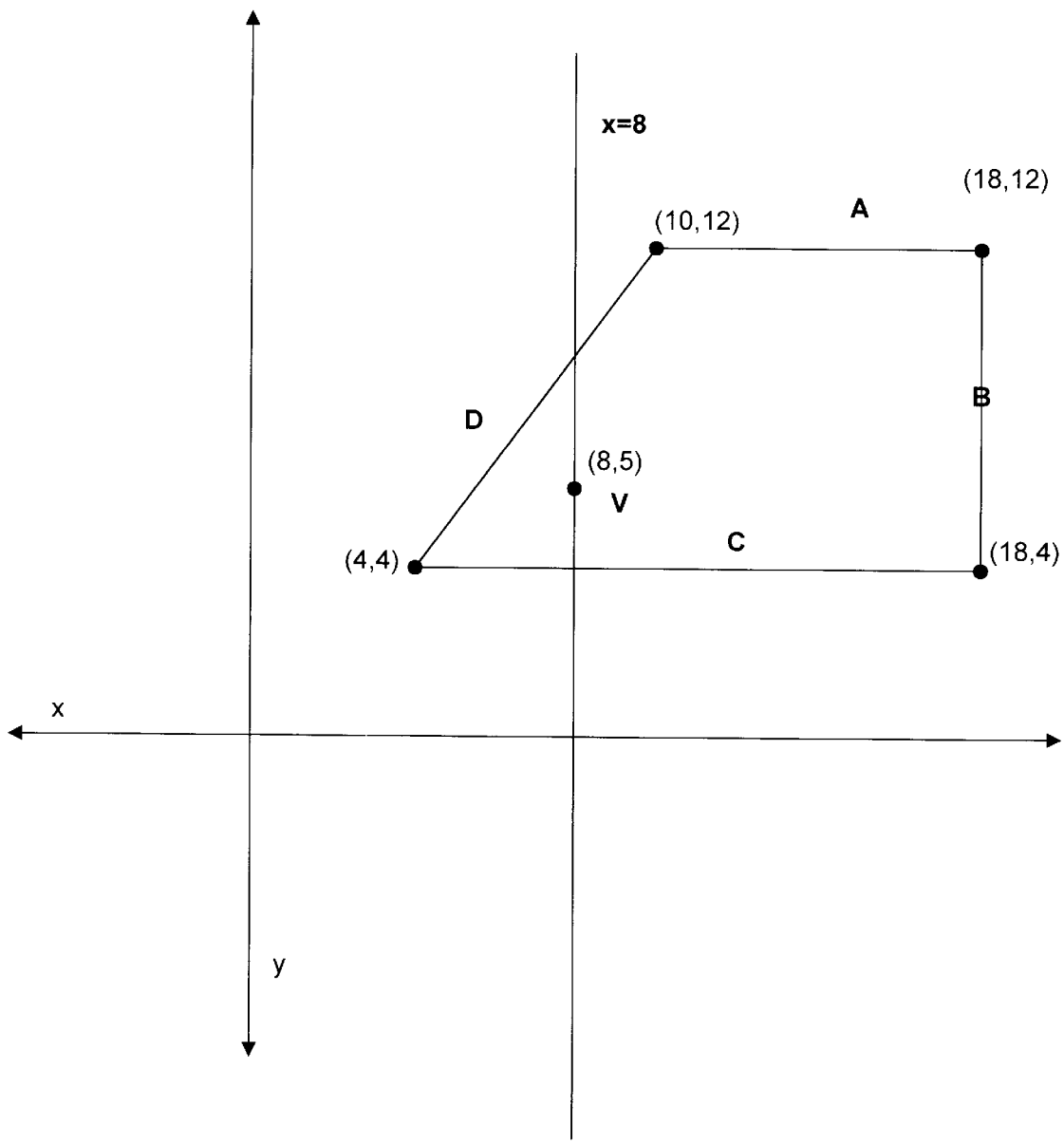
FIG. 36 is a diagram illustrating an example of a possible scenario where a vertex of a beam projection lies within the boundaries of a facet.

FIG. 36 is a diagram illustrating an example of a possible scenario where a vertex V of a beam projection lies within the boundaries A, B, C, D of a facet 3602. In this example, vertex V has the (x,y) coordinates (8, 5). From viewing FIG. 36, it is readily apparent that vertex V lies within the boundaries of facet 3602. The process described in FIG. 34 is now described in terms of this example scenario to further illustrate the process.

As described above, in a step 3402, the coordinate of vertex V is extracted. In the embodiment described, it is the x coordinate which is extracted. In this case, the x coordinate of vertex V is 8. In an alternative embodiment, the y coordinate could is extracted first, and the x coordinate evaluated in step 3420.

In a step 3404, this coordinate is expressed as a linear expression x=8. In steps 3408 it is determined whether this linear expression x=8 intersects the facet boundary segment in question. For the purpose of this example, the first facet boundary segment examined is segment A. Segment A is described by the expression y=12 for $10 \leq X, \leq 18$; and y is undefined for all other values of x. Thus, the linear expression x=8 does not intersect segment A.

Therefore, if there are more segments in the facet boundary, the next segment is retrieved as illustrated by steps 3424, and 3428. For the purpose of this example, the next segment retrieved is segment B.

Segment B is described by the expression x=18. Because segment B is parallel to the linear expression x=8, linear expression x=8 does not intersect segment B. Note that in the preferred embodiment, even if segment B is described by the expression x=8 (i.e., even if segment B is coincident with the linear expression), this is considered not to be an intersection.

Therefore, if there are more segments in the facet boundary, the next segment is retrieved as illustrated by steps 3424, and 3428. For the purpose of this example, the next segment retrieved is segment c. Segment C is defined by the expression y=4 for $4 \leq x, \leq 18$. Segment C is undefined for all other values of x. Therefore, the linear expression x=8 intersects segment C. Thus, in step 3416, segment C is noted as intersecting the expression. In a step 3420, they coordinate is used to define a range of y values.

In this example, there is one more segment in the facet boundary. That is segment D. Thus, segment D is retrieved as illustrated by steps 3424, and 3428. Segment D is given by the expression x=y for $4 \leq x, \leq 10$ and $4 \leq y, \leq 12$. Thus, linear expression x=8 intersects segment D. Thus, in step 3416, segment D is noted as intersecting the expression. In a step 3420, the y coordinate is used to further define the range of y values.

Because this is the last segment, the process moves to step 3432 where it is determined whether the vertex lies within the boundary of the facet. Because linear expression x=8 intersects segments C and D, there is a possibility that vertex V (8, 5) lies within the boundary defined by segments A, B, C and D. However, there is also a probability that the vertex V may lie outside of this boundary. To determine whether vertex V lies within the boundary, range of y values (e.g., maximum and minimum values of y) determined for segments C and D in step 3420 are examined to determine whether the y value of the coordinate lies within the determined range. Note that in the example illustrated, the range of y values is given by the minimum value of 4 and the maximum value of 8 (the intersection of the linear expression with segment D).

Figure 37:
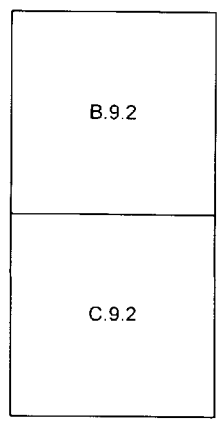
FIG. 37 is an operational flow diagram illustrating an example embodiment for implementing a process for determining whether a vertex is inside or outside an opposite boundary according to one embodiment of the invention.
Figure 38:
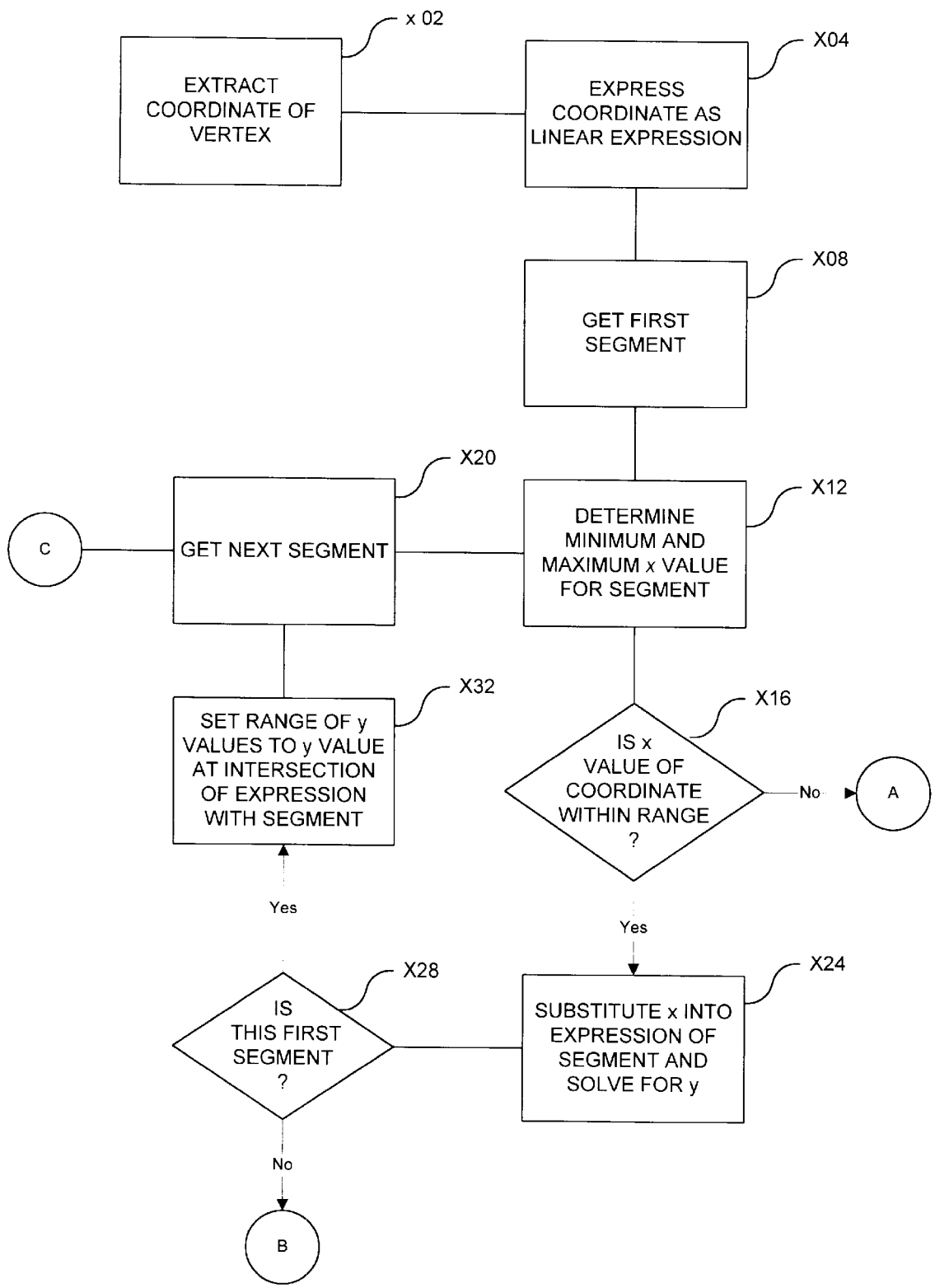
FIG. 38 is an operational flow diagram illustrating an example embodiment for implementing a process for determining whether a vertex is inside or outside an opposite boundary according to one embodiment of the invention.
Figure 39:
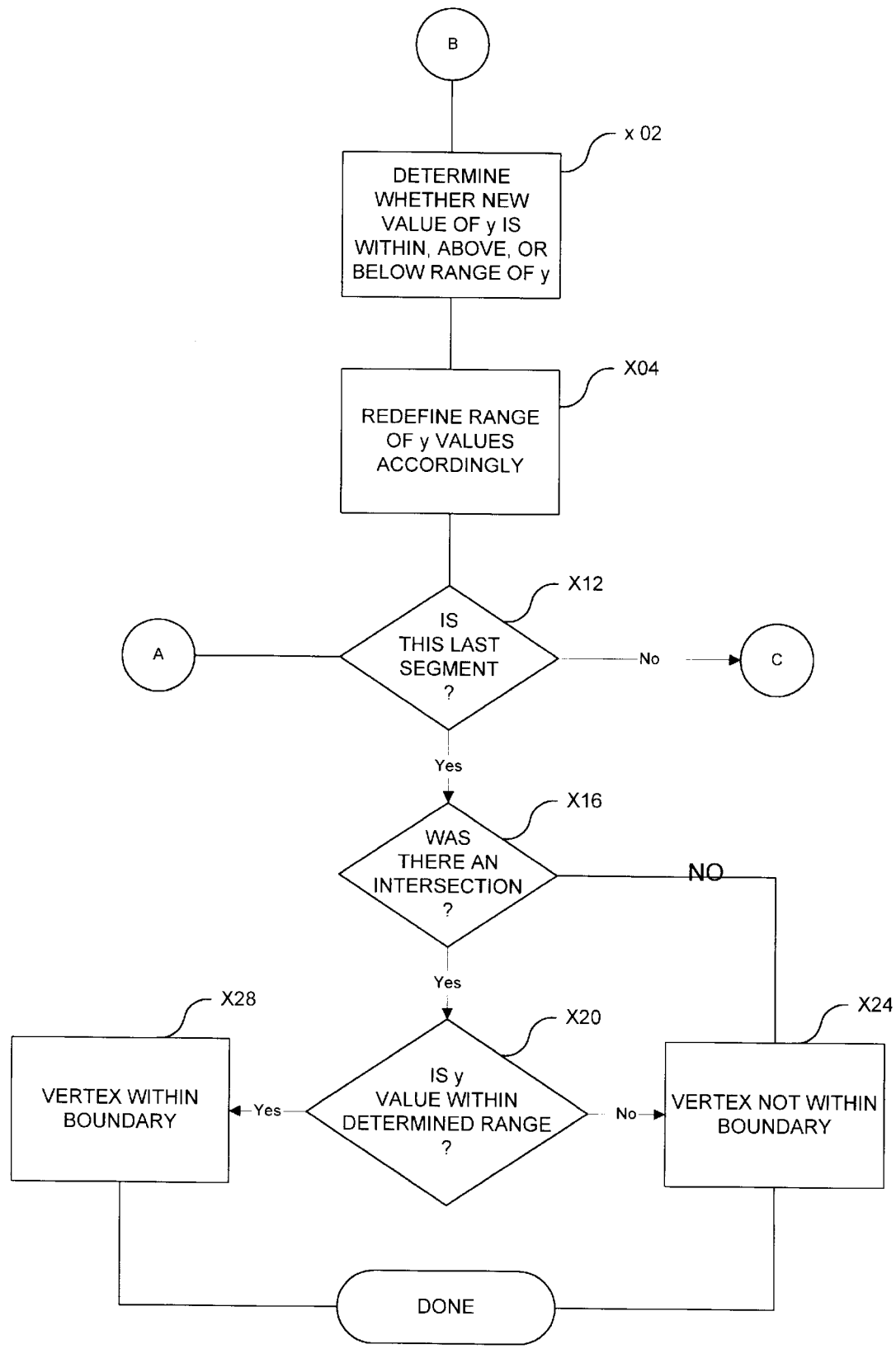
FIG. 39 is an operational flow diagram illustrating an example embodiment for implementing a process for determining whether a vertex is inside or outside an opposite boundary according to one embodiment of the invention.

FIG. 37, which comprises FIGS. 38 and 39, is an operational flow diagram illustrating an example embodiment for implementing the process for determining whether a vertex is inside or outside an opposite boundary. The process now described with reference to FIG. 37 is an example embodiment for implementing the process described with reference to FIG. 34. For ease of description, this example embodiment is described in terms of the example illustrated in FIG. 36. More specifically, this example embodiment is described in the context of determining whether vertex V, having (x,y) coordinates (8,5), is inside or outside the boundary defined by segments A, B, C, and D.

In a step 3802, one of the coordinates of the vertex being examined is chosen. In the example embodiment described, this coordinate is the x coordinate. In this example, the x coordinate is 8. In step 3804, the chosen coordinate (the x coordinate in this example) is described as a linear expression. For the example illustrated in FIG. 36, this linear expression is x=8.

In a step 3808, the first segment of the opposite boundary is retrieved. The process can begin with any boundary segment A, B, C, or D. However, for purposes of this discussion, assume the first segment retrieved from the opposite boundary is segment A.

In a step 3812, the maximum and minimum value for the retrieved segment are determined. Thus, if the retrieved segment is segment A, the maximum and minimum x values for this segment are 10 and 18. The maximum and minimum x values for segment B are 18. The maximum and minimum values for segment C are 4 and 18. The maximum and minimum x values for segment D are 4 and 10.

In a step 3816, it is determined whether the x value of the subject vertex is within this range of x values for the segment. As described above with reference to step 3812, the range of x values for segment A is 10 through 18. Because the x value of the subject vertex is 8, it is not within this determined range. In other words, the linear expression x=8 does not intersect segment A.

Therefore, the process continues to step 3912 where it is determined whether the segment being evaluated is the last segment of the opposite boundary. In other words, it is determined whether each of the other segments of the opposite boundary have already been evaluated using this process described in FIG. 37. If the current segment is not the last segment (if there are more segments to be evaluated), the operation continues at step 3820 where the next segment to be evaluated is retrieved.

Following the current example as illustrated in FIG. 36, assume the next segment retrieved is segment B. Repeating the process described with reference to steps 3812, 3816, and 3912, it is determined that the minimum and maximum x values for segment B are both 18 and the x value of vertex V (x=8) is not within this range. In other words, the linear expression x=8 does not intersect segment B.

Therefore, because this is not the last segment to be evaluated, the next segment is retrieved in step 3820. Assuming that the next segment retrieved is segment C, in step 3812, the minimum and maximum x values for segment C are determined. Segment C, having vertices (4, 4) and (18,4), has a minimum x value of 4 and a maximum x value of 18. Thus, in step 3816, when evaluated against this range, vertex V having coordinates (8, 5), the coordinate x=8 is within this range. In other words, the linear expression x=8 intersects segment C. Thus, in this iteration the process continues at a step 3824.

In step 3824, the x value of the vertex in question is substituted into the expression of the current segment and the expression is solved for y. In terms of the current example, the x value, x=8, is substituted into the expression of segment C. Segment C is defined by the expression y=4, for values of x between 4 and 18. Solving this expression for y yields a value of 4.

In a step 3828, it is determined whether the current segment is the first segment in this process for which there was a intersection with the linear expression. Specifically, in terms of the current example being discussed, in step 3828, it is determined whether segment C is the first segment evaluated in this process for which the linear expression x=8 had an intersection. This determination is made because, according to this embodiment, the invention establishes an initial range of y values based on the first intersection and updates this range for subsequent intersections as described below. This range is then ultimately used to determine whether the vertex in question is inside or outside the opposite boundary.

In this example as described herein, segment C is in fact the first segment retrieved for which there was an intersection with the linear expression x=8.

Therefore, the process continues at step 3832 where a range of y values is defined as the y value at the intersection of the linear expression with the segment. In the current example, the linear expression x=8 intersects segment C at the point (8,4). Thus, the range of y values is defined as y=4. In other words, the minimum y value is 4 and the maximum y value is 4.

In the example implementation described above, where the linear expression intersects a first segment, there will be at least an intersection with a second segment. Therefore, it is not necessary to determine at this point in the process whether the current segment is the last segment in the boundary, and the operation continues at step 3820 where the next segment is retrieved. Following the current example illustrated in FIG. 36, the only segment which has not been evaluated is segment D. Therefore, step 3820 retrieves segment D. In a step 3812, the maximum and minimum x values for segment D are determined. Because segment D is defined by the vertices (4, 4) and (10, 12), the maximum x value for segment D is 10 and the minimum x value for segment D is 4.

In step 3816, it is determined whether the x value of vertex V is within this range. Because the value x=8 is within the range of x values for segment D, the operation continues at step 3824. In this step, the x value x=8 is substituted into the expression of segment D, and the expression is solved for y. In the example illustrated in FIG. 36, segment D is defined by the expression x=y. Therefore, substituting the vertex's value of x=8 into this expression yields the result y=8.

The process continues at step 3828 where it is determined whether the segment being evaluated is the first segment for which there was an intersection with the linear expression. This time through the loop, however, segment D is the second segment for which there was an intersection. Therefore, the operation continues at a step 3902 where it is determined whether this new value of y is within, above, or below the established range of y. As described above, when evaluating segment C, the range of y was defined by a minimum and maximum value of y=4. The value for y determined with reference to segment D is y=8. This value of 8 is above the range determined for step C. Therefore, in a step 3904 the range of y values is redefined to have a minimum y=4 and a maximum y=8.

Accordingly, had the result in the substitution in step 3824 been a value less than the established range for y (for example, had this resulted in a value of y=3) the new range defined in step 3904 would have a maximum value of y=4 and the value determined in step 3824 for the current segment as the new minimum value (in the example stated above y=3).

In a step 3912, it is determined whether the current segment is the last segment to be evaluated. Departing from the example in FIG. 36, assume there are additional segments to be evaluated. In this scenario, the operation continues at step 3820. If there is a third segment which intersects the linear expression, the vertex's value for x is substituted into the expression for this segment to determine the new value y. Because our current range is a minimum y=4 and a maximum y=8, this latest value for y is evaluated to determine whether it is above, below or within this range. If it is within this range, the minimum and maximum values for y are not changed. If it is above this range, it becomes the new maximum value for the range. Likewise, if it is below the range, it becomes the new minimum value for the range.

Returning to the example of FIG. 36, because segment D is the last segment for evaluation, the process continues at step 3916 where it is determined whether there was an intersection of the linear expression with any of the segments of the boundary. As described above, in the current example, the linear expression x=8 intersects two segments: segment C, and segment D.

Thus, in this example, the operation continues at step 3920. However, before describing step 3920, the scenario where there is no intersection is first described. If each segment of the boundary is evaluated in accordance with steps 3812, 3816, 3912 and 3820, and no intersection is found, this indicates that the vertex in question was not within the opposite boundary. This is illustrated in step 3924.

Returning to the current example, it was determined above that the linear expression x=8 intersected segments C and D. Therefore, the process continues at step 3920 where it is determined whether the y value of the vertex in question is within the range determined for y values. For the vertex (8, 5) having ay value of 5, it is determined whether this value is within the range of y values determined in the above process. Specifically, in the current example, in a step 3904, the range of y values was finally defined as having a minimum y=4 and a maximum y=8. Therefore, in this example, the vertex's y value of y=5 is within this range.

Therefore, the process finally determines that the vertex is within the opposite boundary as illustrated by step 3928. If the y value for the vertex is not within this defined range, the vertex is identified as not being within the opposite as illustrated by step 3924. Thus, for the vertex in question, it is known whether this vertex lies inside or outside the opposite boundary.

Figure 40:
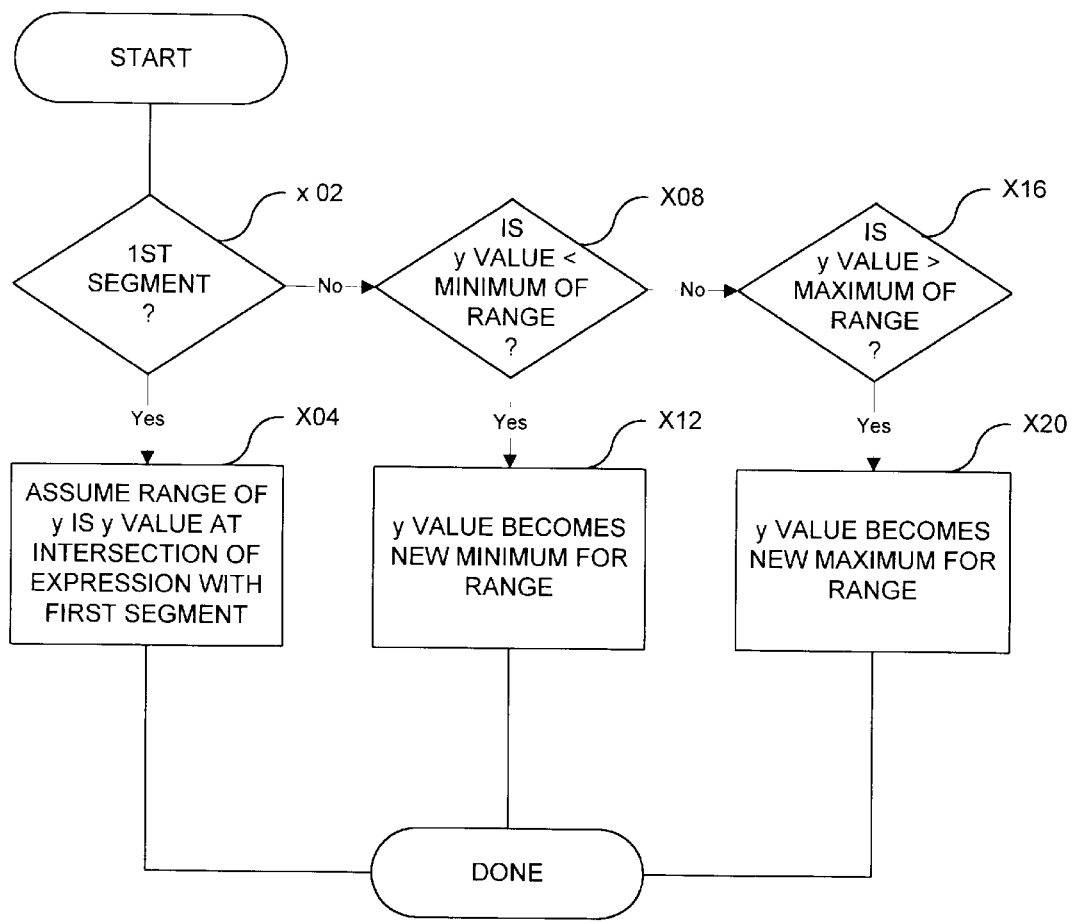
FIG. 40 is an operational flow diagram illustrating an example process by which the range of y values is determined according to one embodiment of the invention.

FIG. 40 is an operational flow diagram illustrating a process by which the range of y values is determined according to one embodiment of the invention. More specifically, FIG. 40 is an operational flow diagram illustrating one example process for carrying out steps 3828, 3832, 3902 and 3904.

In a step 4002, it is determined whether the segment being evaluated is the first segment which intersected the linear expression. If this is the first segment, it is assumed that the range of y values is the y value at the intersection of that segment with the linear expression. This occurs in a step 3404. Steps 4002 and 4004 can be carried out as described above with reference to steps 3828 and 3832.

If, on the other hand, in a step 4002 it is determined that the segment being evaluated is not the first segment for which there was an intersection, the range of y values is updated. As described above, the range of y value is updated based on whether the current y value (determined in step 3824) is above or below the established range. For the second intersection, the established range is a single value. For example, after processing segment C in the above example, the range of values is a minimum y=4 and a maximum y=4. If the new y value is below this range, decision step 4008 is true and processing continues at step 4012 where this y value becomes the new minimum for the range.

If, for example, the current range of y values is a minimum y=3 and a maximum y=7, and the new y value determined in step 3824 is y=1, the new range of values is y=1 for the minimum y value, and y=7 for the maximum y value. On the other hand, if the y value determined is not less than the minimum of the range, decision step 4008 is false and it is determined whether the y value is greater than the maximum of the range in step 4016. If the new y value is greater than the maximum for the range, this new y value becomes the new maximum for the range. For example, given a current range having a minimum value of y=3, and a maximum y=7, if the new y value is y=12, the range is redefined in step 4020 as minimum y=3 and maximum y=12.

If the y value determined in step 3824 is neither less than the minimum value of the range or greater than the maximum value of the range it is within the range (or equal to the range where the range is a single value). In this case, the range does not need to be updated.

Figure 41:
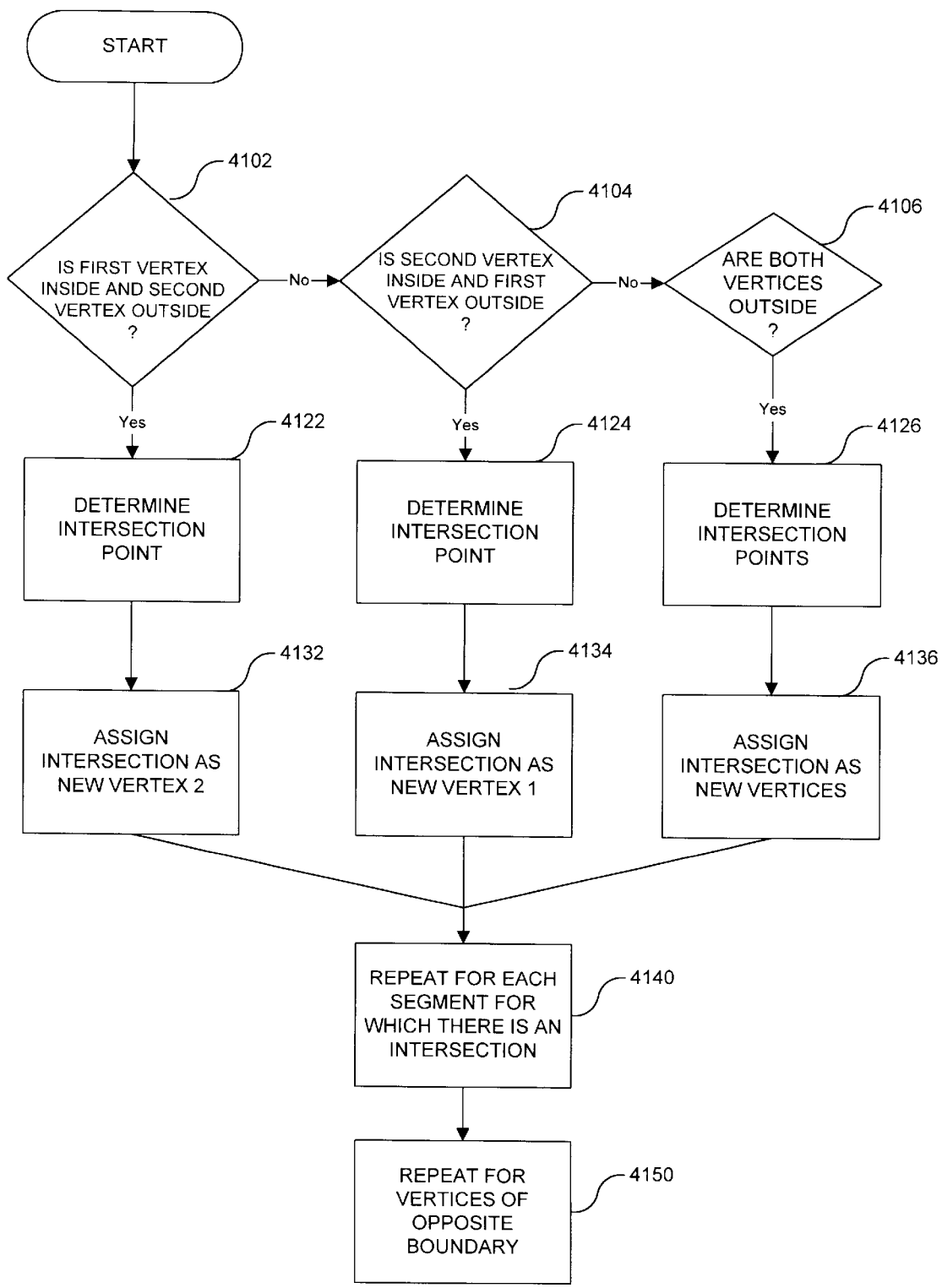
FIG. 41 describes an example process for assigning vertices to segments of the overlap boundary according to one embodiment of the invention.
Figure 42:
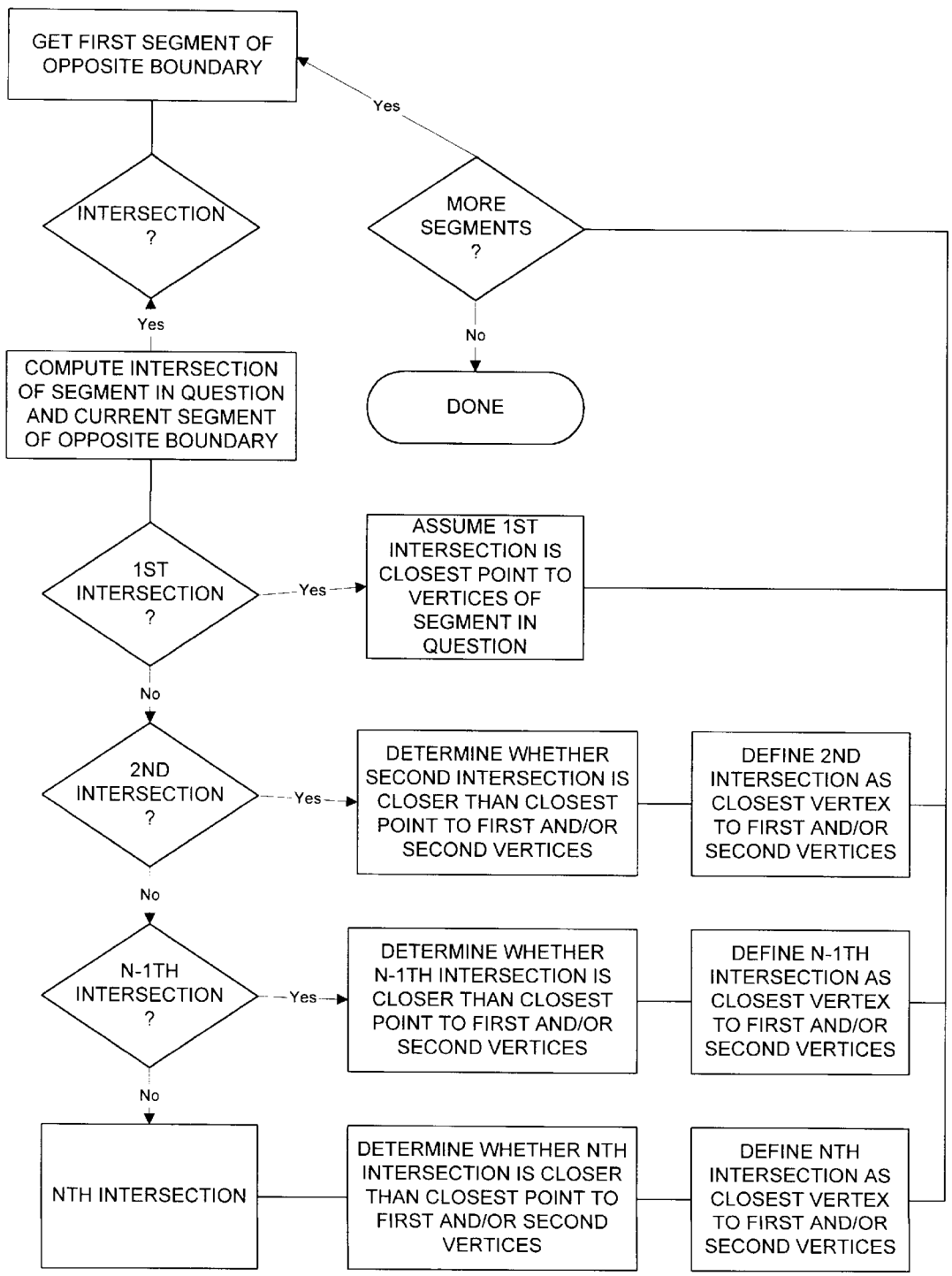
FIG. 42 is an operational flow diagram illustrating one embodiment for determining which intersection point to assign as a vertex of a segment of the overlap boundary.

FIG. 41 describes a process for assigning vertices to the segments of the overlap boundary according to one embodiment of the invention. As described above, this process is done for each segment of one boundary by determining its intersection points with one or more segments of the opposite boundary, and determining which of these intersection points will replace which vertex of the original segment to result in the overlap segment. FIG. 42 is an operational flow diagram illustrating one embodiment for determining which intersection point to assign as a vertex of a segment of the overlap boundary.

Generally speaking, the process works by evaluating the intersection points of the segments of the beam projection boundary with the segments of the facet boundary to determine new segment endpoints which make up the overlap boundary. In the preferred embodiment, where a first vertex of an original segment is outside the opposite boundary, an intersection point on the segment which is closest to the first vertex of that segment becomes the new first vertex of the overlap segment. Similarly, if a first vertex of an original segment is outside the opposite boundary, an intersection point on the segment which is closest to the second vertex of the original segment becomes the new second vertex of the overlap segment.

For a given segment in one boundary for which there is overlap (refer to as subject segment), the process described below with reference to FIG. 42 is performed for each segment of the opposite boundary for which there is overlap to determine which intersection point defines the vertex of the overlap boundary for the subject segment. In a step 4202, the first segment of the opposite boundary is retrieved. For example, if a segment of the facet boundary is being evaluated to determine new vertices which will define the overlap segment, a segment of the beam projection boundary is retrieved. For ease of discussion, the segment being evaluated is referred to as the subject segment, and the retrieved segment of the opposite boundary is referred to as the first segment of the opposite boundary.

In a step 4204, it is determined whether the first segment of the opposite boundary intersects the subject segment. If it does not intersect the subject segment, the next segment of the opposite boundary is retrieved in step 4202.

If, on the other hand, in step 4204 it is determined that the retrieved segment intersects the subject segment, the point of intersection is determined in a step 4208. If this is the first intersection point found between the subject segment and a segment of the opposite boundary, the invention assumes that this first intersection point is the closest point to the vertices of the subject segment as illustrated by decision step 4212 and step 4216. That is, this intersection point is defined as the closest intersection point to the original first vertex of the subject segment and the closest intersection point to the original second vertex of the subject segment.

Now that an assumption has been made that the found intersection point is the closest point to both the first and second vertices of the subject segment, if there are more segments of the opposite boundary to be evaluated, the next segment of the opposite boundary is retrieved. This is illustrated by decision step 4250 and step 4202.

If the next retrieved segment of the opposite boundary has an intersection with the subject segment, that intersection is computed in step 4208. If this is the second intersection point found for the subject segment, the invention determines whether the second intersection is closer to one or both of the first vertex in the second vertex of the subject segment than was the first intersection point. This is illustrated by decision step 4218 and process step 4220. If this second intersection point is closer to either the first and/or the second vertex of the subject segment than was the first intersection point, this second intersection point is defined as the current closest point to that vertex. This is illustrated by a step 4224.

In other words, if the second intersection point is closer to the first vertex of the subject segment, than was the first intersection point, this second intersection point is defined as the closest point to the first vertex of the subject segment. Similarly, if the second intersection point is closer to the second vertex of the subject segment than was the first intersection point, this second intersection point is defined as the closest point to the second vertex of the subject segment.

The process of retrieving a next segment of the opposite boundary and determining whether there is an intersection of that segment with the subject segment is repeated for each segment of the opposite boundary as illustrated by decision step 4250.

Note that each time a new segment is retrieved with an intersection, an intersection point is evaluated to determine whether it is closer to either the first vertex, the second vertex, or both vertices of the subject segment than the previously defined or determined closest intersection point. If so, this new intersection point is defined as the closest vertex to the appropriate one or both of the first and second vertices of the subject segment. This is illustrated by steps 4228, 4232, 4236, 4238, 4242, and 4246.

Note, that as described above, in a preferred implementation each segment of one boundary can have a maximum of four intersections with the opposite boundary. This maximum scenario occurs where the segment of one boundary actually intersects two vertices of the other boundary. Therefore, in this scenario N=4 in steps 4228 through 4246.

The embodiment described above with respect to FIG. 42 is now described with reference to the example scenario illustrated in FIG. 43. This example helps to illustrate this process in one potential example situation. For the purpose of this example, assume that the subject segment is segment FS1 of facet boundary 4304 and that from this segment FS1 the process is determining shortened segment DS1 which is a segment of the overlap facet boundary 4304 and beam projection boundary 4308. Thus, in this example, the "subject segment" is segment FS1 having a first vertex FP1 and a second vertex FP2. In step 4202, a first segment of the opposite boundary (beam projection boundary 4308) is retrieved. For the purpose of this example, this segment is assumed to be segment PS1.

In a step 4204, segment PS1 is evaluated to determine whether intersects subject segment FS1. Because there is no intersection, the next segment is retrieved. For the purpose of this example, the next segment is assumed to be segment PS2. Segment PS2 does in fact intersect subject segment FS1. Therefore, in a step 4308, the intersection point of subject segment FS1 with segment PS2 is determined.

Because this is the first intersection point found for the subject segment, decision step 4212 is true, and in step 4216, this intersection point, point DP2, is defined as the closest point to vertices FP1 and FP2 of subject segment FS1.

Beam projection boundary 4308 is evaluated to determine whether there are more segments as illustrated by decision step 350. As a result, segment PS3 is retrieved. Because there is no intersection of segment PS3 with subject segment FS1, the next and final segment PS4 is retrieved. Because there is an intersection between segment PS4 and subject segment FS1 in step 4208, this intersection point is determined. This intersection point is illustrated in FIG. 43 as point DP1.

Because this intersection point DP1 is the second intersection point of subject segment FS1 with beam projection boundary 4308, decision step 4218 is true. Therefore, in step 4220 it is determined whether point DP1 is closer to vertex FP1 than the previously defined closest point (DP2). Similarly, it is also determined whether point DP1 is closer to point FP2 than the previously defined closest point DP2.

As is apparent from the illustration, point DP1 is in fact closer to point FP1 than DP2, therefore, point DP1 is defined as the new closest vertex to the first vertex of subject segment FS1 (FP1). Because there are no more segments in beam projection boundary 4308 to be evaluated with respect to subject segment FS1, the process of 42 for subject segment for FS1 is completed.

As a result of this process, point DP1 is defined as the closest intersection point to vertex FP1, and intersection point DP2 is defined as the closest intersection point to vertex FP2 along subject segment FS1. Thus, to put this example in the perspective of the process described with respect to FIG. 41, point DP1 would be assigned as the new first vertex of overlap segment DS1 and point DP2 would be defined as the second vertex of overlap segment DS1 in step 4136.

Figure 43:
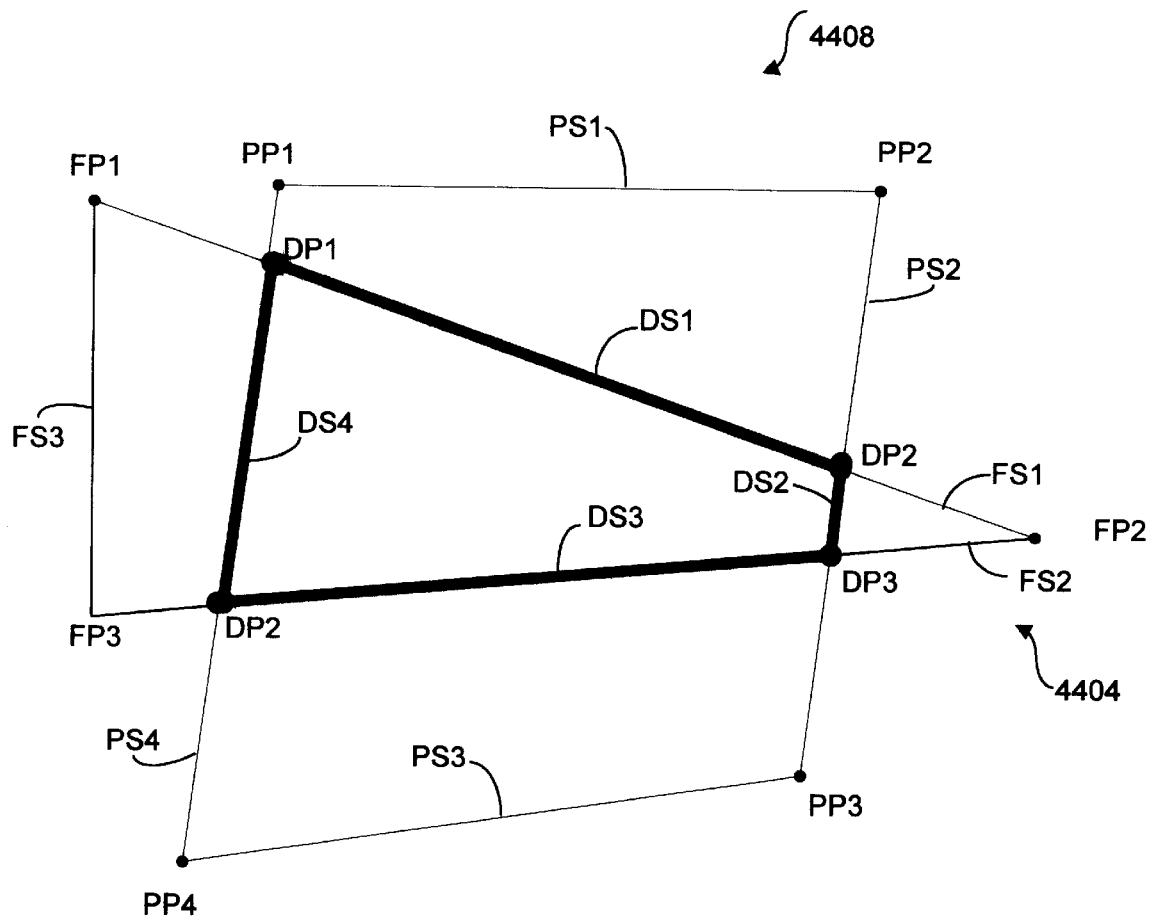
FIG. 43 illustrates an example scenario where segments of each boundary lie outside the opposite boundary, yet the segments overlap.

For the example illustrated in FIG. 43, the process described above with reference FIG. 42 is repeated with segment FS2 as the subject segment. As a result of this process, point DP3 is defined as the closest intersection point along subject segment FS2 to vertex FP2. Similarly, intersection point DP4 is defined as the closest intersection point along segment FS2 to vertex FP3. The process is repeated with segments PS2 and PS4 as the subject segments to determine the intersection points which will be defined as the vertices for overlap segments DS2 and DS4. Thus, as a result of applying the process described with reference to FIG. 42 to the example illustrated in FIG. 43 four overlap segments, DS1, DS2, DS3 and DS4 are defined each having two vertices.

Several of these steps described above make references to determining the distance from an intersection point to a vertex and comparing that with a previously found distance between another intersection point in that vertex to determine which is closest. This determination can be made using simple algebraic computations by computing either true distances between the points in question or by looking at the differences in either the x or y value of the coordinates of those points depending on the orientation of the segment with regard to the axes of the coordinate system.

FIG. 41 is an operational flow diagram illustrating a process for redrawing segments of the reflection boundary and facet boundary as segments defining a boundary for the overlap portion of the projection of the beam with the facet according to one embodiment of the invention. The process illustrated in FIG. 41 utilizes the information obtained regarding whether the vertices of each segment of a boundary are inside or outside the opposite boundary.

More specifically, in steps 3008 and 3012 of FIG. 30, it was determined whether each vertex of the projection of the beam lies within the facet boundary and whether each vertex of the facet lies within the boundary of the projection of the beam. One embodiment for making this determination is described in detail with reference to FIG. 34. This information is used in the embodiment illustrated in FIG. 41 to determine intersection points for facet boundary segments and beam projection segments. Referring now to FIG. 41, given a segment having two vertices, a first vertex and a second vertex, four scenarios are possible: the first vertex of the segment is inside the opposite boundary and the second vertex is outside; the second vertex is inside the opposite boundary and the first vertex is outside the boundary; both vertices of the segment are outside the opposite boundary; and both vertices are inside the opposite boundary. These four scenarios are illustrated in steps 4102, 4104, 4106, and 4108, respectively.

In the first scenario, where the first vertex of the segment is inside the opposite boundary and the second vertex is outside the boundary, there is a single point of intersection where the segment in question intersects a segment of the opposite boundary. In a step 4122, this intersection point is determined. In a step 4132, this intersection point is assigned as new vertex 2. As a result, the segment in question is redefined as a segment having two vertices. The first vertex being the first vertex of the original segment, and the second vertex being the intersection point between the original segment and the segment of the opposite boundary.

In this embodiment, processing of the segment in the second scenario is very similar to that of the segment in the first scenario. Specifically, if the second vertex of the segment in question is inside the opposite boundary, and the first vertex is outside the opposite boundary, as illustrated by decision step 4104, the intersection point of the segment in question with the segment of the opposite boundary is determined in a step 4124. In a step 4134, the segment in question is redefined as having a first vertex being the intersection point between the original segment and the segment of the facet boundary with which it intersects. The second vertex of the redefined segment is the same as the second vertex of the original segment.

In the third scenario where both vertices are outside the opposite boundary, there will be two intersection points. Thus, in a step 4126, if both vertices of the segment in question lie outside the opposite boundary as determined in step 41, the intersection points of this segment with the segments of the opposite boundary are determined. In a step 4136, these intersection points are defined as new vertices 1 and 2 of the redefined segment. In an embodiment where a linked list of vertices are maintained to simplify processing, new vertex 1 is defined as the intersection point closest to the original vertex 1 of the segment in question and new vertex 2 is defined as the intersection point closest to the original vertex 2 of the original segment.

In a step 4140, this process of determining the intersection points and redefining the segment is repeated for each segment of the boundary which intersects the opposite boundary. For example, the process defined by steps 4102 through 4136 is repeated for each segment of the beam projection which intersects one or more segments of the facet boundary.

In a step 4150, the above process is repeated for each segment of the other boundary which intersects one or more segments of its opposite boundary. For example, steps 4102 through 4140 are repeated for each segment of the facet boundary which intersects one or more segments of the beam projection boundary.

As a result of the process described with reference to FIG. 41, a set of segments which describes the overlap boundary of the beam projection with the facet is defined.

Figure 44:
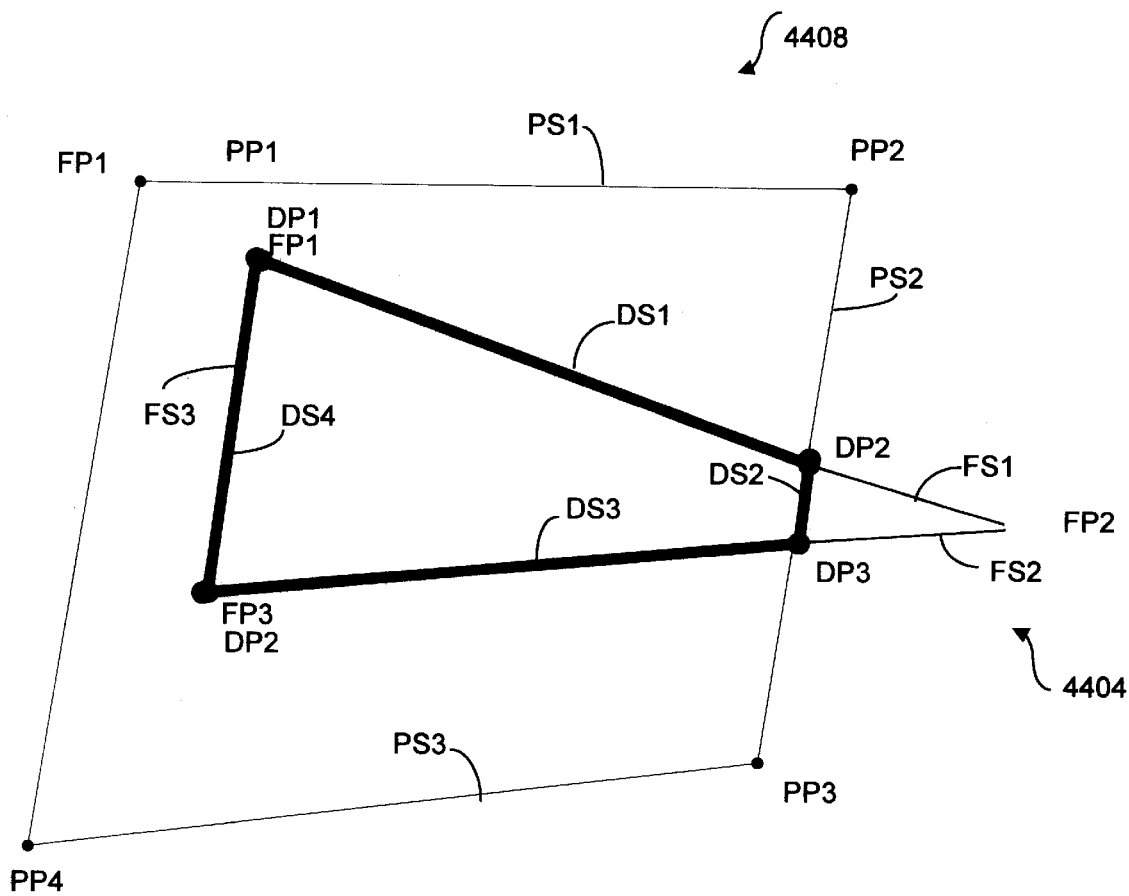
FIG. 44 illustrates a scenario where two of the segments of a facet boundary have one vertex outside of the projection boundary and the other vertex inside the projection boundary.

FIGS. 43 and 44 illustrate two example scenarios of an overlap of a beam projection 4308 with a facet 4304. These scenarios are used to further describe the process of FIG. 41. Reflection boundary 4308 is made up of four segments PS1, PS2, PS3, and PS4. These segments are defined by four vertices PP1, PP2, PP3, and PP4. Facet boundary 4304 is made up of three segments FS1, FS2 and FS3 as defined by three vertices FP1, FP2 and FP3. The overlap boundary is defined by four segments DS1, DS2, DS3, and DS4.

Referring first to FIG. 43, the process described with reference to FIG. 41 is applied to determine the new segments DS1, DS2, DS3, and DS4. In this description, the process is applied to the segments of the facet first and then to the segments of the projection of the beam. As would be apparent to one skilled in the art, this order can be reversed.

One segment of the facet boundary which intersects the beam projection boundary is segment FS1. Both vertices of segment of FS1 (vertices FP1, FP2) lie outside the boundary of the projection of the beam 4308. Therefore, decision step 4106 is true. The intersection points for segment FS1 as determined in step 4126 are new points DP1 and DP2. In step 4136, points DP1 and DP2 are assigned as new vertices and define a new segment DS1. As dictated by step 4140, this process is repeated for the other segment of the facet boundary 4304 intersecting the beam projection boundary 4308. This is segment FS2. By a similar process as described for segment FS1, a new segment DS3 is defined having vertices DP4 and DP3. Because there are no more segments of the facet boundary 4304 which intersect the beam projection boundary 4308, the process proceeds to 4150 or it is repeated for the segments of the projection boundary 4308 which intersect with the facet boundary 4304. Segment PS1 does not intersect facet boundary 4304, therefore segment PS1 is not considered in this process. Segment PS2 intersects facet boundary 4304 and both of its vertices PP2, PP3 lie outside facet boundary 4304. Therefore, step 4106 is satisfied and a new segment DS2 is defined as having vertices DP2 and DP3. Segment PS3 has no intersection with facet boundary 4304 and is therefore not considered in this process. Segment PS4 intersects facet boundary 4304 and both of its vertices PP1, PP4 lie outside facet boundary 4304. Therefore, by a similar process, a new segment DS4 is defined having vertices DP4 and DP1.

FIG. 44 illustrates a scenario where two of the segments of facet boundary 4304 have one vertex outside of the projection boundary 4308 and the other vertex inside the projection boundary 4308. A third vertex of facet 4304 has both vertices FP3, FP1 lying within beam projection boundary 4308. Considering first segment FS1, segment FS1 has a first vertex FP1 lying inside the beam projection boundary 4308 and a second vertex FP2 lying outside beam projection boundary 4308. Thus, step 4102 is satisfied. The intersection point for segment FS1 is determined in step 4122 as new point DP2. New point DP2 is assigned as the new vertex for newly defined segment DS1 in step 4132.

Segment FS2 has a first vertex FP2 outside beam projection boundary 4308, and a second vertex FP3 lying inside beam projection boundary 4308. Thus, step 4104 is satisfied. Therefore, in a step 4124, DP3 is determined as the intersection point for segment FS2. Vertex DP3 is assigned as the new vertex 1 for segment DS3 in step 4134. Thus, as a result of the first two passes through the process described with reference to FIG. 41, new segments FS1 and DS3 are defined. New segment DS2 is defined utilizing the same process as described above for defining segment DS2 with reference to FIG. 43.

Note that segment FS3 has two vertices FP3, FP1 lying inside the beam projection boundary 4308. Therefore, there is no intersection of segment FS3 with the beam projection boundary 4308. Because both vertices FP3, FP1 of segment FS3 are inside beam projection boundary 4308, a new segment need not be defined. In one embodiment, vertices FP3, FP1 can be relabeled as vertices DP2, DP1. The coordinates of these vertices regardless of the labeling remains the same.

Figure 45:
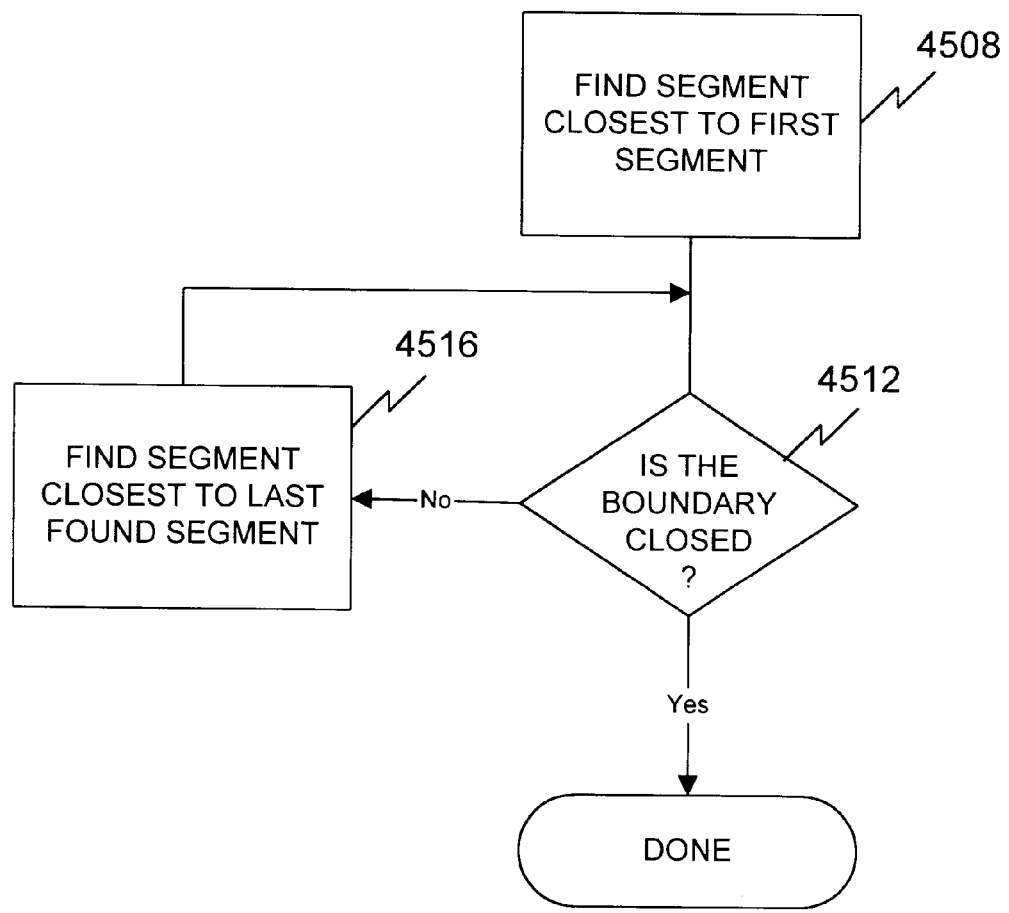
FIG. 45 is an operational flow diagram illustrating an example process for ordering the segments of the overlap boundary according to one embodiment of the invention.

As a result of the process described above, new segments are defined which describe the boundary of the overlap area between the facet boundary and the beam projection boundary. According to one embodiment, the next step in the process is to determine the "order" of these segments such that their definitions can be stored in a linked list. As stated above, the linked list is a useful embodiment for storing and retrieving data. FIG. 45 is an operational flow diagram illustrating a process for ordering the segments of the overlap boundary according to one embodiment of the invention. In a step 4504, the redefined segments a first redefined segment is retrieved. In a step 4508, the remaining redefined segments are examined to determine which segment is closest to the segment retrieved in step 4504. In a step 4512, the boundary is not yet closed, the process continues at step 4516 where the closest segment to the previously found closest segment is determined. This loop continues until the boundary of the overlap is closed.

As described above in reference to FIG. 30 in a step 3020, the final step of determining the overlap boundary of a beam projection in a receiving facet is to determine the overlap segments. In one embodiment, the overlap boundary is defined by a linked list of vertices which describe, in order, the segments which make up the overlap boundary.

As described above with reference to FIGS. 41 and 42, the vertices of the overlap segments are determined. Also discussed above, is the preferred embodiment of using a linked list data structure. In keeping with this embodiment, the overlap boundary can be defined in terms of a linked list of vertices which define, in order, the segments of the overlap boundary. That is, the linked lists of vertices start with a first vertex of the overlap boundary, and links, in order (either clockwise, or counterclockwise) each subsequent vertex around the perimeter of the boundary until the last vertex is linked with the first vertex. Determining the correct order of these vertices in such a linked list is now described according to one embodiment of the invention with reference to FIGS. 46 and 47.

In a step 4604, a first segment of the overlap boundary is chosen. More specifically, in the preferred embodiment, the vertices of the first segment are retrieved and an order for these vertices is chosen such that one vertex is defined as the first vertex for that segment and the other vertex is defined as the second vertex for that segment. The segment retrieved in step 4604 is referred to as the "current" segment.

In one embodiment of the invention, step 4604 is actually performed by first searching the segments of one boundary (either the B projection boundary or the facet boundary) to determine whether there are any segments in that boundary for which there is an overlap. Note that in the case of the scenario illustrated in FIG. 28(*b*), for example, an overlap boundary exists, however, one of those two boundaries has no segments which contribute to that overlap, while all the segments in the opposite boundary have an overlap. Specifically, in the scenario illustrated in FIG. 28(*b*), the beam projection boundary 2808 contains no segments which have an overlap. Therefore, the facet boundary 2804 is searched to find a segment having an overlap (i.e., a segment of the overlap boundary). This embodiment is especially useful where the data structure is implemented as a linked list, and the list of segments for the beam projection boundary and the list of segments for the facet projection boundary each contain all of the segments in that boundary whether or not one of the segments is defined as an overlap segment. Note that where one of the segments in the list is an overlap segment, its vertices are determined in one embodiment, as described above with reference to FIGS. 41 and 42.

In a step 4608, a next segment of the overlap boundary is retrieved. The retrieved segment may or may not be a segment adjoining the segment retrieved in step 4604. Thus, the process described below makes this determination.

In a step 4612, the invention assumes that the segment retrieved in step 4608 (referred to as the "first" segment) is the closest segment of the overlap boundary to the current segment.

This assumption is made without knowing whether this first segment is actually the segment which is closest to the current segment. In other words, in a step 4612, the invention assumes that the first segment retrieved is attached to (shares a common vertex with) the current segment. In one embodiment, the invention additionally assumes an orientation of this first segment. More specifically, the invention assumes that a particular one of the vertices of the first segment is coincident with one of the vertices (referred to as a designated vertex) of the current segment. Note that coincidence may not be exact due to rounding of mathematical results.

In this embodiment, the distance between these two assumed vertices is defined as the shortest distance. For example, in one embodiment, the invention assumes that the first vertex of the first segment is the closest vertex to the second vertex of the current segment. Thus, the segment is assumed to be adjacent to the current segment and is assumed to have a particular orientation (that is, the segment points away from the current segment in the direction of its second vertex).

In one embodiment, before continuing with further processing, this basic assumption is tested by determining whether the other vertex of the first segment is in fact closer to the designated vertex of the current segment. If this is the case, the orientation of the segment as originally assumed, is incorrect, and is therefore redefined.

In a step 4616, another segment of the overlap boundary is retrieved. This segment is referred to as the "next" segment, for ease of discussion. In a step 4620, the distance from this next segment to the current segment is computed. In a step 4704, it is determined whether this next segment is closer to the current segment than was the previous segment (i.e., than was the first segment retrieved in step 4608). If this next segment is closer than the previous segment, in a step 4708, this next segment is redefined as the current closest segment.

In a preferred embodiment, in step 4708, the correct orientation of the next segment is also determined such that the vertices of that segment can be identified in proper order for the linked list.

In a step 4712, the process determines whether there are any segments which have not been evaluated and which belong to the overlap boundary. If there are additional segments, the process continues as step 4616, where the next segment of the overlap boundary is retrieved. This next segment's distance to the current segment is computed, and it is determined in step 4704 whether this segment is closer than the segment currently defined as the closest segment.

If so, in step 4708, this segment is redefined as the closest segment, and the process repeats for each remaining segment of the overlap boundary to determine which of the set of segments in the overlap boundary is closest to the current segment. Once all of the other segments have been evaluated against the current segment (the segment of the overlap boundary retrieved in step 4604), and each of these have been tested as described above to determine which is closest, the operation continues at step 4716 where the linked list is updated to reflect the vertices of the closest segment. More particularly, in one embodiment, the second vertex of the closest segment is added to the linked list which already includes the first and second vertices of the current segment.

In a step 4720, it is determined whether the overlap boundary is closed. That is, it is determined whether each segment in the overlap boundary other than the first segment retrieved in step 4604 has been assigned as a closest segment to another segment.

If it is not, the process continues by looking for the segment which is closest to the segment defined as the closest segment to the current segment in the previous iteration. In other words, the closest segment found in the previous iteration is now the "current" segment, and its closest segment is found. Now, the process resumes at step 4608, where a next segment of the overlap boundary is retrieved, assumed to be the closest segment to the new current segment, and compared against other unassigned segments of the overlap boundary to determine which is in fact the closest. This entire process repeats until every segment, other than the very first segment, is assigned as a closest segment to a current segment.

Figure 46:
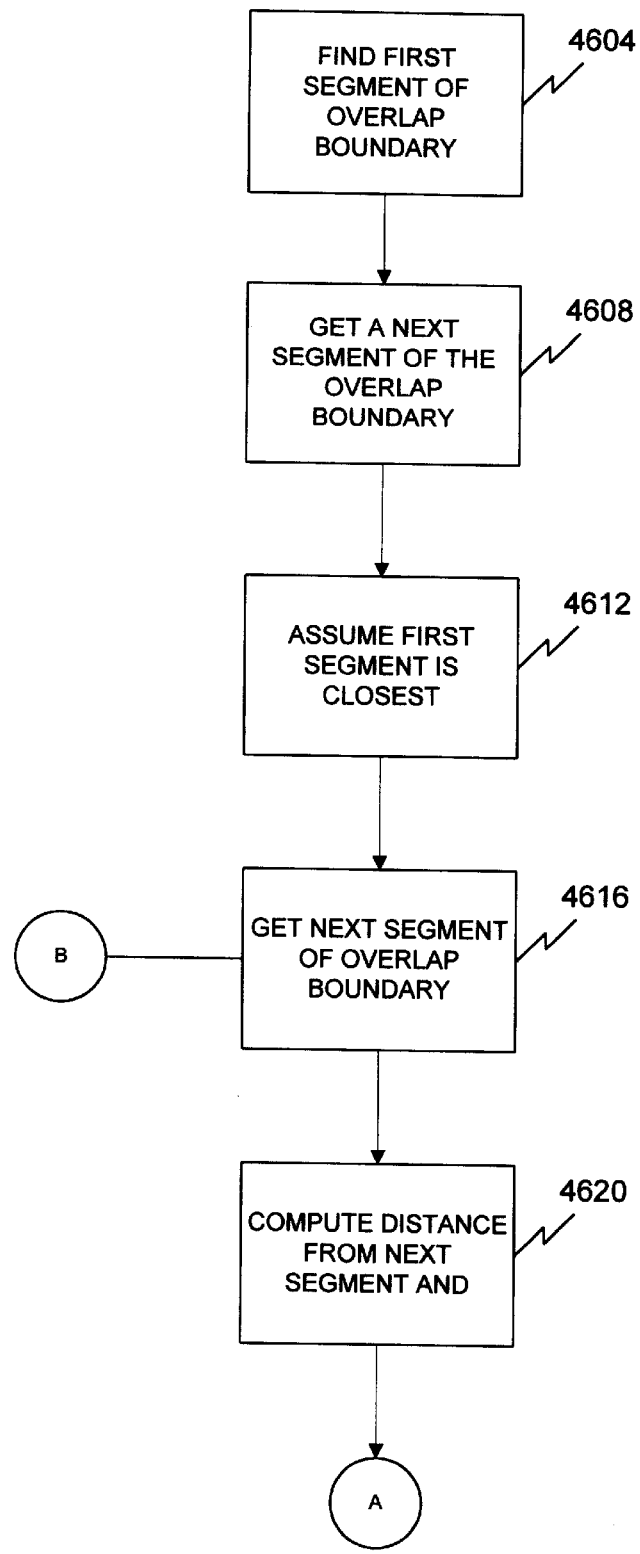
FIG. 46 is an operational flow diagram illustrating an example process for ordering the vertices in a linked list according to one embodiment of the invention.
Figure 47:
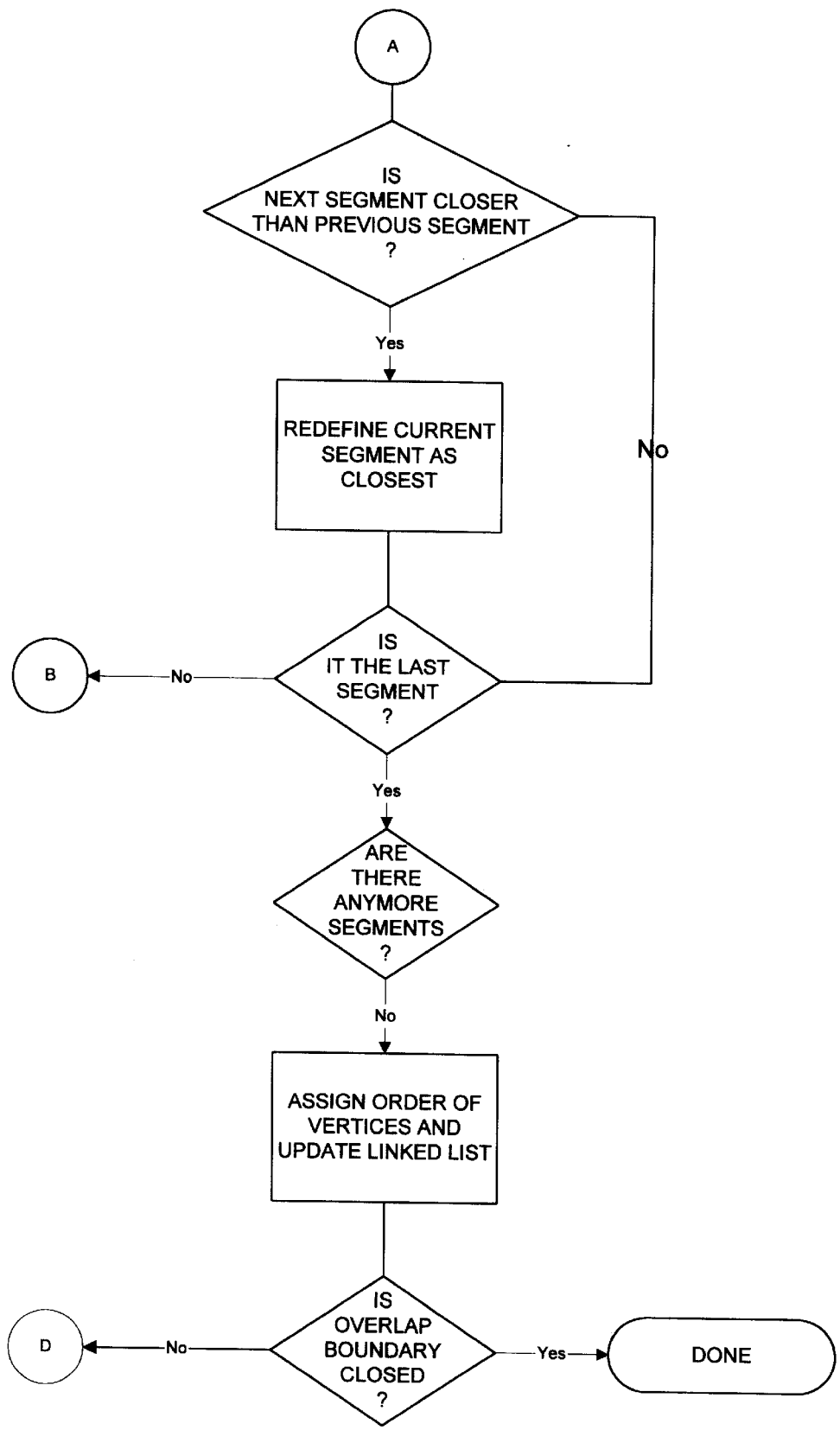
FIG. 47 is an operational flow diagram illustrating an example process for ordering the vertices in a linked list according to one embodiment of the invention.

The details and the function of this process will become more clear to the reader if considered in light of an example scenario. Therefore, the process described in reference to FIGS. 46 and 47 is now generally described in terms of a simple example. The example utilized is the overlap boundary illustrated in FIG. 43. As described above, this overlap boundary is defined by overlap segments DS1, DS2, DS3, and DS4. These segments have vertices DP1, DP2; DP2, DP3; DP3, DP4; and DP4, DP1; respectively.

In step 4604, the first segment of the overlap boundary is retrieved. For the purposes of describing this example, this first segment is assumed to be segment DS1. In the embodiment in which a linked list data structure is utilized, the vertices of segment DS1 are assigned as the first and second vertices of the linked list. For example, vertex DP1 is assigned as the first vertex in the linked list and vertex DP2 is assigned as the second vertex in the linked list. For ease of discussion, the segment DS1 is referred to as the "current segment."

In a step 4608, a next segment of the overlap boundary is retrieved. For the purpose of this example, assume that this next segment retrieved is segment DS3.

In a step 4612, the process assumes that segment DS3 is the closest segment in the overlap boundary to segment DS1. That is, the segment DS3 is assigned as the "closest segment" without yet comparing its distance against the other segments to determine whether this assignment is correct and can be maintained.

As described above, in one embodiment, this assignment is actually made by assigning the distance from one of the vertices of segment DS3 to one of the vertices of segment DS1 as the shortest distance. For example, the invention in one embodiment will assign the distance between the first vertex of segment DS3 and the second vertex of segment DS1 as the shortest distance. In the example illustrated in FIG. 43, and assuming that the first vertex of segment DS3 is DP3, this assignment results in the distance from vertex DP3 to vertex DP2 being assigned as the assumed shortest distance.

In the preferred embodiment, this initial assumption is verified with respect to segment DS3 by computing the distance between vertex DP4 and vertex DP2. If vertex DP4 is actually closer to vertex DP2 than was vertex DP3, the distance between vertex DP4 and vertex DP2 is designated as the new shortest distance.

Also, which vertex of DS3 is actually closest to vertex DP1 defines the orientation of segment, DS3. For example, in the example illustrated in FIG. 43, the vertex DP3 is actually closer to vertex DP2 than is vertex DP4. Therefore, in one embodiment, the orientation of vertex DS3 is defined such that vertex DP3 is the first vertex, and vertex DP4 is the second vertex of segment DS3.

As this example clearly shows by referring to the illustration of FIG. 43, segment DS3 is actually not the closest segment to segment DS1. However, this example illustrates how the process described according to this embodiment makes an assumption regarding the closest segment based on the available data, and then through subsequent iterations attempts to prove the assumption wrong and updates the assignment of the closest segment—or, alternatively does not update the assignment if the initial assumption is not proven wrong.

In an alternative embodiment, other techniques can be implemented for determining the correct order of the linked list of segments. In one embodiment, this can be accomplished by comparing the vertices of the segments to see which segments share a common vertex with which other segments. An order can then be established in this manner.

In a step 4616, a next segment of the overlap boundary is retrieved. For the purpose of this example, assume that the next segment retrieved is segment DS2.

In step 4620, the distance from this next segment DS2 to the original segment FS1 is computed. As described above, in one embodiment, this distance is actually computed based on the distance of the vertices of segment DS2 to one vertex of segment DS1. Particularly, in keeping with the embodiment described above, the distance between vertex DP3 of segment DS2 and vertex DP2 of segment DS1 is computed. Additionally, the distance between vertex DP2 of segment DS2 and vertex DP2 of segment DS1 is computed. As clearly illustrated by the diagram of FIG. 43, vertex DP2 of segment DS2 and vertex DP2 of segment DS1 are one and the same (or at least extremely close, but slightly off due to rounding errors). Therefore, their distance is effectively zero. Because this distance is the shortest distance yet determined, segment DS2 is defined as the closest segment and vertex DP2 of segment DS2 is defined as the first vertex of that segment.

This process repeats for segment DS4, as illustrated by decision step 4712. Once segment DS4 is processed in a similar manner, it is determined that the distance between vertex DP2 of segment DS2 and vertex DP2 of segment DS1 is in fact the shortest distance. Therefore, the definition of the closest segment remains segment DS2, and the linked list of vertices is updated in step 4716 to now include vertex DP3. As a result, there are now three vertices in the linked list: DP1, DP2, and DP3.

In an alternative embodiment, the process is concluded once a vertex having a distance of zero is found. Note that this embodiment may not be ideal where rounding errors results in an erroneous determination of the closest vertex.

In step 4720, it is determined that the overlap boundary is not closed. That is, only segments DS1 and DS2 have been included in the linked list. Segments DS3 and DS4 remain to be evaluated to determine their correct orientation and order for inclusion of their vertices in the linked list.

Because, in the example illustrated in FIG. 43, at this juncture the overlap boundary is not closed in a step 4608, a next segment of the overlap boundary is retrieved. The segments which have not been assigned according to the current example are segments DS3 and DS4. For the purpose of this example, assume that segment DS3 is the next segment retrieved in step 4608.

In step 4612, the process assumes that this segment DS3 is actually the closest segment to segment DS2. Again, in the preferred embodiment, this assumption is made by assuming that one of the vertices, DP4, DP3, is closest to vertex 2 (DP3) of segment DS2. This assumption is checked by comparing the differences between the distances between the two vertices of segment DS3 and the second vertex of segment DS2, and updated if necessary.

In a step 4616, the next segment of the overlap boundary, which is segment DS4, is retrieved.

In step 4620, the distance of this segment DS4 from segment DS2 is computed. Again, in the preferred embodiment, this is accomplished by computing the distances between vertices DP4 and DP3 and vertices DP1 and DP3. If this segment DS4 is closer than segment DS3, it is redefined as the current closest segment, as illustrated by steps 4704 and 4708. In actuality, however, as seen by the illustration in FIG. 43, segment DS4 is in fact not closer to segment DS2 than segment DS3. Therefore, step D.9.708 is bypassed in this operation, and the process continues at step 4712 to determine whether this was the last segment to be evaluated for comparison against segment DS2. Because it was, in step 4716, the linked list of vertices is updated to reflect that vertex DP4 is the fourth vertex in the linked list.

In step 4720, it is determined that the overlap boundary is not closed, as segment DS4 has not been evaluated. Thus, the process continues at step 4608, where segment DS4 is the next segment of the overlap boundary retrieved. In step 4612, it is assumed that this segment DS4 is the closest segment to segment DS3. In the preferred embodiment, the orientation of segment DS4 is determined by determining which vertex of segment DS4 is actually closest to the second vertex of segment DS3. Because there are no additional segments to be evaluated, the process resumes at step 4716, where the linked list of vertices is updated to reflect that vertex DP4 points back to the beginning of the list, vertex DP1.

22.0 Evaluation And Computer Grade 22.1 Evaluate Output Light Attributes

In a preferred embodiment of the present invention, the data collected by the cameras is processed to obtain a cut grade for the gemstone. As described above, a number of measurements are collected for each light beam refracted to the cameras. These measurements are actually measurements of a set of one or more attributes of the light exiting the stone.

These attributes can include, without limitation, average angle of spectral deviance, white flux density (brilliance), spectral luminance (dispersion or fire), total refraction count (scintillation), spectral flux density, white optical power, spectral power, white intensity, dispersion intensity, total refraction area, and total refraction area to surface area density.

In one embodiment, any one or more of these attributes is measured for the light exiting the stone. The results of these measurements can be tabulated to provide an indication of the light output from the stone.

Additionally, any or all of the above values may be output by horizontal and vertical camera angles and evaluated with or without regard to facet type and with or without regard to deviance reductions, weighting or averaging.

The measurements can be collected and recorded for each facet, for a region of the stone, or for the entire stone. Each camera in the camera model is capable of determining these measurements for the light beams which it receives.

22.2 Grading Camera Data

The cut grade may be based on an analysis, computation, or compilation of any or all of these measurements, for the stone and can be defined to include other factors as well.

In a preferred embodiment, each collected attribute measurement is compared to the theoretical maximum measurement for the particular type of gemstone cut (for example, round, brilliant, marquise, etc.). Each attribute measurement can therefore be expressed as a percentage of the theoretical maximum. Each of these percentages can be reported as a component of the grade, expressed as a percentage.

In a preferred embodiment, the composite gemstone cut grade is determined by averaging the percentages for three attributes: brilliance, dispersion and scintillation. The total gemstone grade is then expressed as a percentage. These three attributes are chosen in the preferred embodiment because it is believed they are the most important attributes of the light output. Other attributes can be selected in alternative embodiments.

In fact, in alternative embodiments, any one or more of these or other attributes may be combined according to a chosen formula to determine a grade for the stone. For example, a grade may be expressed as an average a weighted average, a sum, or some other expression of the chosen set of attributes.

Figure 48:
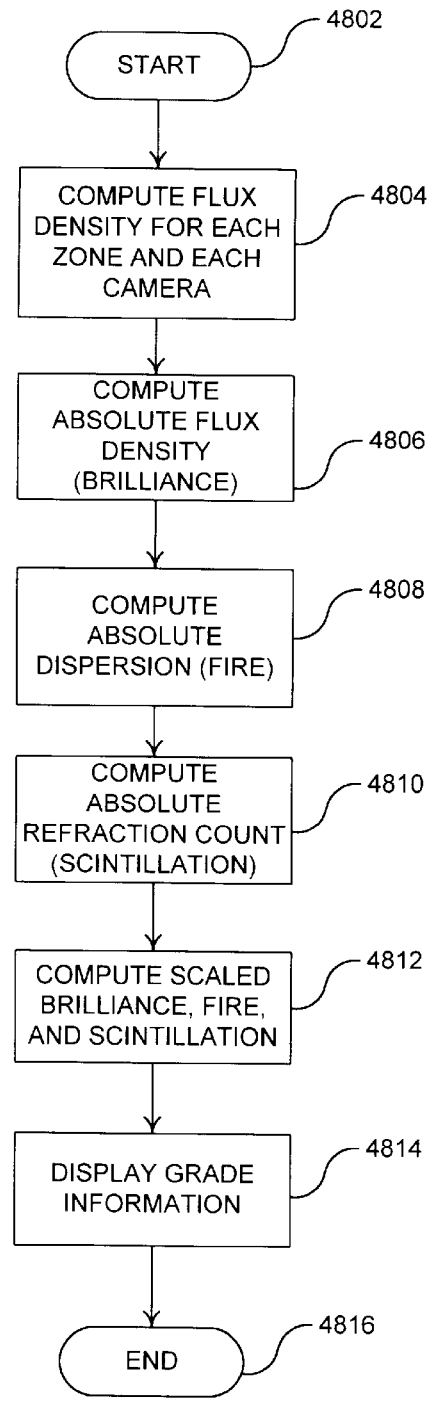
FIG. 48 is a flowchart depicting an example process for grading camera data, according to the preferred embodiment of the invention.

FIG. 48 is a flowchart depicting an example process for grading camera data, according to the preferred embodiment of the invention. This process illustrates one manner in which step 220 of FIG. 2 can be performed. In a preferred embodiment, the three measurements of the light refracted from the gemstone model that are used to compute the gemstone grade are flux density (also referred to as "brilliance"), spectral luminance (also known as "fire"), and refraction count (also known as "scintillation").

As described above, each zone in each camera maintains several measures of received flux: one for the white beam component, and one for each dispersion component. In a step 4804, the total flux density for each zone, and for each camera, is computed.

As described above, in a preferred embodiment, measurements are collected for each component of the grade, and then these absolute measurements are compared to "ideal" measurements to determine a scaled grade. Therefore, in a step 4806, the flux density measurements for the zones and cameras are combined to create a composite absolute flux density measurement for the entire gemstone. Similarly, composite absolute measures for dispersion and refraction count are computed in steps 4808 and 4810, respectively. Finally, these absolute measurements for brilliance, fire and scintillation are compared to ideal values to create scaled values, as shown in a step 4812.

In a preferred embodiment, the scaled grade is obtained by dividing the absolute measurement by the ideal measurement to obtain a percentage. Finally, as shown in a step 4814, the scaled measurements are combined to create a composite scaled cut grade for the gemstone.

22.3 Compute Gemstone Brilliance

Figure 49:
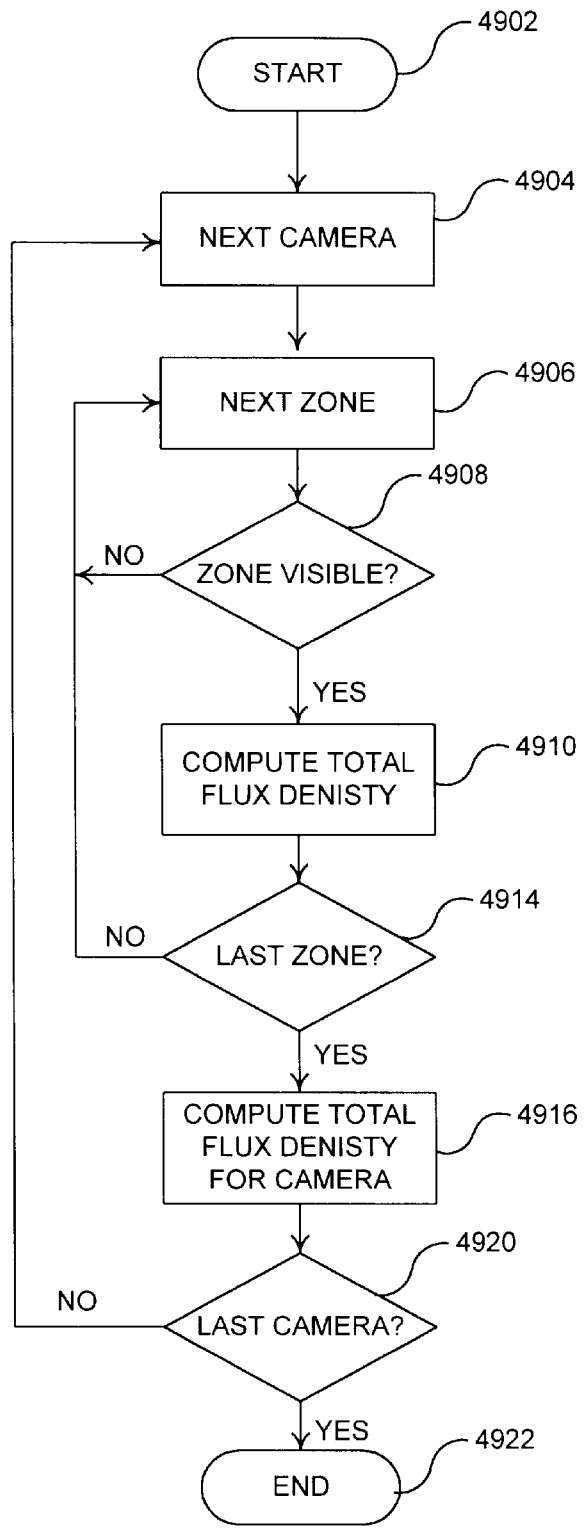
FIG. 49 is a flowchart depicting an example process for computing the flux density for each zone and each camera according to one embodiment of the invention.

FIG. 49 is a flowchart depicting an example process for computing the flux density for each zone and each camera. This illustration is an example process for implementing step 4804 in FIG. 48. First, a camera is selected for processing, as shown in a step 4904. Then, a zone within the selected camera is selected for processing, as shown in a step 4906.

The selected zone is checked to determine whether it is visible to the selected camera. As described above, this determination was made when the camera zones were constructed, and was stored as a part of the zone data structure. The zone data structure is described in detail below. If the zone is not visible, another zone within the camera is selected for processing.

If the zone is visible, then the total flux density for the zone is computed, as shown in a step 4910. As described above, each zone maintains several to, measures of received flux: one for the white component, and one for each dispersion component. In a preferred embodiment, the total flux density for the zone is computed by dividing the total flux for the white beam component by the area of the projection of the facet corresponding to the zone upon the plane of the camera. In an alternative embodiment, the total flux density is computed by dividing the sum of the fluxes for each dispersion component by the area of the projection. Other methods of computing total flux density based on the stored measures of flux are within the spirit and scope of the present invention, as would be apparent to one skilled in the relevant art.

Each zone in the camera is processed similarly, as shown in a step 4904. When the last zone in the camera has been processed, the total flux density for the camera is computed, as shown in a step 4916. The total flux density for the camera is derived from the flux densities of the camera's zones, as would be apparent to one skilled in the relevant art. Each camera is processed similarly, as shown in a step 4920.

In a preferred embodiment, when the flux densities for each zone and camera have been computed, the absolute composite flux density for the gemstone is computed. Note, that depending on the goals of the grading process, the individual flux densities may be retained for evaluation.

Figure 50:
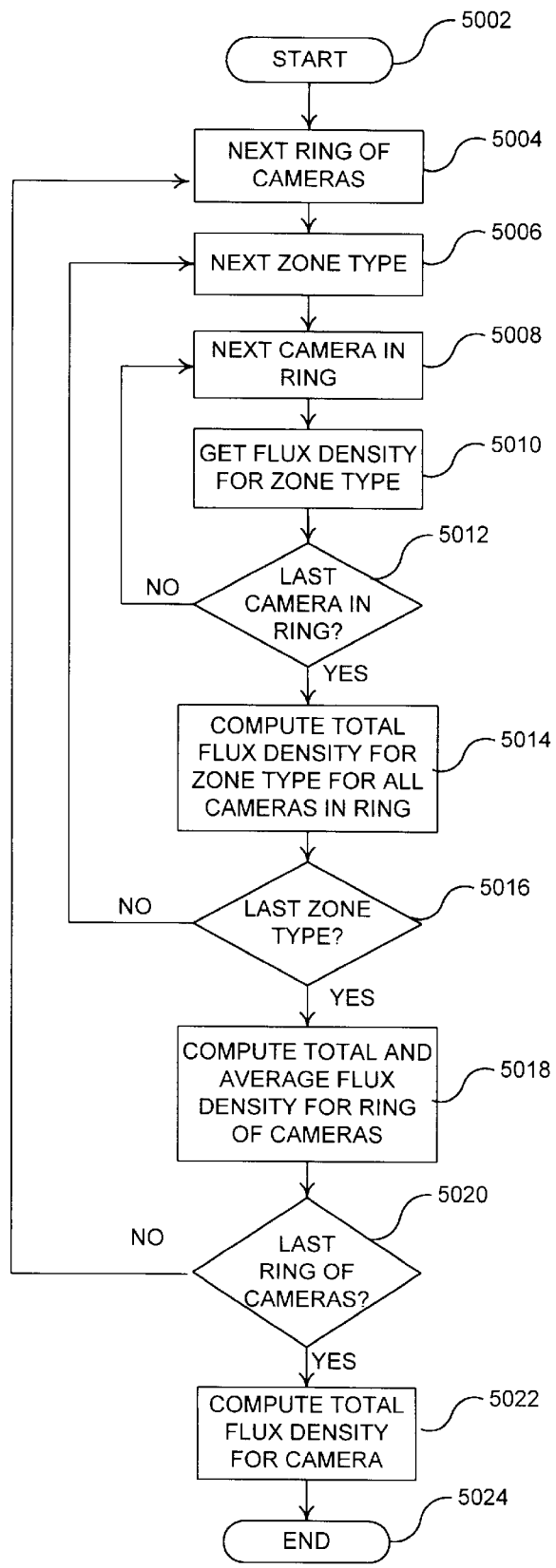
FIG. 50 is a flowchart depicting an example process for computing the absolute flux density for the gemstone model, according to a preferred embodiment of the invention.

FIG. 50 is a flowchart depicting an example process for computing the absolute flux density for the gemstone model, according to a preferred embodiment of the invention. This illustrates one process for implementing step 4806 of FIG. 48. In the preferred embodiment, the cameras are examined one group at a time. In a preferred embodiment, the groups of cameras are selected based on elevation angles. Thus in a step 5004, a "ring" of cameras is selected for processing. This ring of cameras is formed by selecting all cameras at a given elevation angle. In a preferred embodiment, the ring of cameras having the lowest elevation angles are processed first. Then the ring of cameras at the next lowest elevation angle is processed, and so on.

In a preferred embodiment, grade measurements are collected by zone type (for example, table, break, main, and star). In a step 5006, a zone type is selected for processing. The cameras in the selected ring are then processed, one camera at a time. In a step 5008, a camera in the ring is selected for processing.

In a step 5010, all of the zones in the camera are examined to select all zones in the camera that are of the selected zone type. The total flux density for all of the selected camera zones is then computed, as shown in a step 5010. Each camera in the selected ring is processed in a similar manner, as shown in a step 5012.

When all of the cameras in the ring have been processed, the total flux density for the selected zone type is computed for all of the cameras in the ring, as shown in a step 5014. Each zone type is processed similarly, as shown in a step 5016.

When all of the zone types have been processed through the camera ring, the total and average flux density is computed for the entire ring of cameras, as shown in a step 5018. The result is a measure of gemstone brilliance for a given elevation angle.

Each ring of cameras is processed similarly, as shown in a step 5020. When all of the cameras have been processed, the total flux density for the gemstone is computed, as shown in a step 5022. The result is a composite measure of the brilliance of the entire gemstone.

In a preferred embodiment, supplementary brilliance information is computed. This information can include flux density totals for each zone type and standard deviations of flux densities over a vertical range.

22.4 Compute Gemstone Dispersion

Figure 51:
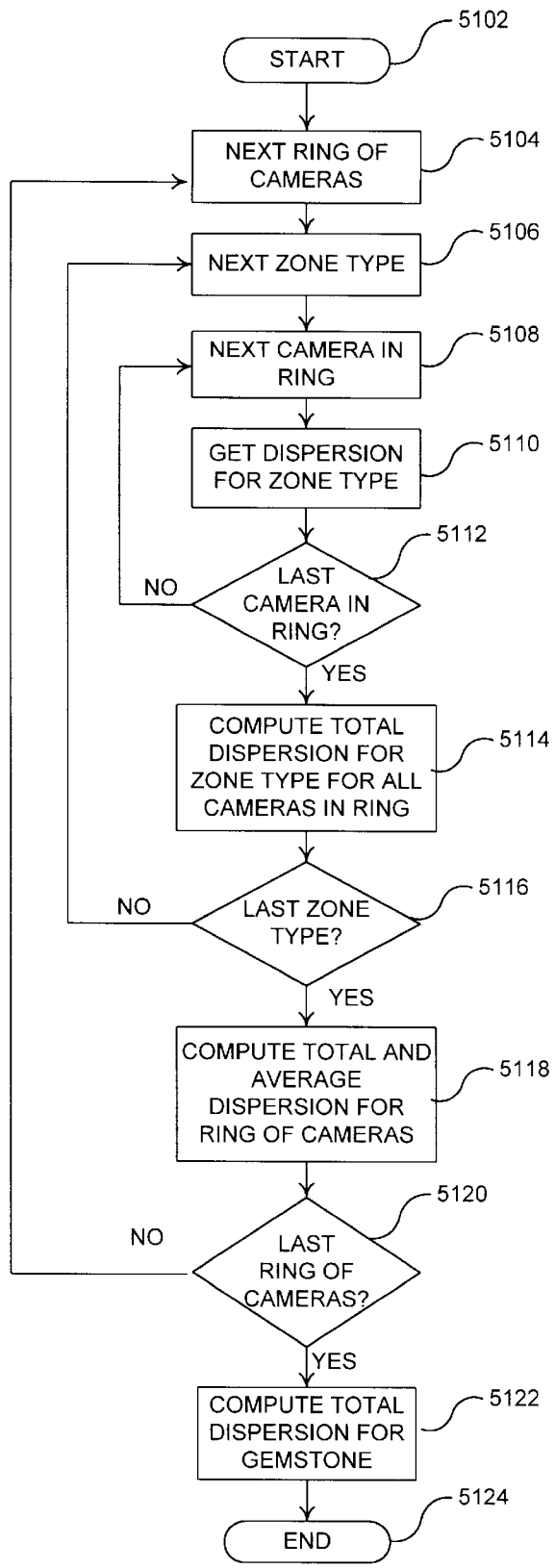
FIG. 51 is a flowchart depicting an example process for computing the absolute dispersion for the gemstone model, according to a preferred embodiment of the invention.

FIG. 51 is a flowchart depicting an example process for computing the absolute dispersion for the gemstone model, according to a preferred embodiment of the invention. This illustrates one process for implementing step 4808 of FIG. 48. In the preferred embodiment, the cameras are examined one group at a time. In a preferred embodiment, the groups of cameras are selected based on elevation angles. Thus in a step 5104, a "ring" of cameras is selected for processing. This ring of cameras is formed by selecting all cameras at a given elevation angle. In a preferred embodiment, the ring of cameras having the lowest elevation angles are processed first. Then the ring of cameras at the next lowest elevation angle is processed, and so on.

In a preferred embodiment, grade measurements are collected by zone type (for example, table, break, main, and star). In a step 5106, a zone type is selected for processing. The cameras in the selected ring are then processed, one camera at a time. In a step 5108, a camera in the ring is selected for processing.

In a step 5110, all of the zones in the camera are examined to select all zones in the camera that are of the selected zone type. The total dispersion for all of the selected camera zones is then computed, as shown in a step 5110. Each camera in the selected ring is processed in a similar manner, as shown in a step 5112.

When all of the cameras in the ring have been processed, the total dispersion for the selected zone type is computed for all of the cameras in the ring, as shown in a step 5114. Each zone type is processed similarly, as shown in a step 5116.

When all of the zone types have been processed through the camera ring, the total and average dispersion is computed for the entire ring of cameras, as shown in a step 5118. The result is a measure of gemstone fire for a given elevation angle.

Each ring of cameras is processed similarly, as shown in a step 5120. When all of the cameras have been processed, the total dispersion for the gemstone is computed, as shown in a step 5122. The result is a composite measure of the fire of the entire gemstone. In a preferred embodiment, supplementary fire information is computed. This information can include dispersion totals for each zone type and standard deviations of dispersions.

22.5 Compute Gemstone Scintillation

Figure 52:
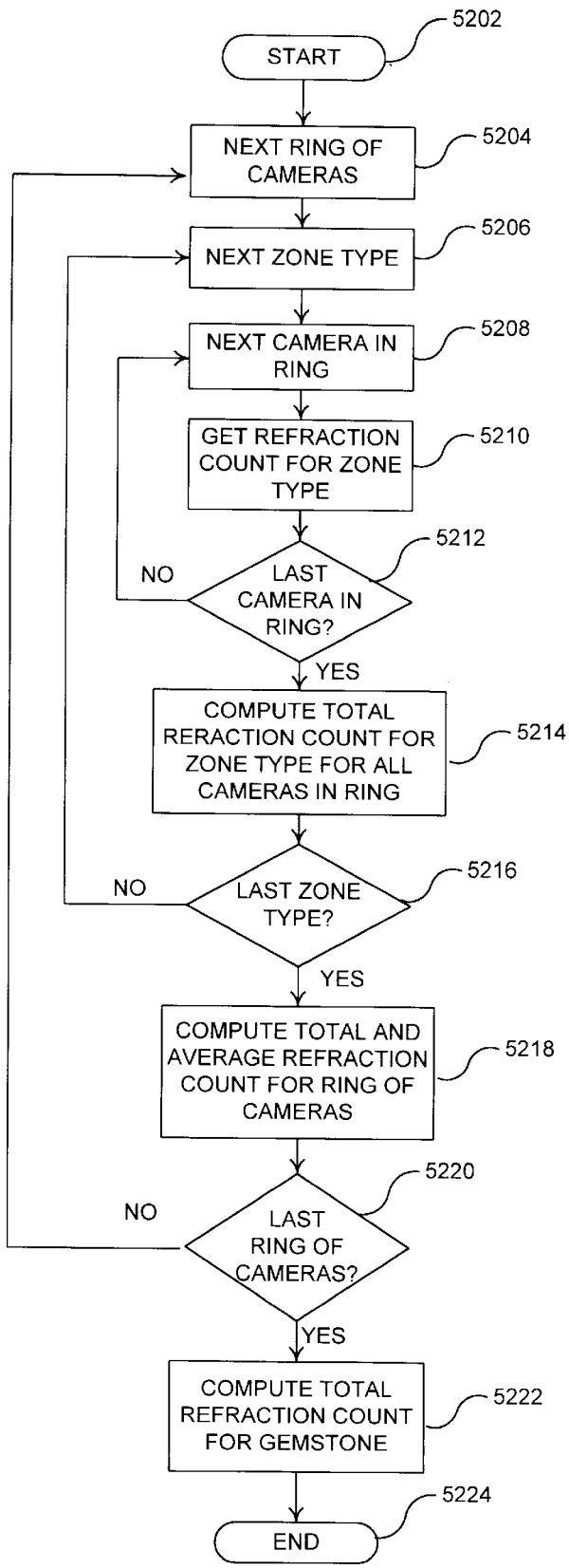
FIG. 52 is a flowchart depicting an example process for computing the absolute refraction count for the gemstone model, according to a preferred embodiment of the invention.

FIG. 52 is a flowchart depicting an example process for computing the absolute refraction count for the gemstone model, according to a preferred embodiment of the invention. This illustrates one process for implementing step 4810 of FIG. 48. In the preferred embodiment, the cameras are examined one group at a time. In a preferred embodiment, the groups of cameras are selected based on elevation angles. Thus in a step 5204, a "ring" of cameras is selected for processing. This ring of cameras is formed by selecting all cameras at a given elevation angle. In a preferred embodiment, the ring of cameras having the lowest elevation angles are processed first. Then the ring of cameras at the next lowest elevation angle is processed, and so on.

In a preferred embodiment, grade measurements are collected by zone type (for example, table, break, main, and star). In a step 5206, a zone type is selected for processing. The cameras in the selected ring are then processed, one camera at a time. In a step 5208, a camera in the ring is selected for processing.

In a step 5210, all of the zones in the camera are examined to select all zones in the camera that are of the selected zone type. The total refraction count for all of the selected camera zones is then computed, as shown in a step 5210. Each camera in the selected ring is processed in a similar manner, as shown in a step 5212.

When all of the cameras in the ring have been processed, the total refraction count for the selected zone type is computed for all of the cameras in the ring, as shown in a step 5214. Each zone type is processed similarly, as shown in a step 5216.

When all of the zone types have been processed through the camera ring, the total and average refraction count is computed for the entire ring of cameras, as shown in a step 5218. The result is a measure of gemstone scintillation for a given elevation angle.

Each ring of cameras is processed similarly, as shown in a step 5220. When all of the cameras have been processed, the total refraction count for the gemstone is computed, as shown in a step 5222. The result is a composite measure of the scintillation of the entire gemstone. In a preferred embodiment, supplementary scintillation information is computed. This information can include refraction count totals for each zone type and standard deviations of refraction counts.

23.0 Establishing Maximum Values for Light Attributes

As described above with reference to the grading of a gemstone, in one embodiment, the gemstone can be evaluated based on the attributes of the light exiting the stone. In one embodiment, the stone is graded by comparing measurements of one or more light attributes to a maximum value established for that attribute. Such a maximum can be, for example, a theoretical maximum, a derived maximum or some other maximum value based on actual data. In one embodiment, a maximum value for each of one or more attributes is computed by modeling each of the various possibilities of the cut of the gemstone and determining the highest value of each attribute for all of the possibilities modeled.

Figure 53:
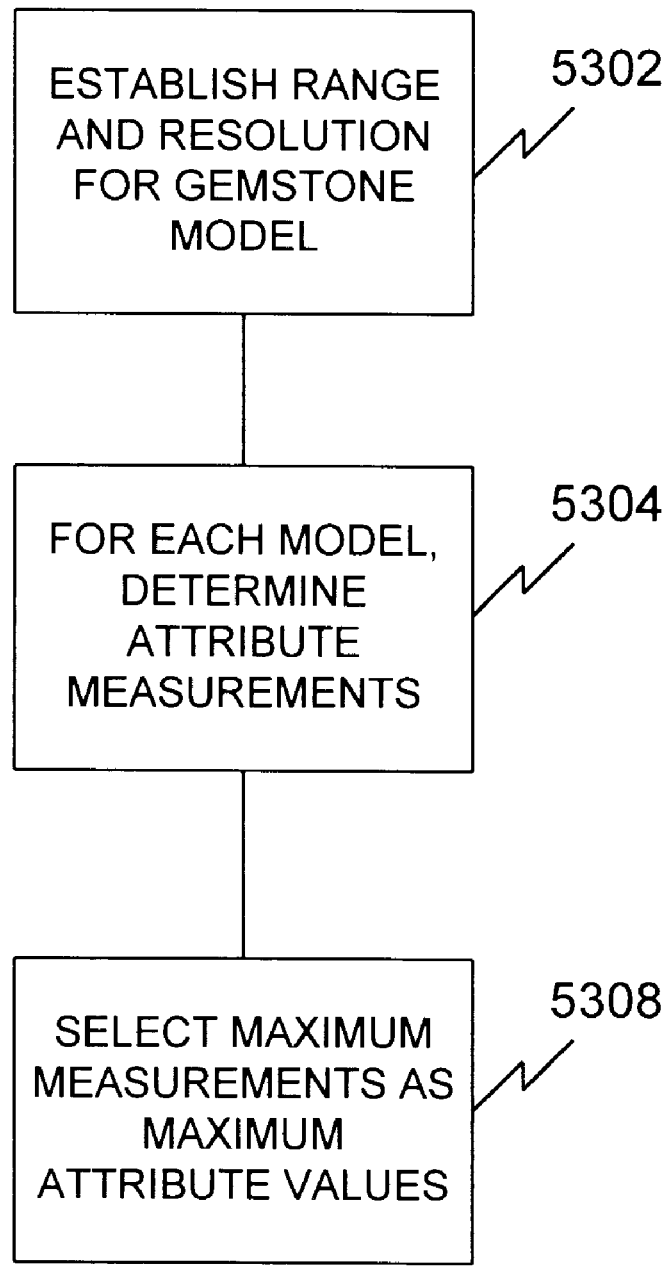
FIG. 53 is an operational flow diagram illustrating an example process for determining maximum attribute values by modeling various gemstone cuts according to one embodiment of the invention.

FIG. 53 is an operation flow diagram illustrating at a high level an example process for determining maximum attribute values by modeling various gemstone cuts. In a step 5302, a range and resolution for the gemstone models is established. For example, in one embodiment, a range of proportions for each the table, crown and pavilion measurements is established. Within this range, a resolution is defined which establishes the number of different cut proportions which will be examined within this range to determine the attribute measurements.

In a step 5304, for each gemstone model defined by the range and resolution, light is traced through the gemstone model and the exiting light is measured to determine the attribute values for each of the attributes in question. In a step 5308, the maximum measurement for each attribute from all of the modeled cuts is selected as the maximum value for that attribute.

Thus, as a result of this process, a series of gemstone cuts within a predefined range are modeled, and the light exiting those models is measured to determine the attribute measurements for each of the cuts. The maximum attribute measurements determined in this process are selected as the maximum values for the attribute.

Figure 54:
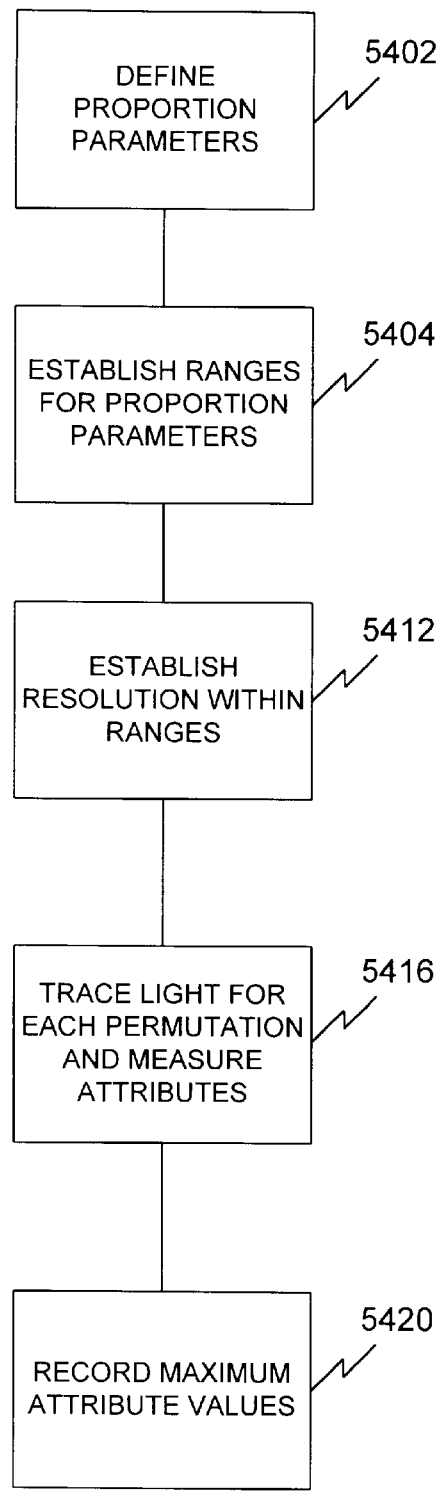
FIG. 54 is an operational flow diagram illustrating an example process for determining maximum attribute values by modeling various gemstone cuts according to one embodiment of the invention.

FIG. 54 is an operational flow diagram illustrating an example embodiment for implementing the process described above with reference to FIG. 53.

In a step 5402, the parameters of the stone for which the attributes are to be defined are established. For example, for a round gemstone, the proportion parameters of importance are the table percentage, the crown percentage, and the pavilion percentage. In other words, it is these proportions which are important in determining the quality of the cut. Additionally, parameters such as facet types, facet numbers, facet locations, and other cut-related information can be defined as a parameter which is varied to establish all of the possible permutations of cut for the stone.

In a step 5404, a range of these parameters is established. Preferably, there is a range established for each parameter. For example, the range of parameters for the table may be table proportions from 35% to 65%. It is within the established range of parameters that the various combinations of parameters defining the different cuts will be evaluated.

In a step 5412, a resolution within these ranges is established. This is the step size within the range.

In a step 5416, each possible combination of cut parameters is modeled, light is traced through the gemstone and the output measured to determine the attribute values. For each combination, if a measured attribute is a maximum value for that attribute, that value is recorded in a step 5420.

Figure 55:
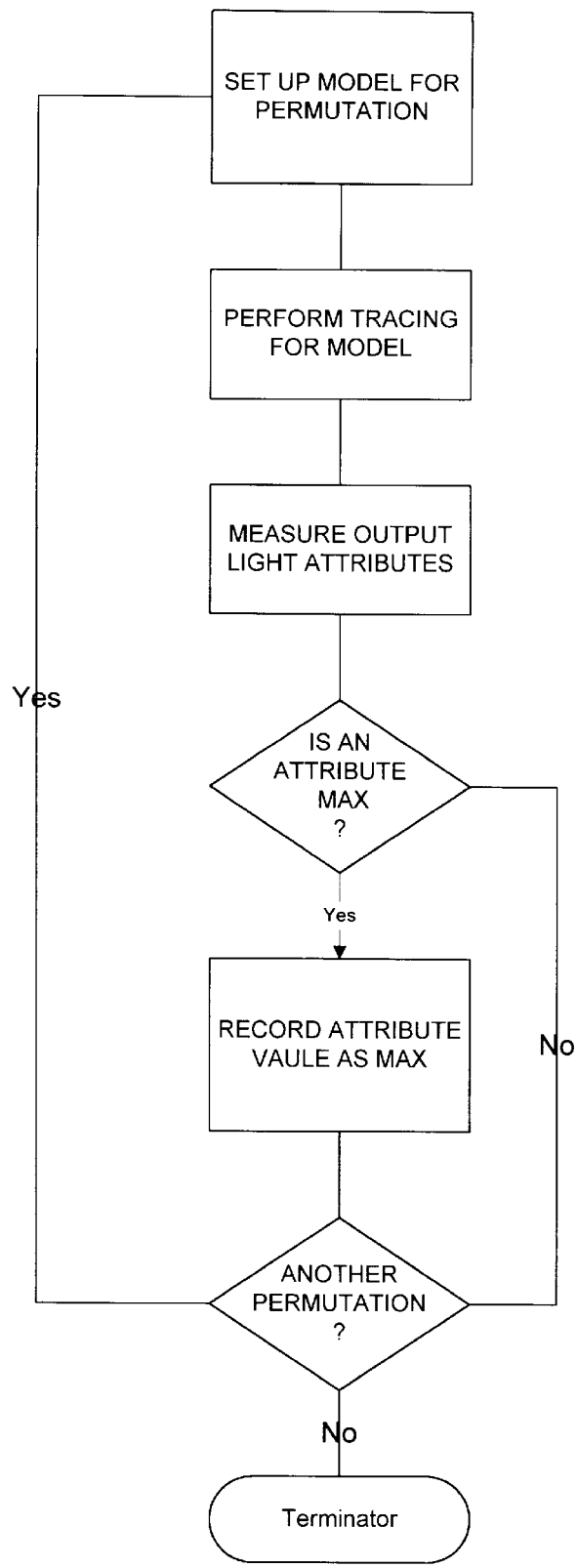
FIG. 55 is an operational flow diagram illustrating an example process for determining maximum attribute values by modeling various gemstone cuts according to one embodiment of the invention.

FIG. 55 is an operational flow diagram illustrating an example process for implementing the operation.

In a step 5504, a gemstone model is set up for the current permutation. That is, a unique combination of parameters is chosen and a model is created for those parameters. In a step 5508, the invention traces the light for this particular model. In a step 5512, the output light attributes are measured.

The value of each attribute measured is compared against a previous maximum measured value to determine whether the new measurement is greater than the previously-stored measurement. This is illustrated by decision step 216. If the attribute measured for the current combination is greater than the previously-stored maximum attribute value, this new attribute value is recorded as the maximum attribute value in a step 5520. If it is not a maximum, the recorded maximum is not changed, and processing continues at a step 5524. In a step 5524, it is determined whether all of the various combinations of parameters have been modeled and measured. If not, there is another combination to be considered, and the process resumes at step 5504 where the next model is set up. This process continues for each combination of proportion parameters until all of the combinations have been considered. Each time an attribute value is greater than a previously-stored maximum attribute value, this new attribute value is stored as the new maximum. Thus, once the process is completed, a maximum modeled attribute value is obtained.

24.0 Software/Hardware Implementation

Figure 56:
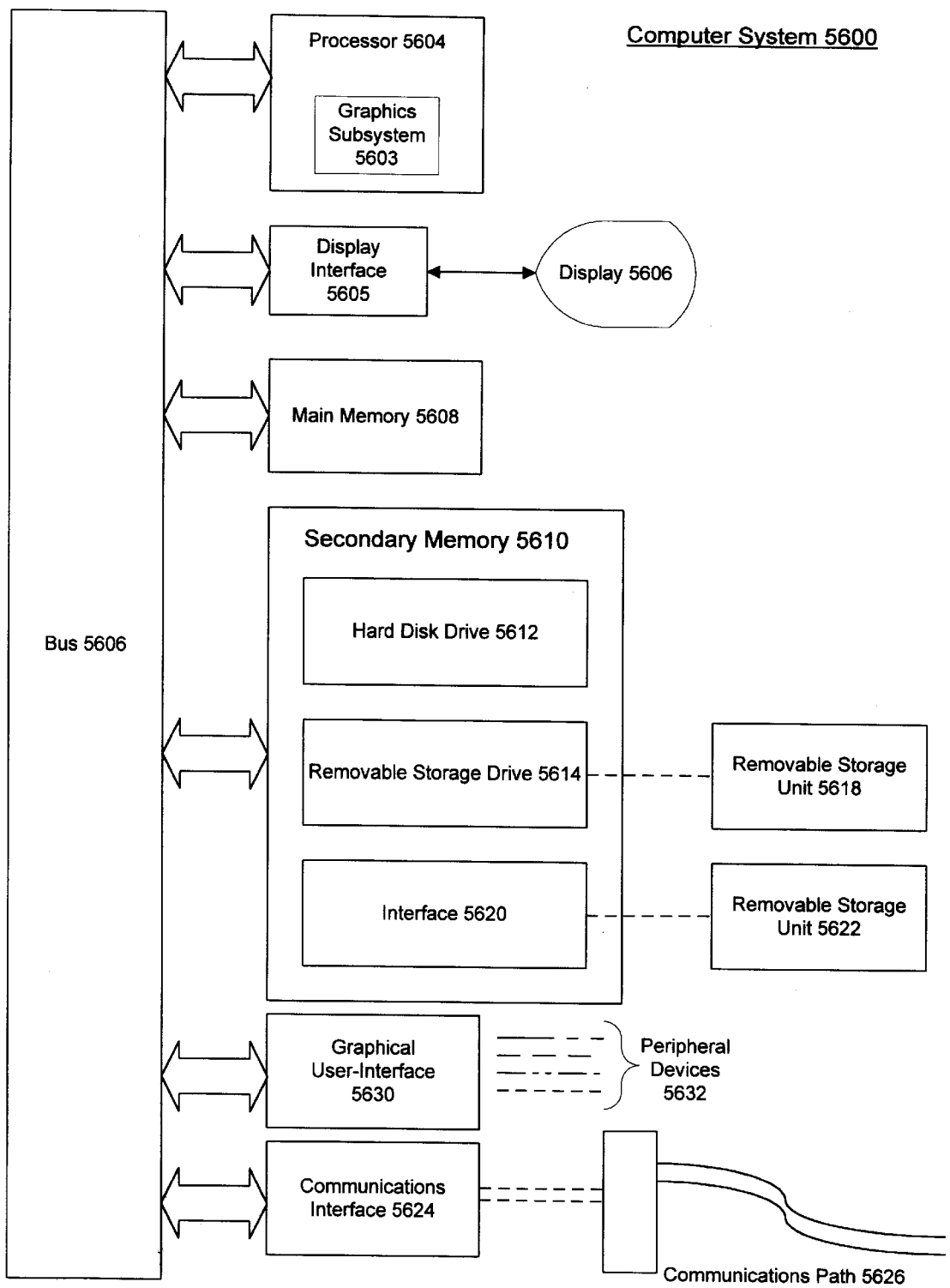
FIG. 56 is an operational flow diagram depicting an example computer system on which the invention can be implemented in one embodiment of the invention.

The present invention may be implemented using hardware, software or a combination thereof and may be implemented in a computer system or other processing system. In fact, in one embodiment, the invention is directed toward a computer system capable of carrying out the functionality described herein. An example computer system 5602 is shown in FIG. 56. The computer system 5602 includes one or more processors, such as processor 5604. The processor 5604 is connected to a communication bus 5606. Various software embodiments are described in terms of this example computer system. After reading this description, it will become apparent to a person skilled in the relevant art how to implement the invention using other computer systems and/or computer architectures.

Computer system 5602 also includes a main memory 5608, preferably random access memory (RAM, and can also include a secondary memory 5610. The secondary memory 5610 can include, for example, a hard disk drive 5612 and/or a removable storage drive 5614, representing a floppy disk drive, a magnetic tape drive, an optical disk drive, etc. The removable storage drive 5614 reads from and/or writes to a removable storage unit 5618 in a well known manner. Removable storage unit 5618, represents a floppy disk, magnetic tape, optical disk, etc. which is read by and written to by removable storage drive 5614. As will be appreciated, the removable storage unit 5618 includes a computer usable storage medium having stored therein computer software and/or data.

In alternative embodiments, secondary memory 5610 may include other similar means for allowing computer programs or other instructions to be loaded into computer system 5602. Such means can include, for example, a removable storage unit 5622 and an interface 5620. Examples of such can include a program cartridge and cartridge interface (such as that found in video game devices), a removable memory chip (such as an EPROM, or PROM) and associated socket, and other removable storage units 5622 and interfaces 5620 which allow software and data to be transferred from the removable storage unit 5618 to computer system 5602.

Computer system 5602 can also include a communications interface 5624. Communications interface 5624 allows software and data to be transferred between computer system 5602 and external devices. Examples of communications interface 5624 can include a modem, a network interface (such as an Ethernet card), a communications port, a PCMCIA slot and card, etc. Software and data transferred via communications interface 5624 are in the form of signals which can be electronic, electromagnetic, optical or other signals capable of being received by communications interface 5624. These signals 5626 are provided to communications interface via a channel 5628. This channel 5628 carries signals 5626 and can be implemented using wire or cable, fiber optics, a phone line, a cellular phone link, an RF link and other communications channels.

In this document, the terms "computer program medium" and "computer usable medium" are used to generally refer to media such as removable storage device 5618, a hard disk installed in hard disk drive 5612, and signals 5626. These computer program products are means for providing software to computer system 5602.

Computer programs (also called computer control logic) are stored in main memory and/or secondary memory 5610. Computer programs can also be received via communications interface 5624. Such computer programs, when executed, enable the computer system 5602 to perform the features of the present invention as discussed herein. In particular, the computer programs, when executed, enable the processor 5604 to perform the features of the present invention. Accordingly, such computer programs represent controllers of the computer system 5602.

In an embodiment where the invention is implement using software, the software may be stored in a computer program product and loaded into computer system 5602 using removable storage drive 5614, hard drive 5612 or communications interface 5624. The control logic (software), when executed by the processor 5604, causes the processor 5604 to perform the functions of the invention as described herein.

In another embodiment, the invention is implemented primarily in hardware using, for example, hardware components such as application specific integrated circuits (ASICs). Implementation of the hardware state machine so as to perform the functions described herein will be apparent to persons skilled in the relevant art(s). In yet another embodiment, the invention is implemented using a combination of both hardware and software.

25.0 Example Data Structures

In a preferred embodiment, the present invention is implemented in software using various data structures. The following discussion describes exemplary data structures for use in this preferred embodiment. As will become apparent to one of ordinary skill in the art after reading this description, the invention can be implemented using alternative data structures.

First, a number of array indices are defined to facilitate indexing data stored in arrays. In the present invention, a planar surface is represented by the coefficients of an equation describing a line normal to the plane. The equation is of the form Ax+By+Cz+D=0. The four coefficients A, B, C and D are defined as four consecutive elements of an array. The first section of code below defines indices for these planar coefficient members.

```
/*dti.h main symbolic definition header file
#include <function.def>
/*define planar coef members*/
#define A 0
#define B 1
#define C 2
#define D 3
```

The next section of code defines the indices of a transform matrix for converting vectors between the global coordinate system and a local coordinate system. The transform matrix contains one set of L, M, N, and OR values for each of the three local axes: x', y', and z'. L represents the cosine of the angle between the local axis and the global x axis. This quantity is referred to as a direction cosine. Likewise, M represents the cosine of the angle between the local axis and the global y axis, and N represents the cosine of the angle between the local axis and the global z axis. The three OR values represent the global coordinates of the origin of the local coordinate system.

```
/*define local coordinate system transform matrix*/
#define L 0
#define M 1
#define N 2
#define OR 3
```

The next section of code defines other miscellaneous variables, including the values for a boolean variable and constants for translation between degrees and radians.

```
/*define other variables*/
#define TRUE 1
```

```
#define FALSE 0
#define PI 3.14159265358979323846
#define DEGRAD (PI/180.0)
#define DTR (180.0/PI)
```

The next section of code defines the array indices for the eight dispersion wavelengths tracked by the present invention.

```
/*define dispersion index codes*/
#define RED 0
#define ORANGE 1
#define YELLOW 2
#define GREEN 3
#define BLUE 4
#define VIOLET 5
#define UVIOLET 6
#define WHITE 7
```

The next few sections of code define various data structures used in the processing of a preferred embodiment of the present invention. The first data structure describes a facet.

```
/*define data structures*/
typedef struct facet{
    struct facet *next;
    struct resbuf *vert;
    ads_real coefs[4];
    ads_real acs[4][3];
    ads_real facdom[3][2];
    char factyp[20];
    char faclay[15];
    int facno;
};
```

As described above, the gemstone model is comprised of a number of facets. Each facet is represented by a facet data structure. The elements of the facet data structure will now be described.

The facet data structure is a linked list. The "facet *next" element is a pointer to the next facet data structure in the linked list of facets. The "resbuf *vert" element is a pointer to a linked list of the vertices of the facet. The "coefs" element is a one-by-four array containing the coefficients of the normal line for the plane of the facet. The "acs" element is a four-by-three array describing the relationship between the local coordinate system and the global coordinate system, as described above. The "facdom" element is a three-by-two array describing the "domain" (also referred to as the "bounding box") of the facet; the elements of the array define the minimum and maximum x, y and z values of the global coordinates found within the facet, thereby defining the "bounding box" of the facet.

The "factyp" element is an array of 20 characters that describes the facet type (for example, table, bezel, star, or main for a round-cut gemstone). The "faclay" element is an array of 15 integers that describes the layer of the gemstone in which the facet lies (for example, pavilion, girdle or crown). Each facet in the gemstone is numbered. The "facno" element contains the number of the facet.

The next data structure, called "ref_seg", is used to determine the portion of a facet illuminated by a beam. To make this determination, adjacent facet vertices are connected by a line segment. These segments collectively describe the boundary of the facet. The projection of the beam onto the plane of the facet is compared to these segments to determine what portion of the facet is illuminated by the beam.

```
typedef struct ref_seg{
    struct ref_seg *next;
    ads_real first[3];
    ads_real second[3];
    short int boole1;
    short int boole2;
    short int boole3;
    };
```

The "ref_seg" data structure is a linked list. The "ref_seg *next" element points to the next segment in the linked list of segments describing the boundary of the facet. The "first" and "second" elements contain the coordinates of the vertices joined by the segment; these coordinates are stored in facet-local coordinates. The "boole" elements are boolean variables describing the results of the vertex boolean determination. The "boole1" element is true if the first vertex falls within the beam. The "boole2" element is true if the second vertex falls within the beam. Even if neither vertex falls within the beam, it is still possible for a portion of the segment joining the vertices to fall within the beam. If this is the case, then the "boole3" element is true. The inclusion of this spatial knowledge within the ref_seg data structure results in significant conservation of computational resources.

During the beam-tracing phase of the operation of the present invention, a facet will refract a beam (that is, light will leave the gemstone through the facet) when the incident angle of the beam is less than the critical angle of the gemstone material, as described above. When this happens, an instance of the "refract" data structure is created to capture the data describing the light exiting the gemstone, for transport to the cameras.

```
typedef struct refract{
    struct refract *next;
    struct facet *outfac;
    struct resbuf *verts;
    ads_real dircos[8][3];
    ads_real pathwid;
    ads_real ang_dev;
    ads_real area_r;
    ads_real xsec_int[8];
    ads_real area_x[8];
    ads_real ampls[2];
    ads_real deg_pol;
    ads_real volum;
    };
```

The refract data structure is a linked list. The "refract *next" element is a pointer to the next refract data structure in the linked list. The "facet *outfac" element is a pointer to the facet data structure for the refracting facet (that is, the facet from which the light exited the gemstone). The "resbuf *verts" element is a pointer to a linked list of the vertices of the polygon describing the portion of the refracting facet that is illuminated by the light beam exiting the gemstone. The "dircos" element is an eight-by-three array containing the direction cosines of the dispersion components of the light exiting the gemstone. For each beam component (that is, red, orange, yellow, green, blue, violet, ultraviolet and white) the array contains the cosines of the angles between each axis of the global coordinate system and the Poynting vector of that dispersion component.

When a beam is refracted by a facet (that is, light exits the gemstone), the light is projected onto a "viewing plane" that is normal to the Poynting vector of the light beam. The viewing plane is used to measure the dispersion characteristics of the light. Two points are calculated on the plane: one for each of two selected dispersion components. The two points describe the intersections of the direction vectors of the two selected dispersion components with the viewing plane. The x axis of the local coordinate system for the viewing plane is a vector passing through both points. The y axis of the viewing plane local coordinate system also lies in the viewing plane.

The difference between the minimum and maximum y values of the projection of the refracted beam onto the viewing plane is known as the path width. The path width for the refracted beam is stored in the "pathwid" element. The "ang_dev" element stores the angle between the Poynting vectors for the red and ultraviolet dispersion components of the refracted beam. The "area_r" element contains the area of the refracting facet illuminated by the beam exiting that facet.

Each dispersion component in the refracted beam can be characterized by two measures of intensity: electric intensity and magnetic intensity. The "xsec_int" element is an eight-element array containing the average of these two intensities for each dispersion component. The "area_x" element is an eight-element array containing the area of the viewing plane illuminated by each dispersion component and the cross-sectional area of the white beam projected onto the camera's viewing plane. The "ampls" element is a two-element array that contains the amplitudes of the electric and magnetic components of the white monochromatic component. The "ampls" element is used to measure the brilliance component of the cut grade, and is also used to determine whether the refraction should be processed by the cameras. In one embodiment, when the "ampls" value for a particular refraction is below a predetermined threshold value, that refraction is discarded because further processing of that refraction would not significantly affect the grade. The "deg_pol" element contains a measure of the relative intensities of the electric and magnetic components of the white monochromatic component; this measure is known as the "degree of polarization."

Before leaving the stone, the refracted beam traverses a certain volume of gemstone material within the gemstone. The "volum" element contains a measure of this traversed volume. This measure can be used in conjunction with an absorption component to determine the color grade of the gemstone.

As light beams are propagated and reflected within the gemstone, a data structure is required to capture the data describing these light beams. Therefore, the present invention provides a data structure called "ltbeam". As described above, the light beam calculation proceeds bounce by bounce. Within a particular bounce, each light beam is described by a "ltbeam" data structure. When a light beam in a first bounce is reflected to create one or more light beams in a second bounce, the data elements of the light beam data structures in the second bounce are derived from the data elements of the light beam data structure in the first bounce. Once the light beams in the second bounce are calculated, the light beam data structure in the first bounce can be released. Using this technique, light beam data structures are required simultaneously in a maximum of only two bounces. Previous light beam data structures can be released, resulting in a highly efficient memory resource allocation technique. The light beam data structure is presented below.

```
typedef struct ltbeam{
    struct ltbeam *next;
    struct facet *inface;
    struct facet *outface;
    struct facet *parent;
    struct resbuf *verts;
    struct resbuf *path;
    ads_real domain[3][2];
    ads_real dircos[8][3];
    ads_real index;
    ads_real area_r
    ads_real area_x
    ads_real xsec_intp;
    ads_real xsec_ints;
    ads_real ampls[2];
    ads_real disp_int[7];
    ads_real deg_pol;
    ads_real volum;
};
```

The light beam data structure is a linked list. The "ltbeam *next" element is a pointer to the next light beam data structure in the linked list. Beams in different bounces are not linked to each other; only beams in the same bounce are linked together. The "facet_*inface" element is a pointer to the data structure for the facet through which the light in the beam originally entered the gemstone. The "facet *outface" element is a pointer to the data structure for the facet through which the previous refraction of the beam occurred. The "facet *parent" element contains a pointer to the data structure for the facet from which the light beam was just reflected (termed the "parent" facet for the beam). The "resbuf*verts" data structure is a pointer to a linked list of vertices of a polygon describing the portion of the parent facet illuminated by the reflected light beam. The "resbuf *path" element is a pointer to a linked list of vertices for a polygon describing the projection of the reflection of the light beam onto the parent facet. The "domain" element is a 3×2 array describing the coordinates of the bounding box for the reflection of the light beam. The "dircos" element is an 8×3 array containing the direction cosines (with respect to the axes of the global coordinate system) for the dispersion components of the light beam. The "index" element is the index of refraction for the gemstone material in which the reflecting facet of the light beam lies. The "area_r" element contains the area of the reflection of the light beam in the reflecting facet. The "area_x" element contains the cross sectional area of the light beam. This quantity is calculated by multiplying the cosine of the angle of incidence of the light beam upon the reflecting facet by the area_r. The intensities of the magnetic and electric components of the white monochromatic components of the light beam are stored in the "xsec_intp" and "xsec_ints" elements, respectively. When a light beam is refracted, these two values are averaged to create the values stored in the "xsec_int" element of the "refract" data structure. The "ampls" element is a 2-element array that stores the amplitudes of the electric and magnetic components of the white monochromatic component of the light beam, as described above with respect to the "refract" data structure. The "ampls" element is used to limit the "lifetime" of a beam within the gemstone. In one embodiment, when the "ampls" value for a particular light beam falls below a predetermined threshold value, that lightbeam is discarded because further processing of the light beam would not significantly affect the grade. The "disp_int" element is a 7-element array that contains the intensities for all of the dispersion components except the white monochromatic components. The "deg_pol" element contains the degree of polarization of the white monochromatic component of the light beam, calculated as described above with respect to the "refract" data structure. The "volume" element contains a running total of the volume of gemstone material traversed by the light beams and its parent light beams since entering the gemstones.

In a preferred embodiment of the present invention, a data structure is established to contain the data describing each wavelength that is tracked in order to calculate dispersion. This data structure, called "dispbuf" is shown below.

```
typedef struct dispbuf{
    struct dispbuf *next;
    int index;
    ads_real indexr;
    ads_real wavlen;
    ads_real n_min;
    ads_real n_max;
    ads_real wv_min;
    ads_real wv_max;
};
```

In a preferred embodiment of the present invention, eight dispersion components are monitored. Therefore, eight "dispbuf" data structures are required. The "dispbuf" data structure is a linked list. The "dispbuf *next" element points to the next data structure in the linked list. The "index" element contains the integer index value assigned to the dispersion component described by the data structure. For example, referring to the variable definitions above, the "index" value for the green dispersion component is three. The "indexr" data element is the absolute index refraction for the wavelength of the dispersion component. The "wavlen" data element contains the actual wavelength of the dispersion component. The minimum and maximum indices of refraction for this wavelength are stored in the "n_min" and "n_max" data elements, respectively. The minimum and maximum wavelengths for the dispersion component are stored in the "wv_min" and "wv_max" data elements, respectively.

As described above, when light exits the gemstone, the data describing that light is captured in the "refract" data structure. As part of gemstone cut grading, the data collected by the "refract" data structures is processed by the cameras. In a preferred embodiment of the present invention, a data structure is established to contain not only data describing the camera but also data captured by the camera. That data structure, called "camera," is presented below.

```
typedef struct camera{
    struct camera *next;
    struct zone *zones;
    ads_real inspt[3];
    ads_real acs[4][3];
    ads_real maxhang;
    ads_real minhang;
    ads_real maxvang;
    ads_real minvang;
    ads_real maxhrang;
    ads_real minhrang;
    ads_real maxvrang;
    ads_real minvrang;
    ads_real v_area
    ads_real r_area[8];
    ads_real intens[8];
    ads_real power[8];
    ads_real spectdens;
    ads_real intens_dur;
    ads_real enr_dens;
    ads_real d_enr_dens;
    ads_real volume;
```

```
        ads_real vol_dens;
        int noviszon;
        int no_ref;
        };
```

The camera data structure is a linked list data structure. The "camera *next" data element points to the next camera data structure in the linked list. As described above, for each facet of the gemstone that is visible to a camera, a "zone" is established. The "zone *zones" data element points to a linked list of zones for the camera. The "inspt" data element contains the global coordinates for the insertion point for the camera. In one embodiment of the present invention, the insertion point of the camera is the global origin. As described above, the origin of the global coordinate system is at the geometric center of the girdle at the intersection of the girdle and the pavilion.

The "acs" data element describes the orientation and position of the local camera local coordinate system with respect to the global coordinate system. As described above, the "acs" element is a four-by-three array containing the direction cosines of each axis of the local coordinate system with respect to each axis of the global coordinate system, and the global coordinates of the origin of the local coordinate system. The z axis of the camera local coordinate system points toward the origin of the global coordinate system.

As seen from the global origin, the camera "lens" is a bounded plane that can be described in terms of minimum and maximum horizontal and vertical angles measured at the global origin. The maximum and minimum horizontal angles are stored in the "maxhang" and "minhang" data elements. The maximum and minimum vertical angles for the camera are stored in the "maxvang" and "minvang" data elements.

In some applications, it is desirable to permit camera lenses to overlap. Therefore, the camera data structure includes data elements to describe the extent of the overlap, which can be described as a bounded plane somewhat larger than the camera lens. The maximum and minimum horizontal angles for this section are stored in the "maxhrang" and "minhrang" data elements, respectively. The maximum and minimum vertical angles for the section are stored in the "maxvrang" and "minvrang" data elements.

The "V_area" data element contains the total area of the facets visible to a camera when projected onto the viewing plane of the camera The "r_area" data element is an array containing one value for each dispersion component; each value contains the total area occupied by refracted beams for that dispersion component, as projected onto the viewing plane of the camera. The "intens" element is an array containing one element for each dispersion intensity component; each element contains the total intensity visible to the camera for that dispersion component. As noted above, only light refracted by facets in the crown is measured.

The "power" data element contains the total optical power visible to the camera for each dispersion component. In one embodiment a measure of the ratio of the dispersed energy to the surface area of the refracting facet, also known as the "spectral density" of the beam, summed for all dispersion components, is used as a grading component; this value is stored as the "spectdens" element The "intens_dur" data element is a measure of the dispersion of the beam for all facets visible to the camera. This quantity is determined by multiplying the path-length, intensity, and cosine of the angle of deviation for each dispersion component and summing the products. This quantity is a measure of the dispersion, or "fire," of the gemstone.

The "enr_dens" data element is a direct measure of the brilliance of the gemstone, and contains a measure of the total energy density emanating from all crown facets visible to the camera. The "d_enr_dens" is a measure of the total dispersed energy density for all crown facets visible to the camera. The "volume" data element is a measure of the total volume of gemstone material traversed by the refracted beam, as described above. The "vol_dens" data element is a measure of the volumetric density visible to the camera (that is, the total volume of the beam divided by the area of the refraction as seen by the camera. The integer data element "noviszon" is the total number of zones visible to the camera. The integer data element "no_ref" is the number of refracted beams visible to the camera.

The zone data structure is presented below. There is one such data structure for each zone, for each camera. A particular facet can have many corresponding zones: one for each camera to which the facet is visible. These zones need not have the same data element values.

```
        typedef struct zone{
        struct zone *next;
        struct refract *images;
        struct refract *last;
        struct facet *face;
        ads_real z_area
        ads_real cov_perc;
        ads_real r_area[8];
        ads_real intens[8];
        ads_real power[8];
        ads_real spectdens;
        ads_real intens_dur;
        ads_real enr_dens;
        ads_real d_enr_dens;
        ads_real av_angdev;
        ads_real volume;
        ads_real vol_dens;
        int no_ref;
        int visible;
        int count;
        };
```

The zone data structure is a linked list. The "zone *next" data element is a pointer to the next zone data structure in the linked list. The "refract *images" data element is a pointer to one or more data elements for rendering graphic images for displaying the gemstone model to a user. The "refract *last" data element is a pointer to the last such graphics image in memory. The "facet *face" data element is a pointer to the facet data structure for the facet that corresponds to the zone.

The "z_area" data element is the area of the projection of the zone onto the viewing plane of the camera. The "cov_perc" data element is z_area divided by the total area of all visible zones projected on the viewing plane of the camera, expressed as a percentage. The "r_area" component is an array containing the area for each dispersion component; each element contains the total area illuminated by refractions within the zone for that dispersion component. The "intens" data element is an array containing the total intensity visible to the camera for the zone for each dispersion component. The "power" data element is an array containing the total optical power visible to the camera for the zone for each dispersion component.

The "spectdens", "intens_dur", "enr_dens", and "d_enr_dens" data elements are as described for the camera data structure, but limited to the particular zone. Corresponding values are summed to provide the values for the camera. For example, the "spectdens" value for a camera is derived by summing the "spectdens" values for each crown zone visible to the camera.

The "av_angdev" data element represents the average angle of deviation, and is calculated by dividing the sum of the angles of deviation by the number of such angles (i.e., the number of refractions). The "volume" and "vol_dens" data elements represent the total volume and total volumetric density for the refracted beams visible to the camera from the zone. The "no_ref" data element is the total number of refractions visible to the camera from the zone. The "visible" data element is a boolean value that represents whether the zone is visible to the camera. The "count" data element is an integer representing the cardinal number assigned to this zone for this camera.

As part of the grading algorithm, data is collected for all of the facets of a particular type (e.g., break, main, table). The data structure used for this collection, called "zone_nams", is presented below.

```
typedef struct zone_nams{
struct zone_nams *next;
char name[20];
int number;
ads_real r_total;
ads_real r_mean;
ads_real r_dev;
int i_total;
int i_mean;
int i_dev;
};
```

This data structure is a linked list. The "zone-nams *next" data element is a pointer to the next data structure in the linked list. There is one "zone_namns" data structure for each facet type. The "char name" data element is a string containing the name of the type of facet (for example, break, main, star, etc.). The "number" data element is a unique integer assigned to the zone type. The "r_total," "r_mean," and "r_dev" data elements contain the total, mean and standard deviation for the zone areas of the specified zone type. The "i_total," "i_mean," and "i_dev" data elements contain the total, mean and standard deviation for the intensities collected by the zones of the specified zone type.

In one embodiment, a data structure is provided to collect data regarding the illumination model selected. The "vector" data structure is used to describe each light vector incident on the gemstone. The "vector" data structure is presented below.

```
typedef struct vector{
struct vector *next;
ads_real srcpt[3];
ads_real tgtpt[3];
ads_real xintp;
ads_real xints;
};
```

The vector data structure is a linked list. The "vector *next" data element points to the next data structure in the linked list. The "srcpt" and "tgtpt" data elements are source and target points, respectively, for an illumination vector. The "xintp" and "xints" data elements describe the electric and magnetic intensities, respectively, of the illumination vector.

In another embodiment, a spherical diffuse illumination model is employed; a different data structure is used to describe the range of this lighting model. This data structure, called "angl_mg" is presented below.

```
typedef struct angl_rang{
struct angl_rang *next;
ads_real inspt[3];
ads_real minhor;
ads_real maxhor;
ads_real hresol;
ads_real minver;
ads_real maxver;
ads_real vresol;
};
```

This data structure is a linked list. The "angl_rng *next" data element points to the next data structure in the linked list. The "inspt" data element contains the insertion point for the illumination source. In a preferred embodiment, the insertion point is the global origin. The spherical diffuse illumination model is characterized by multiple point sources of illumination. The arrangement of the point sources is specified by values for minimum and maximum horizontal angles, horizontal resolution, minimum and maximum vertical angles, and vertical resolution, which are stored in the "minhor", "maxhor", "hresol", "minver", "maxver", and "vresol" data elements.

A similar data structure is provided to describe the positions of the cameras. This data structure, called "cam_dat", is presented below.

```
typedef struct cam_dat{
struct cam_dat *next;
ads_real inspt[3];
ads_real minhor;
ads_real maxhor;
ads_real hresol;
ads_real minver;
ads_real maxver;
ads_real vresol;
ads_real v_over;
ads_real h_over;
};
```

The "minhor," "maxhor," "hresol," "minver," and "maxver," elements describe the angular extent of the camera lens, excluding overlap. The "v_over" and "h_over" elements describe the angular extent of the camera lens overlap.

Many of the calculation parameters for the present invention are user-selectable. These user-selectable configuration settings can be saved and retrieved for later use. The grade for particular gem cut is a function of these configurations. These configuration parameters are stored in a data structure called "config", which is presented below.

```
typedef struct config{
int nobncs;
ads_real min_area;
ads_real min_ampl;
/*camera config*/
ads_real cinspt[3];
ads_real cminhor;
ads_real cmaxhor;
ads_real chresol;
ads_real cminver;
ads_real cmaxver;
ads_real cvresol;
ads_real cv_over;
ads_real ch_over;
/*lights config*/
ads_real slinspt[3];
```

```
       ads_real slminhor;
       ads_real slmaxhor;
       ads_real slhresol;
       ads_real slminver;
       ads_real slmaxver;
       ads_real slvresol;
     };
```

The "nobncs" data element is an integer specifiing the maximum number of bounces that are to be processed. The processing of the model can also be limited by the area and/or the amplitude of the light beam. For example, when the cross-sectional area of a light beam falls below a certain threshold, that projection should not be subject to further processing. A user can select this minimum area, which is stored in the "min_area" data element. Likewise, the user can select an amplitude threshold below which beams should not be processed; this value is stored in the "min_ampl" data element.

This data structure also includes camera configuration settings. The "cinspt" data element contains the global coordinates for the camera insertion point. The remaining camera configuration parameters describe the positioning of the cameras, as described above.

This data structure also includes the configuration settings for the lighting model. The "slinspt" data element contains the global coordinates for the lighting insertion point, and the remaining lighting parameters describe the locations of the illumination point sources, as described above.

Finally, a data structure is provided to store the components of the gemstone grade. These components are "enr_dens" for energy density (also known as brilliance), "spect_lum" for spectral luminance (also known as dispersion), and scint" for scintillation.

26.0. Conclusion

While various embodiments of the present invention have been described above, it should be understood that they have been presented by way of example only, and not limitation. Thus, the breadth and scope of the present invention should not be limited by any of the above-described exemplary embodiments, but should be defined only in accordance with the following claims and their equivalents.

I claim:

1. A method for grading the cut of a gemstone, comprising the steps of:

illuminating a gemstone model using an illumination model, wherein said gemstone model defines the geometry and position of the gemstone facets, and wherein said illumination model produces a light beam;

refracting said light beam into said gemstone model through a first facet of said gemstone model to produce a refracted light beam;

reflecting said refracted light beam within said gemstone model from a second facet of said gemstone model to produce a reflected light beam;

refracting said refracted and reflected light beams out of said gemstone model through a third facet of said gemstone model to produce an exiting light beam; and measuring said exiting light beam.

2. The method of claim 1, further comprising the step of generating said gemstone model.

3. The method of claim 2, further comprising the step of: defining facet types and facet locations for the gemstone to be graded.

4. The method of claim 3, further comprising the step of: considering cut proportion for the gemstone to be graded.

5. The method of claim 3, further comprising the step of: defining said facet types and facet locations in a global coordinate system of the gemstone to be graded.

6. The method of claim 3, further comprising the step of: defining said facet types and facet locations in a linked list data structure.

7. The method of claim 2, further comprising the step of: generating said gemstone model to represent an existing cut or a proposed cut.

8. The method of claim 1, further comprising the step of: generating said illumination model.

9. The method of claim 8, further comprising the step of: defining a light source.

10. The method of claim 8, further comprising the step of: defining a plurality of light sources arranged in an array above a crown of said gemstone model.

11. The method of claim 8, further comprising the step of: defining a light source to simulate specified lighting conditions for the gemstone to be evaluated.

12. The method of claim 1, wherein said measuring step comprises the steps of:

generating a camera model having a camera;

projecting a given facet onto said camera when said given facet is visible to said camera to produce a zone;

dividing the flux of each light beam refracted out of the gemstone model by said given facet by the area of said zone to produce a plurality of flux densities; and summing said flux densities for said given facet for said camera to produce a given facet camera flux density.

13. The method of claim 12, wherein said camera model includes a plurality of cameras and said given facet is of a given facet type, and wherein said measuring step further comprises the step of:

summing said given facet camera flux densities for the given facet type for said plurality of cameras to produce a given facet type sum;

dividing said given facet type sum by the number of facets in said gemstone model of the given facet type to produce a given facet type average;

summing said facet type averages for all of the facet types in said gemstone model to produce a facet type average sum; and dividing said facet type average sum by the number of facet types in said gemstone model to produce a composite flux density measurement for the gemstone.

14. The method of claim 1, wherein said reflecting step comprises the steps of:

projecting said refracted light beam, along the direction of travel of said refracted light beam, onto the plane of said second facet of said gemstone model to produce a projection of said refracted light beam;

computing the geometry of the intersection of said second facet and said projection of said refracted light beam; and computing a reflected direction of travel based on said direction of travel of said refracted light beam and the orientation of said second facet;

whereby said reflected light beam is defined by said geometry and said reflected direction of travel.

15. The method of claim 1, wherein said gemstone model is defined in a coordinate space having three variables, and wherein said reflecting step comprises the steps of:

projecting the geometry of said second facet onto a coordinate plane defined by setting a first coordinate space variable to zero to produce a facet projection;

circumscribing said facet projection with a rectangle defined by the minimum and maximum second and third coordinate space variables of the vertices of said facet projection to produce a facet bounding box;

projecting said refracted light beam onto the plane of said facet to produce an illumination;

projecting the geometry of said illumination onto said coordinate plane to produce an illumination projection; and circumscribing said illumination projection with a rectangle defined by the minimum and maximum second and third coordinate space variables of the vertices of said illumination projection to produce a projection bounding box;

wherein said refracted light beam illuminates said second facet when said facet bounding box and said projection bounding box overlap.

16. A method for modeling the propagation of light in an optical system, comprising the steps of:

projecting a beam of light at a first one of a plurality of surfaces of said optical system, wherein said beam of light is represented by an illumination model and said plurality of surfaces are represented by an optical system model;

modeling the propagation of light from said first one of said plurality of surfaces of said optical system through the optical system as defined by said optical system model; and measuring the attributes of the light beam at a predetermined point in the optical system.

17. A method for establishing maximum attribute values for a gemstone cut for use in evaluating gemstones having said gemstone cut comprising the steps of:

varying a proportion parameter for the gemstone cut to obtain a plurality of gemstone models, each of said gemstone models having a different proportion permutation;

evaluating each of said gemstone models to obtain a set of values for each attribute; and selecting the maximum value of each attribute from said set of attribute values to establish maximum attribute values for the gemstone cut.

18. The method of claim 17, wherein said evaluating step comprises the steps of:

illuminating said gemstone models using an illumination model, wherein said illumination model produces a light beam;

refracting said light beam into said gemstone models through respective first facets of said gemstone models to produce corresponding refracted light beams;

reflecting said refracted light beams within said gemstone models from respective second facets of said gemstone models to produce corresponding reflected light beams;

refracting at least one of said refracted and reflected light beams out of said gemstone models through respective third facets of said gemstone models to produce corresponding exiting light beams; and measuring attributes of said exiting light beams.

19. A system for grading the cut of a gemstone, comprising:

means for illuminating a gemstone model using an illumination model, wherein said gemstone model defines the geometry and position of the gemstone facets, and wherein said illumination model produces a light beam;

means for refracting said light beam into said gemstone model through a first facet of said gemstone model to produce a refracted light beam;

means for reflecting said refracted light beam within said gemstone model from a second facet of said gemstone model to produce a reflected light beam;

means for refracting at least one of said refracted and reflected light beams out of said gemstone model through a third facet of said gemstone model to produce an exiting light beam; and means for measuring said exiting light beam.

20. The system of claim 19, further comprising:

means for generating said gemstone model.

21. The system of claim 20, further comprising:

means for generating data defining facet types and facet locations for the gemstone.

22. The system of claim 21, further comprising:

means for considering cut proportions for the gemstone.

23. The system of claim 21, further comprising:

means for defining said facet types and facet locations in a global coordinate system of the gemstone.

24. The system of claim 21, further comprising:

means for defining said facet types and facet locations in a linked list data structure.

25. The system of claim 20, further comprising:

means for generating said gemstone model to represent an existing cut or a proposed cut.

26. The system of claim 19, further comprising:

means for generating said illumination model.

27. The system of claim 26, further comprising:

means for defining a light source.

28. The system of claim 26, further comprising:

means for defining a plurality of light sources arranged in an array above a crown of said gemstone model.

29. The system of claim 26, further comprising:

means for defining a light source to simulate specified lighting conditions for the gemstone to be evaluated.

30. The system of claim 19, wherein said means for measuring comprises:

means for generating a camera model having a camera;

means for projecting a given facet onto said camera when said given facet is visible to said camera to produce a zone;

means for dividing the flux of each light beam refracted out of the gemstone model by said given facet by the area of said zone to produce a plurality of flux densities; and means for summing said flux densities for said given facet for said camera to produce a given facet camera flux density.

31. The system of claim 30, wherein said camera model includes a plurality of cameras and said given facet is of a given facet type, and wherein said means for measuring further comprises:

means for summing said given facet camera flux densities for the given facet type for said plurality of cameras to produce a given facet type sum;

means for dividing said given facet type sum by the number of facets in said gemstone model of the given facet type to produce a given facet type average;

means for summing said facet type averages for all of the facet types in said gemstone model to produce a facet type average sum; and means for dividing said facet type average sum by the number of facet types in said gemstone model to produce a composite flux density measurement for the gemstone.

32. The system of claim 19, wherein said means for reflecting comprises:

means for projecting said refracted light beam, along the direction of travel of said refracted light beam, onto the plane of said second facet of said gemstone model to produce a projection of said refracted light beam;

means for computing the geometry of the intersection of said second facet and said projection of said refracted light beam; and means for computing a reflected direction of travel based on said direction of travel of said refracted light beam and the orientation of said second facet;

whereby said reflected light beam is defined by said geometry and said reflected direction of travel.

33. The system of claim 19, wherein said gemstone model is defined in a coordinate space having three variables, and wherein said reflecting step comprises:

means for projecting the geometry of said second facet onto a coordinate plane defined by setting a first coordinate space variable to zero to produce a facet projection;

means for circumscribing said facet projection with a rectangle defined by the minimum and maximum second and third coordinate space variables of the vertices of said facet projection to produce a facet bounding box;

means for projecting said refracted light beam onto the plane of said facet to produce an illumination;

means for projecting the geometry of said illumination onto said coordinate plane to produce an illumination projection; and means for circumscribing said illumination projection with a rectangle defined by the minimum and maximum second and third coordinate space variables of the vertices of said illumination projection to produce a projection bounding box;

wherein said refracted light beam illuminates said second facet when said facet bounding box and said projection bounding box overlap.

34. A system for modeling the propagation of light in an optical system, comprising:

means for projecting a beam of light at one of a plurality of surfaces of the optical system, wherein said beam of light is represented by an illumination model and said plurality of surfaces are represented by an optical system model;

means for modeling the propagation of said beam of light within the optical system according to said optical system model; and means for measuring said beam of light at a predetermined point in the optical system.

35. A system for establishing maximum attribute values for a gemstone cut for use in evaluating gemstones having said gemstone cut, comprising:

means for varying a proportion parameter for the gemstone cut to obtain a plurality of gemstone models, each of said gemstone models having a different proportion permutation;

means for evaluating each of said gemstone models to obtain a set of values for each attribute; and means for selecting the maximum value of each attribute from said set of attribute values to establish maximum attribute values for the gemstone cut.

36. The system of claim 35, wherein said means for evaluating comprises:

means for illuminating said gemstone models using an illumination model wherein said illumination model produces a light beam;

means for refracting said light beam into said gemstone models through respective first facets of said gemstone models to produce corresponding refracted light beams;

means for reflecting said refracted light beams within said gemstone models from respective second facets of said gemstone models to produce corresponding reflected light beams;

means for refracting at least one of said refracted and reflected light beams out of said gemstone models through respective third facets of said gemstone models to produce corresponding exiting light beams; and means for measuring attributes of said exiting light beams.

37. In a system for grading the cut of a gemstone, a computer program product comprising a computer usable medium having computer readable program code means embodied in said medium for causing an application program to execute on a computer, said computer readable program code means comprising:

a first computer readable program code means for causing said computer to illuminate a gemstone model using an illumination model, wherein said gemstone model defines the geometry and position of the gemstone facets, and wherein said illumination model produces a light beam;

a second computer readable program code means for causing said computer to refract said light beam into said gemstone model through a first facet of said gemstone model to produce a refracted light beam;

a third computer readable program code means for causing said computer to reflect said refracted light beam within said gemstone model from a second facet of said gemstone model to produce a reflected light beam;

a fourth computer readable program code means for causing said computer to refract at least one of said refracted and reflected light beams out of said gemstone model through a third facet of said gemstone model to produce an exiting light beam; and a fifth computer readable program code means for causing said computer to measure said exiting light beam.

38. The computer program product of claim 37, wherein said computer readable program code means further comprises:

a computer readable program code means for causing said computer to generate said gemstone model.

39. The computer program product of claim 38, wherein said computer readable program code means further comprises:

a computer readable program code means for causing said computer to generate data defining facet types and facet locations for the gemstone.

40. The computer program product of claim 39, wherein said computer readable program code means further comprises:

a computer readable program code means for causing said computer to consider cut proportions for the gemstone.

41. The computer program product of claim 39, wherein said computer readable program code means further comprises:

a computer readable program code means for causing said computer to define said facet types and facet locations in a global coordinate system of the gemstone.

42. The computer program product of claim 39, wherein said computer readable program code means further comprises:

a computer readable program code means for causing said computer to define said facet types and facet locations in a linked list data structure.

43. The computer program product of claim 38, wherein said computer readable program code means further comprises:

a computer readable program code means for causing said computer to generate said gemstone model to represent an existing cut or a proposed cut.

44. The computer program product of claim 37, wherein said computer readable program code means further comprises:

a computer readable program code means for causing said computer to generate said illumination model.

45. The computer program product of claim 44, wherein said computer readable program code means further comprises:

a computer readable program code means for causing said computer to define a light source.

46. The computer program product of claim 44, wherein said computer readable program code means further comprises:

a computer readable program code means for causing said computer to define a plurality of light sources arranged in an array above a crown of said gemstone model.

47. The computer program product of claim 44, wherein said computer readable program code means further comprises:

a computer readable program code means for causing said computer to define a light source to simulate specified lighting conditions for the gemstone to be evaluated.

48. The computer program product of claim 37, wherein said fifth computer readable program code means comprises:

a computer readable program code means for causing said computer to generate a camera model having a camera;

a computer readable program code means for causing said computer to project a given facet onto said camera when said given facet is visible to said camera to produce a zone;

a computer readable program code means for causing said computer to divide the flux of each light beam refracted out of the gemstone model by said given facet by the area of said zone to produce a plurality of flux densities; and a computer readable program code means for causing said computer to sum said flux densities for said given facet for said camera to produce a given facet camera flux density.

49. The computer program product of claim 37, wherein said third computer readable program code means comprises:

a computer readable program code means for causing said computer to project said refracted light beam, along the direction of travel of said refracted light beam, onto the plane of said second facet of said gemstone model to produce a projection of said refracted light beam;

a computer readable program code means for causing said computer to compute the geometry of the intersection of said second facet and said projection of said refracted light beam; and a computer readable program code means for causing said computer to compute a reflected direction of travel based on said direction of travel of said refracted light beam and the orientation of said second facet;

whereby said reflected light beam is defined by said geometry and said reflected direction of travel.

50. The computer program product of claim 48, wherein said camera model includes a plurality of cameras and said given facet is of a given facet type, and wherein said fifth computer readable program code means further comprises:

a computer readable program code means for causing said computer to sum said given facet camera flux densities for the given facet type for said plurality of cameras to produce a given facet type sum;

a computer readable program code means for causing said computer to divide said given facet type sum by the number of facets in said gemstone model of the given facet type to produce a given facet type average;

a computer readable program code means for causing said computer to sum said facet type averages for all of the facet types in said gemstone model to produce a facet type average sum; and a computer readable program code means for causing said computer to divide said facet type average sum by the number of facet types in said gemstone model to produce a composite flux density measurement for the gemstone.

51. The computer program product of claim 37, wherein said gemstone model is defined in a coordinate space having three variables, and wherein said third computer readable program code means comprises:

a computer readable program code means for causing said computer to project the geometry of said second facet onto a coordinate plane defined by setting a first coordinate space variable to zero to produce a facet projection;

a computer readable program code means for causing said computer to circumscribe said facet projection with a rectangle defined by the minimum and maximum second and third coordinate space variables of the vertices of said facet projection to produce a facet bounding box;

a computer readable program code means for causing said computer to project said refracted light beam onto the plane of said facet to produce an illumination;

a computer readable program code means for causing said computer to project the geometry of said illumination onto said coordinate plane to produce an illumination projection; and a computer readable program code means for causing said computer to circumscribe said illumination projection with a rectangle defined by the minimum and maximum second and third coordinate space variables of the vertices of said illumination projection to produce a projection bounding box;

wherein said refracted light beam illuminates said second facet when said facet bounding box and said projection bounding box overlap.

52. In a system for for modeling the propagation of light in an optical system, a computer program product comprising a computer usable medium having computer readable program code means embodied in said medium for causing an application program to execute on a computer, said computer readable program code means comprising:

a computer readable program code means for causing said computer to project a beam of light at one of a plurality of surfaces of the optical system, wherein said beam of light is represented by an illumination model and said plurality of surfaces are represented by an optical system model;

a computer readable program code means for causing said computer to model the propagation of said beam of light within the optical system according to said optical system model; and a computer readable program code means for causing said computer to measure said beam of light at a predetermined point in the optical system.

53. In a system for establishing maximum attribute values for a gemstone cut for use in evaluating gemstones having said gemstone cut, a computer program product comprising a computer usable medium having computer readable program code means embodied in said medium for causing an application program to execute on a computer, said computer readable program code means comprising:

a first computer readable program code means for causing said computer to vary a proportion parameter for the gemstone cut to obtain a plurality of gemstone models, each of said gemstone models having a different proportion permutation;

a second computer readable program code means for causing said computer to evaluate each of said gemstone models to obtain a set of values for each attribute; and a third computer readable program code means for causing said computer to select the maximum value of each attribute from said set of attribute values to establish maximum attribute values for the gemstone cut.

54. The system of claim 53, wherein said second computer readable program code means comprises:

a computer readable program code means for causing said computer to illuminate said gemstone models using an illumination model, wherein said illumination model produces a light beam;

a computer readable program code means for causing said computer to refract said light beam into said gemstone models through respective first facets of said gemstone models to produce corresponding refracted light beams;

a computer readable program code means for causing said computer to reflect said refracted light beams within said gemstone models from respective second facets of said gemstone models to produce corresponding reflected light beams;

a computer readable program code means for causing said computer to refract at least one of said refracted and reflected light beams out of said gemstone models through respective third facets of said gemstone models to produce corresponding exiting light beams; and a computer readable program code means for causing said computer to measure attributes of said exiting light beams.

55. A method for grading the cut of a gemstone, comprising the steps of:

illuminating a gemstone model with a light source, wherein said gemstone model defines the geometry and position of the gemstone facets;

refracting said light source into said gemstone model through a first facet of said gemstone model to produce a refracted light;

reflecting said refracted light within said gemstone model from a second facet of said gemstone model to produce a reflected light;

refracting said refracted and reflected lights out of said gemstone model through a third facet of said gemstone model to produce an exiting light; and measuring said exiting light.

56. The method of claim 55, further comprising the step of generating said gemstone model for a gemstone to be graded, wherein said gemstone model comprises a data representation of the cut of the gemstone.

57. The method of claim 56, further comprising the step of: defining said facet types and facet locations of the gemstone to be graded in a global coordinate system.

58. The method of claim 56, further comprising the step of: defining said facet types and facet locations in a linked list data structure.

59. The method of claim 55, further comprising the step of: generating said gemstone model to represent an existing cut or a proposed cut.

60. The method of claim 55, further comprising the steps of:

illuminating said gemstone model using an illumination model, wherein said illumination model produces a light beam;

refracting said light beam into said gemstone model through a first facet of said gemstone model to produce a refracted light beam;

reflecting said refracted light beam within said gemstone model from a second facets of said gemstone model to produce a reflected light beam;

refracting said refracted and reflected light beams out of said gemstone model through a third facet of said gemstone model to produce an exiting light beams; and measuring attributes of said exiting light beam.

61. A system for grading the cut of a gemstone, comprising:

means for illuminating a gemstone model with a light source, wherein said gemstone model defines the geometry and position of the gemstone facets, means for refracting said light into said gemstone model through a first facet of said gemstone model to produce a refracted light;

means for reflecting said refracted light within said gemstone model from a second facet of said gemstone model to produce a reflected light;

means for refracting at least one of said refracted and reflected light out of said gemstone model through a third facet of said gemstone model to produce an exiting light; and means for measuring said exiting light.

62. The system of claim 61, further comprising:

means for generating data defining facet types and facet locations for the gemstone.

63. The system of claim 62, further comprising:

means for defining said facet types and facet locations in a global coordinate system of the gemstone.

64. The system of claim 62, further comprising:

means for defining said facet types and facet locations in a linked list data structure.

65. The system of claim 61, further comprising;

means for defining a plurality of light sources arranged in an array above a crown of said gemstone model.

66. The system of claim 61, further comprising:

means for defining a light source to simulate specified lighting conditions for the gemstone to be evaluated.

67. In a system for grading the cut of a gemstone, a computer program product comprising a computer usable medium having computer readable program code means embodied in said medium for causing an application program to execute on a computer, said computer readable program code means comprising:

- a first computer readable program code means for causing said computer to illuminate a gemstone model, wherein said gemstone model defines the geometry and position of the gemstone facets;
- a second computer readable program code means for causing said computer to refract said light beam into said gemstone model through a first facet of said gemstone model to produce a refracted light;
- a third computer readable program code means for causing said computer to reflect said refracted light beam within said gemstone model from a second facet of said gemstone model to produce a reflected light;
- a fourth computer readable program code means for causing said computer to refract at least one of said refracted and reflected light out of said gemstone model through a third facet of said gemstone model to produce an exiting light; and
- a fifth computer readable program code means for causing said computer to measure said exiting light.

68. Tie computer program product of claim 67, wherein said computer readable program code means further comprises:

a computer readable program code means for causing said computer to generate said gemstone model.

69. The computer program product of claim 68, wherein said computer readable program code means further comprises:

a computer readable program code means for causing said computer to generate data defining facet types and facet locations for the gemstone.

70. The computer program product of claim 69, wherein said computer readable program code means further comprises:

a computer readable program code means for causing said computer to define said facet types and facet locations in a global coordinate system of the gemstone.

71. The computer program product of claim 69, wherein said computer readable program code means ether comprises:

a computer readable program code means for causing said computer to define said facet types and facet locations in a linked list data structure.

72. The computer program product of claim 67, wherein said computer readable program code means further comprises:

a computer readable program code means for causing said computer to generate an illumination model to illuminate said gemstone model with a light beam.

73. The computer program product of claim 72, wherein said computer readable program code means further comprises:

a computer readable program code means for causing said computer to define a plurality of light sources arranged in an array above a crown of said gemstone model.

74. The computer program product of claim 67, wherein said computer readable program code means further comprises:

a computer readable program code means for causing said computer to define a light source to simulate specified lighting conditions for the gemstone to be evaluated.

\* \* \* \* \*